US011801242B2

(12) United States Patent
Zhou et al.

(10) Patent No.: US 11,801,242 B2
(45) Date of Patent: Oct. 31, 2023

(54) COMPOSITIONS AND METHODS FOR ADJUVANT CANCER THERAPEUTICS

(71) Applicant: DUKE UNIVERSITY, Durham, NC (US)

(72) Inventors: Pei Zhou, Durham, NC (US); Jiyong Hong, Durham, NC (US)

(73) Assignee: Duke University, Durham, NC (US)

( * ) Notice: Subject to any disclaimer, the term of this patent is extended or adjusted under 35 U.S.C. 154(b) by 286 days.

(21) Appl. No.: 17/283,461

(22) PCT Filed: Oct. 9, 2019

(86) PCT No.: PCT/US2019/055481
§ 371 (c)(1),
(2) Date: Apr. 7, 2021

(87) PCT Pub. No.: WO2020/077014
PCT Pub. Date: Apr. 16, 2020

(65) Prior Publication Data
US 2022/0008408 A1 Jan. 13, 2022

Related U.S. Application Data

(60) Provisional application No. 62/743,004, filed on Oct. 9, 2018.

(51) Int. Cl.
A61K 31/4706 (2006.01)
A61K 33/243 (2019.01)
A61P 35/04 (2006.01)
A61P 35/00 (2006.01)

(52) U.S. Cl.
CPC ........ A61K 31/4706 (2013.01); A61K 33/243 (2019.01); A61P 35/00 (2018.01); A61P 35/04 (2018.01)

(58) Field of Classification Search
None
See application file for complete search history.

(56) References Cited

U.S. PATENT DOCUMENTS

| 2003/0017573 A1 | 1/2003 | Friedberg et al. |
| 2010/0120849 A1 | 5/2010 | Chung et al. |
| 2012/0046186 A1 | 2/2012 | Pelham et al. |
| 2013/0177546 A1 | 7/2013 | Hoelz |
| 2016/0038455 A1 | 2/2016 | Gill et al. |

FOREIGN PATENT DOCUMENTS

| WO | 2008102932 A1 | 8/2008 |
| WO | 2011137320 A2 | 11/2011 |
| WO | 2012093741 A1 | 7/2012 |
| WO | 2018074880 A2 | 4/2018 |
| WO | 2018190511 A1 | 10/2018 |

OTHER PUBLICATIONS

Pubchem, Substance Record for SID 160693684. Available Date: Feb. 4, 2013 (retrieved on Nov. 15, 2019).
International Search Report and Written Opinion dated Feb. 14, 2020 for International Patent Application No. PCT/US2019/055481.
Actis M.L., et al., "Identification of the First Small-Molecule Inhibitor of the REV7 DNA Repair Protein Interaction," Bioorganic & Medicinal Chemistry, Sep. 15, 2016, vol. 24, No. 18, pp. 4339-4346.
Adams P.D., et al., "PHENIX: Building New Software for Automated Crystallographic Structure De-Termination," Acta Crystallographica Section D: Structural Biology, Nov. 2002, vol. 58, No. 11, pp. 1948-1954.
Avkin S., et al., "Quantitative Analysis of Translesion DNA Synthesis Across a Benzo[a]Pyrene-Guanine Adduct in Mammalian Cells: The Role of DNA Polymerase Kappa," The Journal of Biological Chemistry, Dec. 17, 2004, vol. 279, No. 51, pp. 53298-53305.
Baranovskiy A.G., et al., "DNA Polymerase Delta and Zeta Switch by Sharing Accessory Subunits of DNA Polymerase Delta," The Journal of Biological Chemistry, May 18, 2012, vol. 287, No. 21, pp. 17281-17287.
Bhat A., et al., "Rev7/Mad2B Plays a Critical Role in the Assembly of a Functional Mitotic Spindle," Cell Cycle, 2015, vol. 14, No. 24, pp. 3929-3938.
Boersma V., et al., "MAD2L2 Controls DNA Repair at Telomeres and DNA Breaks by Inhibiting 5' End Resection," Nature, May 28, 2015, vol. 521, No. 7553, pp. 537-540.
Choi E.B., et al., "Synthesis of β-Lactam From Acyl(Arylcarbamoyl)-S,S-Bis(Alkylketene) Dithioacetal: Revised Structure of the Product from Thermal Cyclization of Acyl(Arylcarbamoyl)-S, S-Bis(Alkylketene) Dithioacetal," Synthesis, 2003, vol. 18, pp. 2771-2776.
Doles J., et al., "Suppression of Rev3, The Catalytic Subunit of Pol{Zeta}, Sensitizes Drug Resistant Lung Tumors to Chemotherapy," Proceedings of the National Academy of Sciences of the United States of America, Nov. 30, 2010, vol. 107, No. 48, pp. 20786-20791.
Emsley P., et al., "Coot: Model-building Tools for Molecular Graphics," Acta crystallographica Section D, Biological crystallography 60, Aug. 4, 2004, pp. 2126-2132.
Faustino-Rocha A., et al., "Estimation of Rat Mammary Tumor Volume Using Caliper and Ultrasonog-Raphy Measurements," Lab Animal (NY), Jun. 2013, vol. 42, No. 6, pp. 217-224.
Hashimoto K., et al., "The Vital Role of Polymerase Zeta and REV1 in Mutagenic, But not Correct, DNA Synthesis Across Benzo[A]Pyrene-Dg and Recruitment of Polymerase Z by REV1 to Replication-Stalled Site," The Journal of Biological Chemistry, Mar. 16, 2012, vol. 287, No. 12, pp. 9613-9622.

(Continued)

Primary Examiner — My-Chau T. Tran
(74) Attorney, Agent, or Firm — POLSINELLI PC

(57) ABSTRACT

This invention relates to compounds, pharmaceutical compositions comprising them, and methods of using the compounds and compositions for treating diseases related to translesion synthesis (TLS) pathway. More particularly, this disclosure relates to small molecule inhibitors of TLS, methods of inhibiting TLS pathway with these compounds, and methods of treating diseases related to the TLS pathway.

20 Claims, 21 Drawing Sheets
Specification includes a Sequence Listing.

(56) References Cited

OTHER PUBLICATIONS

Izuta S., "Inhibition of DNA Polymerase Eta by Oxetanocin Derivatives," Nucleic Acids Symposium Series, 2006, vol. 50, pp. 269-270.

Jansen J.G., et al., "Strand-Biased Defect in C/G Transversions in Hypermutating Immunoglobulin Genes in Rev1-Deficient Mice," Journal of Experimental Medicine, Feb. 20, 2006, vol. 203, No. 2, pp. 319-323.

Johnson R. E., et al., "Pol31 and Pol32 Subunits of Yeast DNA Polymerase Delta Are Also Essential Subunits of DNA Polymerase Zeta," Proceedings of the National Academy of Sciences of the United States of America, Jul. 31, 2012, vol. 109, No. 31, pp. 12455-12460.

Kabsch W., "XDS," Acta Crystallographica Section D: Structural Biology, Feb. 2010, vol. 66, No. 2, pp. 125-132.

Makarova A.V., et al., "A Four-Subunit DNA Polymerase Zeta Com-Plex Containing Pol Delta Accessory Subunits is Essential for PCNA-Mediated Mutagenesis," Nucleic Acids Research, Dec. 2012, vol. 40, No. 22, pp. 11618-11626.

Makarova A.V., et al., "Eukaryotic DNA Polymerase Zeta," DNA Repair (Amst), May 2015, vol. 29, pp. 47-55.

McCulloch S.D., et al., "Enzymatic Switching for Efficient and Accurate Translesion DNA Replication," Nucleic Acids Research, Aug. 27, 2004, vol. 32, No. 151, pp. 4665-4675.

Mizushina Y., et al., "3-O-Methylfunicone, a Selective Inhibitor of Mammalian Y-Family DNA Poly-Merases from an Australian Sea Salt Fungal Strain," Marine Drugs, Nov. 23, 2009, vol. 7, No. 4, pp. 624-639.

Mochizuki Y., et al., "Application of Coomassie Brilliant Blue Staining to Cultured Hepato-Cytes," Cell Biology International Reports, May 1987, vol. 11, No. 5, pp. 367-371.

Pak C.S., et al., "Aminolysis of 5-Acyl-2,2-Dimethyl-1,3-Dioxane 4,6-Diones (Acyl Meldrum's Acids) as a Versatile Method for the Synthesis of β-Oxo Carboxamides," Synthesis, 1992, vol. 1992, No. 12, pp. 1213-1214.

Sail V., et al., "Identification of Small Molecule Translesion Synthesis Inhibitors that Target the Rev1-CT/RIR Protein-Protein Interaction," ACS Chemical Biology, Jul. 21, 2017, vol. 12, No. 7, pp. 1903-1912.

Shachar S., et al., "Two-Polymerase Mechanisms Dictate Error-Free and Error-Prone Translesion DNA Synthesis in Mammals," The EMBO Journal, Feb. 18, 2009, vol. 28, No. 4, pp. 383-393.

Silva M.J., et al., "Comparative Analysis of the Mutagenic Activity of Oxaliplatin and Cisplatin in the Hprt Gene of CHO Cells," Environmental and Molecular Mutagenesis, Aug. 2005, vol. 46, No. 2, pp. 104-115.

Tang Q., et al., "Characterization of Byproducts from Chemical Syntheses of Oligonucleotides Con-Taining 1-Methyladenine and 3-Methylcytosine," ACS Omega, 2017, vol. 2, No. 11, pp. 8205-8212.

Vaisman A., et al., "Effect of DNA Polymerases and High Mobility Group Protein 1 on the Carrier Lig- and Specificity for Translesion Synthesis Past Platinum-DNA Adducts," Biochemistry, Aug. 24, 1999, vol. 38, No. 34, pp. 11026-11039.

Vaisman A., et al., "Translesion DNA Polymerases in Eukaryotes: What Makes Them Tick?," Critical Reviews in Biochemistry and Molecular Biology, Jun. 2017, vol. 52, No. 3, pp. 274-303.

Vanarotti M., et al., "Small-Molecules that Bind to the Ubiquitin-Binding Motif of REV1 Inhibit REV1 Interaction with K164-Monoubiquitinated PCNA and Suppress DNA Damage Tolerance," Bioorganic & Medicinal Chemistry, May 15, 2018, vol. 26, No. 9, pp. 2345-2353.

Wojtaszek J., et al., "Multifaceted Recognition of Vertebrate Rev1 by Translesion Polymerases Zeta and Kappa," The Journal of Biological Chemistry, Jul. 27, 2012, vol. 287, No. 31, pp. 26400-26408.

Wojtaszek J., et al., "Structural Basis of Rev1-Mediated Assembly of a Quaternary Vertebrate Trans-Lesion Polymerase Complex Consisting of Rev1, Heterodimeric Polymerase (Pol) zeta, and Pol kap-pa," The Journal of Biological Chemistry, Sep. 28, 2012, vol. 287, No. 40, pp. 33836-33846.

Wojtaszek J.L., et al., "A Small Molecule Targeting Mutagenic Translesion Synthesis Improves Chemotherapy," Cell, Jun. 27, 2019, vol. 178, No. 1, pp. 152-159.

Wojtaszek J.L., et al., "Ubiquitin Recognition by FAAP20 Expands the Complex Interface beyond the Canonical UBZ Domain," Nucleic Acids Research, Dec. 16, 2014, vol. 42, No. 22, pp. 13997-14005.

Xie K., et al., "Error-Prone Translesion Synthesis Mediates Ac-Quired Chemoresistance," Proceedings of the National Academy of Sciences of the United States of America, Nov. 30, 2010, vol. 107, No. 48, pp. 20792-20797.

Xu G., et al., "REV7 Counteracts DNA Double-Strand Break Resection and Affects PARP Inhibition," Nature, May 28, 2015, vol. 521, No. 7553, pp. 541-544.

Xu X., et al., "Enhancing Tumor Cell Response to Chemotherapy Through Nanoparticle Mediated Codelivery of siRNA and Cisplatin Prodrug," Proceedings of the National Academy of Sciences of the United States of America, Nov. 12, 2013, vol. 110, No. 46, pp. 18638-18643.

Yamanaka K., et al., "A Comprehensive Strategy to Discover Inhibitors of the Translesion Synthesis DNA Polymerase kappa," PLoS One, 2012, vol. 7, No. 10, 8 pages.

Yamanaka K., et al., "Inhibition of Mutagenic Translesion Synthesis: A Possible Strategy for Improving Chemotherapy?," PLoS Genetics, Aug. 17, 2017, vol. 13, No. 8, 16 pages.

Yang W., et al., "Translesion and Repair DNA Polymerases: Diverse Structure and Mechanism," Annual Review of Biochemistry, Jun. 20, 2018, vol. 87, pp. 239-261.

Zhou P., et al., "A Solubility-Enhancement Tag (SET) for NMR Studies of Poorly Behaving Proteins," Journal of Biomolecular NMR, May 2001, vol. 20, pp. 11-14.

Ziv O., et al., "Quantitative Measurement of Trans-Lesion DNA Synthesis in Mammalian Cells," Methods in Molecular Biology, 2012, vol. 920, pp. 529-542.

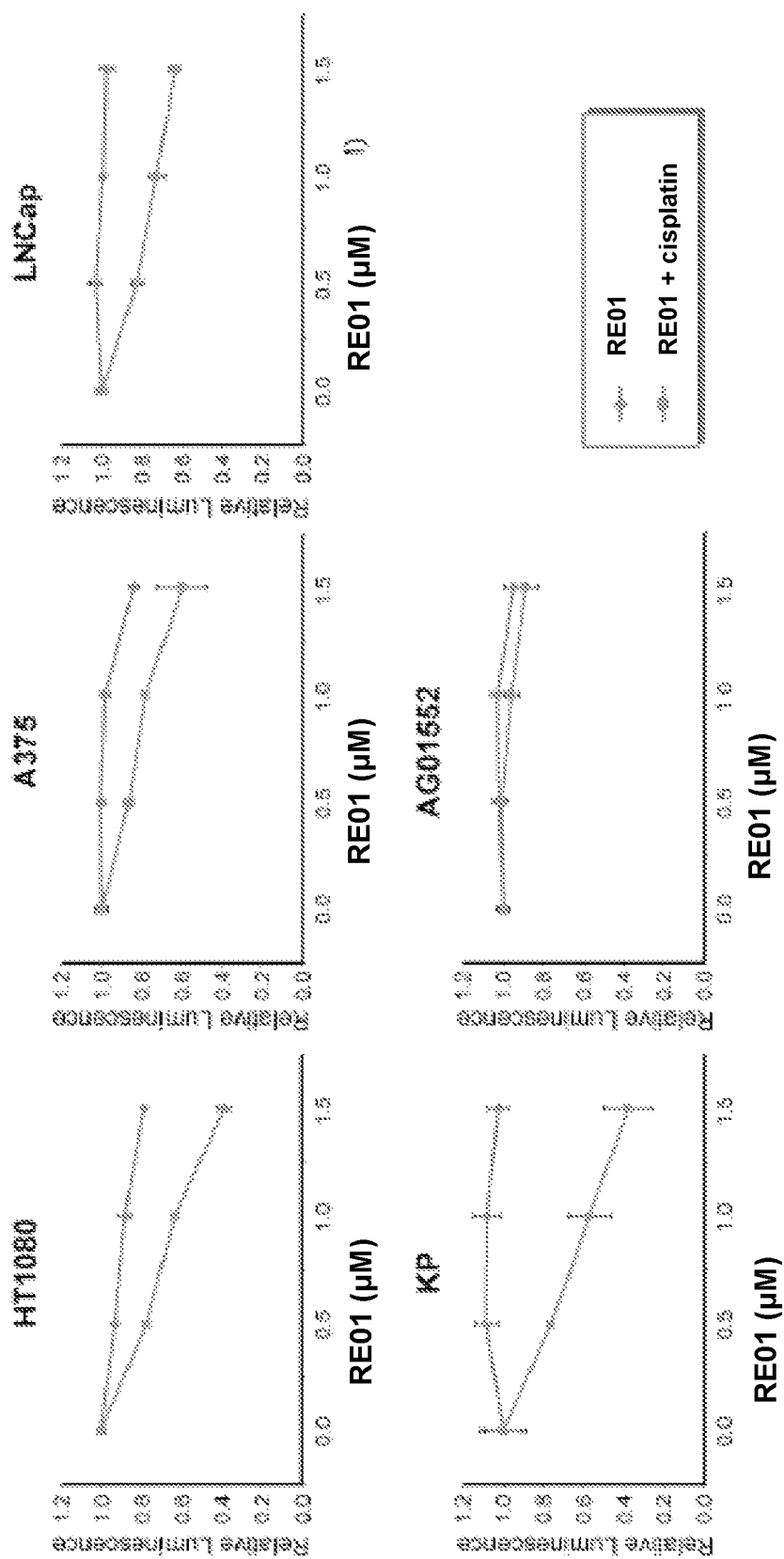

| Concentration (μM) | Bypass (%) DMSO | Bypass (%) RE01 | Inhibition (%) |
|---|---|---|---|
| 1.5 | 14.6 | 11.1 | 24.1 |
| 3.0 | 13.9 | 9.8 | 29.8 |
| 15.0 | 14.2 | 8.9 | 37.6 |

SEQUENCE LISTING

<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: oligonucleotide containing a 1,2-GG sequence

<400> SEQUENCE: 1
ctctctcggc cttcta                                              16

<210> SEQ ID NO 2
<211> LENGTH: 21
<212> TYPE: DNA
<213> ORGANISM: Artificial Sequence
<220> FEATURE:
<223> OTHER INFORMATION: oligonucleotide flanking the cisplatin-
      containing oligonucleotide

<400> SEQUENCE: 2
gcccgtcgta gcgcgcatgc a                                        21

<210> SEQ ID NO 3
<211> LENGTH: 21
<212> TYPE: DNA
<213> ORGANISM: Artificial Sequence
<220> FEATURE:
<223> OTHER INFORMATION: oligonucleotide flanking the cisplatin-
      containing oligonucleotide

<400> SEQUENCE: 3
tctcgagtgt tccgtcagca c                                        21

<210> SEQ ID NO 4
<211> LENGTH: 18
<212> TYPE: DNA
<213> ORGANISM: Artificial Sequence
<220> FEATURE:
<223> OTHER INFORMATION: pUC19 plasmid-modifying oligonucleotide

<400> SEQUENCE: 4
tgcatgcgcg ctacgacg                                            18

<210> SEQ ID NO 5
<211> LENGTH: 24
<212> TYPE: DNA
<213> ORGANISM: Artificial Sequence
<220> FEATURE:
<223> OTHER INFORMATION: pUC19 plasmid-modifying oligonucleotide

<400> SEQUENCE: 5
agcgtgctga cggaacactc gaga                                     24

<210> SEQ ID NO 6
<211> LENGTH: 19
<212> TYPE: DNA
<213> ORGANISM: Artificial Sequence
<220> FEATURE:
<223> OTHER INFORMATION: oligonucleotide  for competitor gapped plasmid

<400> SEQUENCE: 6
ctctctaggc tcacttcta                                           19

<210> SEQ ID NO 7
<211> LENGTH: 26

```
<212> TYPE: DNA
<213> ORGANISM: Artificial Sequence
<220> FEATURE:
<223> OTHER INFORMATION: forward primer for PCR amplification of
      cisplatin lesion

<400> SEQUENCE: 7
ttgtactgag agtgcaccat gcccgt                                          26

<210> SEQ ID NO 8
<211> LENGTH: 26
<212> TYPE: DNA
<213> ORGANISM: Artificial Sequence
<220> FEATURE:
<223> OTHER INFORMATION: reverse primer for PCR amplification of
      cisplatin lesion

<400> SEQUENCE: 8
gagtcagtga gcgaggaagc gtgctg                                          26

<210> SEQ ID NO 9
<211> LENGTH: 22
<212> TYPE: DNA
<213> ORGANISM: Artificial Sequence
<220> FEATURE:
<223> OTHER INFORMATION: forward p21 primer

<400> SEQUENCE: 9
gtcactgtct tgtacccttg tg                                              22

<210> SEQ ID NO 10
<211> LENGTH: 21
<212> TYPE: DNA
<213> ORGANISM: Artificial Sequence
<220> FEATURE:
<223> OTHER INFORMATION: reverse p21 primer

<400> SEQUENCE: 10
cggcgtttgg agtggtagaa a                                               21

<210> SEQ ID NO 11
<211> LENGTH: 21
<212> TYPE: DNA
<213> ORGANISM: Artificial Sequence
<220> FEATURE:
<223> OTHER INFORMATION: forward GAPDH primer

<400> SEQUENCE: 11
ggagcgagat ccctccaaaa t                                               21

<210> SEQ ID NO 12
<211> LENGTH: 23
<212> TYPE: DNA
<213> ORGANISM: Artificial Sequence
<220> FEATURE:
<223> OTHER INFORMATION: reverse GAPDH primer

<400> SEQUENCE: 12
ggctgttgtc atacttctca tgg                                             23
```

COMPOSITIONS AND METHODS FOR ADJUVANT CANCER THERAPEUTICS

CROSS-REFERENCE TO RELATED APPLICATIONS

This application is a U.S. national phase application under 35 U.S.C. § 371 of International Application No. PCT/US2019/055481, filed on Oct. 9, 2019, which claims the benefit of priority to U.S. Provisional Patent Application No. 62/743,004, filed on Oct. 9, 2018, both of which are incorporated by reference herein in their entirety.

STATEMENT REGARDING FEDERALLY SPONSORED RESEARCH OR DEVELOPMENT

This invention was made with Government support under Federal Grant no. CA191448 awarded by the National Cancer Institute. The Federal Government has certain rights to this invention.

SEQUENCE LISTING

This application contains a Sequence Listing that has been submitted in ASCII format via EFS-Web and is hereby incorporated by reference in its entirety. The ASCII copy was created on Oct. 9, 2019 is named 19-1868-WO_ST25.txt, and is 3 kilobytes in size.

BACKGROUND OF DISCLOSURE

Field of Invention

This invention relates to compounds, pharmaceutical compositions comprising them, and methods of using the compounds and compositions for treating diseases related to translesion synthesis (TLS) pathway. More particularly, this disclosure relates to small molecule inhibitors of TLS, methods of inhibiting TLS pathway with these compounds, and methods of treating diseases related to the TLS pathway.

Technical Background

DNA-damaging chemotherapeutics, such as cisplatin, have been the mainstay of cancer treatment for decades. DNA lesions generated by these therapies cannot be utilized by high-fidelity replicative DNA polymerases as the template, thus blocking the progression of the replication fork, generating cytotoxicity, and ultimately causing cell death. To promote survival, cells employ specialized DNA polymerases to bypass the lesion site at the cost of replication fidelity in a process known as translesion synthesis (TLS). In mammalian cells, TLS occurs in a two-step process in which insertion TLS DNA polymerases such as POL $_\kappa$, POL $_\iota$, POL $_\eta$, or REV1 first introduce a nucleotide opposite the lesion. This is followed by elongation of the resulting 3'-terminus by an extension TLS DNA polymerase such as the B-family polymerase complex POL $\zeta$ (POL $\zeta_4$: REV3L/REV7/POLD2/POLD3). While TLS carried out by certain insertion DNA polymerases over their cognate lesions can be relatively accurate, for example POL $_\eta$ over a cyclobutane thymine-thymine dimer, the major mutagenic branch of TLS is characterized by its dependence on REV1 and POL $\zeta$. The ca. 100 amino acid REV1 C-terminal domain (CTD) plays a major role in coordinating TLS, using one interface to recruit the insertion TLS polymerases POL $_\kappa$, POL $_\iota$, POL $_\eta$ and a second interface to recruit POL $\zeta$ through an interaction with its REV7 component. It has been found that genetic inhibition of TLS through RNA-mediated depletion of REV1 or REV3L, the catalytic subunit of mammalian POL $\zeta$, sensitizes a variety of cancer cells to DNA-damaging chemotherapeutics and suppresses the emergence of new tumor chemoresistance in vitro and in vivo, thereby highlighting the therapeutic potential of inhibiting the REV1-POL $\zeta$ mediated TLS in cancer therapy.

Although small molecule compounds interfering with aspects of TLS have been reported, none has yet been shown to demonstrate in vivo efficacy. Therefore, there exists need in the art for novel and improved small molecule inhibitors of TLS.

SUMMARY OF THE DISCLOSURE

One aspect of the disclosure provides methods of treating cancer. Such methods include administering to a subject in need thereof (i) one or more secondary therapeutic agents and (ii) one or more compounds of formula (I),

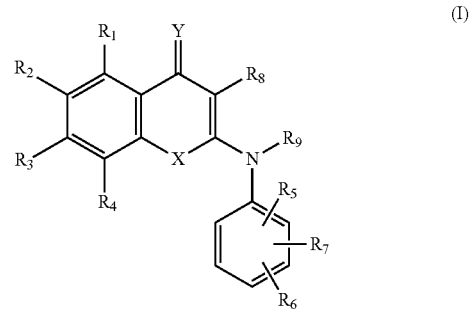

or a pharmaceutically acceptable salt thereof, wherein
X and Y are independently selected from NR, O, or S, where R is hydrogen or $C_1$-$C_4$ alkyl;
$R_1$, $R_2$, $R_3$, and $R_4$ are independently selected from the group consisting of hydrogen, halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl)$_2$, —$CO_2H$, —$CO_2$($C_1$-$C_6$ alkyl), —CHO, —CO($C_1$-$C_6$ alkyl), and —S(O)$_{0-2}$($C_1$-$C_6$ alkyl);
$R_5$, $R_6$, and $R_7$ are independently selected from the group consisting of hydrogen, halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —$CONH_2$, —CONH($C_1$-$C_6$ alkyl), —CON($C_1$-$C_6$ alkyl)$_2$, —$CO_2H$, —$CO_2$($C_1$-$C_6$ alkyl), —CHO, —CO($C_1$-$C_6$ alkyl), and —S(O)$_{0-2}$($C_1$-$C_6$ alkyl),
or $R_5$ and $R_6$, together with the atoms to which they are attached, form a 5 or 6 membered aryl, heteroaryl, or heterocyclyl;
$R^8$ is $C_1$-$C_8$ alkyl optionally substituted with one or more $R_{10}$, $C_2$-$C_8$ alkenyl optionally substituted with one or more $R_{10}$, or $C_2$-$C_8$ alkynyl optionally substituted with one or more $R_{10}$,
wherein each $R_{10}$ is independently selected from the group consisting of halogen, —$NO_2$, —CN, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CONH($C_1$-$C_6$ alkyl), —CON($C_1$-$C_6$ alkyl)$_2$, —$CO_2H$, —$CO_2$($C_1$-$C_6$ alkyl), —CHO, —CO($C_1$-$C_6$ alkyl), and —S(O)$_{0-2}$($C_1$-$C_6$ alkyl), or two $R_{10}$ groups when attached to the same carbon atom form =O, =NR, or =N—OH; and $R^9$ is hydrogen or $C_1$-$C_4$ alkyl.

Another aspect of the disclosure provides methods of improving activity of one or more secondary therapeutic agents as described herein. Such methods include administering to a subject in need thereof an effective dose of one or more compounds of formula (I) as described herein.

Another aspect of the disclosure provides methods of inhibiting translesion synthesis (TLS) pathway in a subject. Such methods include administering to a subject in need thereof an effective dose of one or more compounds of formula (I) as described herein.

Another aspect of the disclosure provides compounds of formula (I). In certain embodiments, the compounds of formula (I) are those listed in Table 1. In certain embodiments, the compounds of formula (I) are those listed in Table 2.

Additional aspects of the disclosure will be evident from the disclosure herein.

BRIEF DESCRIPTION OF THE DRAWINGS

The accompanying drawings are included to provide a further understanding of the compositions and methods of the disclosure, and are incorporated in and constitute a part of this specification. The drawings illustrate one or more embodiment(s) of the disclosure and, together with the description, serve to explain the principles and operation of the disclosure.

FIG. 9A is a graph showing relative survivability with increasing doses of RE01 in cisplatin-treated cells.

DETAILED DESCRIPTION

Figure 1A:
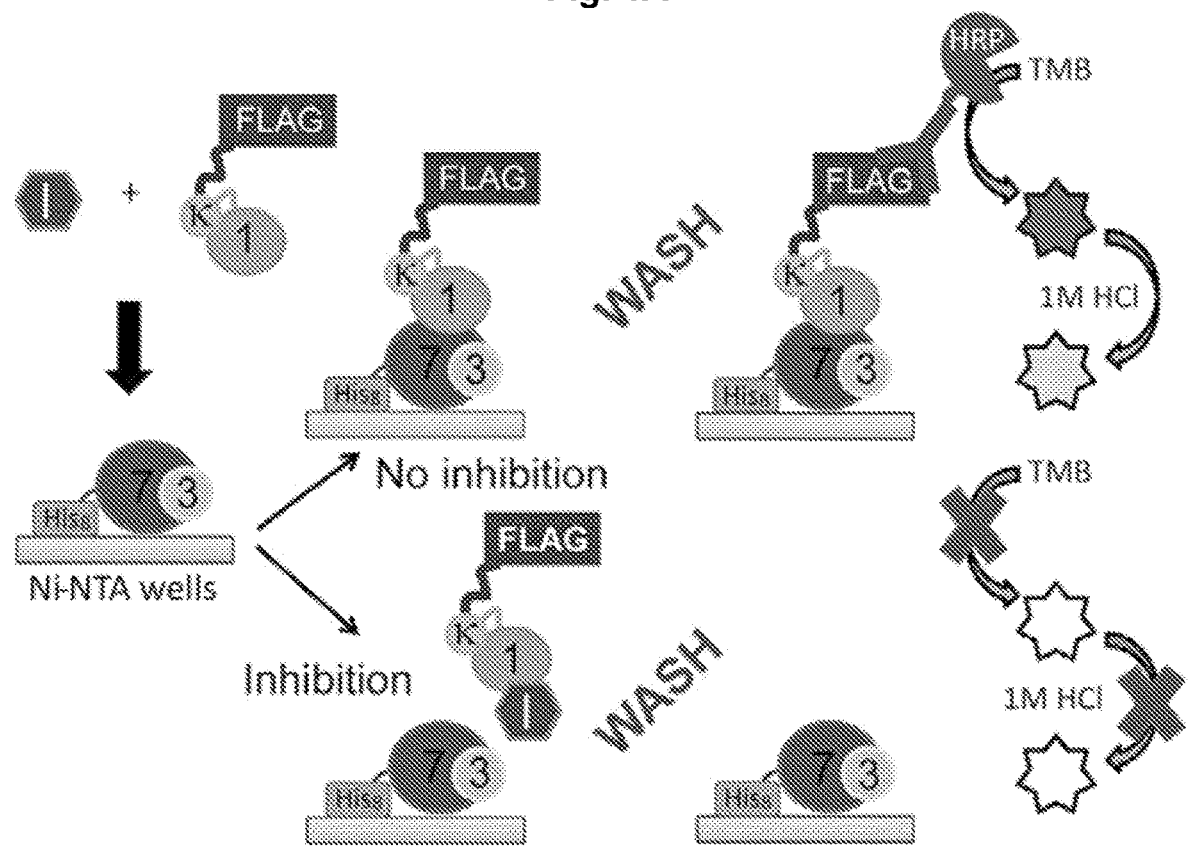
FIG. 1A is an illustration depicting an overview of the ELISA assay described in Example 16.

Before the disclosed processes and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. In general, the disclosed materials and methods provide improvements in treatment of cancer and are based, in part, on the discovery by the inventors of the first in vivo active small molecule inhibitor of TLS. Obtaining a specific inhibitor of mutagenic TLS is inherently challenging since TLS and replicative polymerases share both common substrates and interaction partners (e.g. PCNA), and some components of TLS DNA polymerases, such as REV7, are additionally implicated in cellular functions beyond translesion synthesis. The inventors, however, recognized that the evolutionarily conserved interaction between REV1 and POL ζ, mediated by a shallow pocket on the REV1 CTD and the REV7 subunit of POL ζ, plays a critical and specific role in mutagenic TLS, but not accurate lesion bypass, rendering such a protein-protein interaction an ideal target for small molecule intervention.

The inventors designed an ELISA assay to screen for small molecule inhibitors that specifically target the REV7-binding surface of the REV1 CTD to disrupt the REV1-REV7 interaction. The inventors discovered RE01, which is active in vivo, that selectively disrupts mutagenic TLS by preventing the Rev1 CTD from recruiting Pol zeta via an interaction with its Rev7 component. Remarkably, RE01 interacts asymmetrically with the Rev7-binding pockets of two Rev1 CTDs to cause dimerization. The inventors have shown that RE01 inhibits mutagenic TLS and enhances cisplatin-induced-toxicity in cultured tumor cell lines over normal tissues, in a fashion that validates Rev1 as the primary drug target. Further, the inventors have also shown that co-administration of RE01 with cisplatin strikingly suppresses the growth of xenograft human melanomas in mice, establishing a framework for developing TLS inhibitors as a novel class of chemotherapy adjuvants.

Thus, one aspect of the disclosure provides methods of inhibiting TLS pathway in a subject. Another aspect of the disclosure provides methods of treating cancer.

As is known in the art, a cancer is generally considered as uncontrolled cell growth. The methods of the present invention can be used to treat any cancer, and any metastases thereof, including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma, fibrosarcoma, and peripheral neuroepithelioma. In some embodiments, the cancer is a metastatic cancer. In certain embodiments, the cancer is treatment-resistant cancer or relapsed cancer (i.e., treatment-resistant tumors or relapsed tumors).

In certain embodiments of the method of the disclosure, the cancer comprises melanoma. In certain embodiments of the method of the disclosure, the cancer is lung cancer. In certain embodiments of the method of the disclosure, the cancer is prostate cancer. In certain embodiments of the method of the disclosure, the cancer is fibrosarcoma.

The methods of the disclosure as described herein include administering to a subject in need of such treatment an effective amount of one or more compounds of the disclosure (i.e., compounds of formula (I)). In certain embodiments, the method also includes administering a secondary therapeutic agent.

In certain embodiments of the method of the disclosure, the secondary therapeutic agent is a chemotherapeutic reagent. As used herein, the term "chemotherapeutic agent" as employed herein is intended to refer to specific antineoplastic chemical agents or drugs that are "selectively" destructive to malignant cells and tissues. Chemotherapeutic agents are well known in the art and include, for example, alkylating antineoplastic agents, antimetabolites including thymidylate synthase inhibitors, anthracyclines, anti-microtubule agents including plant alkaloids, topoisomerase inhibitors, parp inhibitors and other antitumor agents.

Examples of alkylating agents, which may be employed in the method of the present disclosure, include an alkylating agent nitrogen mustards, nitrosoureas, tetrazines, aziridines, platins and derivatives, and non-classical alkylating agents. Example a platinum containing chemotherapeutic agent (also referred to as platins), such as cisplatin, carboplatin, oxaliplatin, satraplatin, picoplatin, nedaplatin, triplatin and lipoplatin (a liposomal version of cisplatin). Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Examples of antimetabolites, which may be employed in the method of the present disclosure, include anti-folates (for example methotrexate and pemetrexed), purine analogues (for example thiopurines, such as azathiopurine, mercaptopurine, thiopurine, fludarabine (including the phosphate form), pentostatin and cladribine), pyrimidine analogues (for example fluoropyrimidines, such as 5-fluorouracil and prodrugs thereof such as capecitabine [Xeloda®]), floxuridine, gemcitabine, cytarabine, decitabine, raltitrexed (tomudex) hydrochloride, cladribine and 6-azauracil. Examples of anthracyclines, which may be employed in the method of the present disclosure, include daunorubicin (Daunomycin), daunorubicin (liposomal), doxorubicin (Adriamycin), doxorubicin (liposomal), epirubicin, idarubicin, valrubicin currently used only to treat bladder cancer and mitoxantrone an anthracycline analog, in particular doxorubicin. Examples of anti-microtubule agents, which may be employed in the method of the present disclosure, include include vinca alkaloids and taxanes. Vinca alkaloids include completely natural chemicals for example vincristine and vinblastine and also semi-synthetic vinca alkaloids, for example vinorelbine, vindesine, and vinflunine Taxanes include paclitaxel, docetaxel, abraxane, carbazitaxel and derivatives of thereof. Derivatives of taxanes as employed herein include reformulations of taxanes like taxol, for example in a micelluar formulaitons, derivatives also include chemical derivatives wherein synthetic chemistry is employed to modify a starting material which is a taxane.

Topoisomerase inhibitors, which may be employed in a method of the present disclosure include type I topoisomerase inhibitors, type II topoisomerase inhibitors and type II topoisomerase poisons. Type I inhibitors include topotecan, irinotecan, indotecan and indimitecan. Type II poisons include amsacrine, etoposide, etoposide phosphate, teniposide and doxorubicin and fluoroquinolones.

In certain embodiments of the method of the disclosure, the secondary therapeutic agent is an alkylating antineoplastic agent. For example, in certain embodiments, the alkylating antineoplastic agent is a platinum-based antineoplastic agent, such as cisplatin, carboplatin, oxaliplatin, nedaplatin, satraplatin, picoplatin, tetraplatin, and lipoplatin.

In certain embodiments of the method of the disclosure, the one or more secondary therapeutic agents is cisplatin.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Combination therapy, in defining use of a compound of the present disclosure and the secondary therapeutic agent, is intended to embrace administration of each agent in a sequential manner in a regimen that will provide beneficial effects of the drug combination (e.g., the compounds and compositions of the disclosure as described herein and the secondary therapeutic agents can be formulated as separate compositions that are given sequentially), and is intended as well to embrace co-administration of these agents in a substantially simultaneous manner, such as in a single capsule having a fixed ratio of these active agents or in multiple or a separate capsules for each agent. The disclosure is not limited in the sequence of administration: the compounds of and compositions of the disclosure may be administered either prior to or after (i.e., sequentially), or at the same time (i.e., simultaneously) as administration of the secondary therapeutic agent.

In certain embodiments, the secondary therapeutic agent may be administered in an amount below its clinically established half maximal inhibitory concentration ($IC_{50}$) when administered alone. For example, the secondary therapeutic agent may be administered in an amount less than 10% of, e.g., less than 20%, or less than 25%, or less than 50%, or less than 75%, or even less than 90% of the inhibitory concentration ($IC_{50}$). Thus, one aspect of the disclosure provides methods of improving activity of one or more secondary therapeutic agents as described herein.

The dose for cisplatin ranges from about 20 to about 270 mg/m² depending on the exact cancer. Often the dose is in the range about 70 to about 100 mg/m². In certain embodiments, wherein the effective dose of the one or more compounds of formula (I) is sufficient to provide cisplatin in a dose lower than the dose required to provide the same activity when administered without the one or more compounds of formula (I). For example, in certain embodiments, the cisplatin dose is lower by at least 10%, for example, lower by at least 20%, 25%, 50%, 75%, or lower by at least 90% (based on the mg/m² concentration).

Compounds

The disclosure provides compounds of formula (I) as provided above.

Particularly useful compounds of formula (I) are those wherein X is NR or O. In certain embodiments, such compounds are those wherein X is NR. In certain embodiments, X is NH.

Other particularly useful compounds of formula (I) are those wherein Y is NR or O. In certain embodiments, such compounds are those wherein Y is O.

Other particularly useful compounds of formula (I) are those wherein $R_9$ is hydrogen or —$CH_3$. In certain embodiments, such compounds are those where $R_9$ is hydrogen. In certain embodiments of the disclosure, the compound of formula (I) as otherwise described herein are of formula:

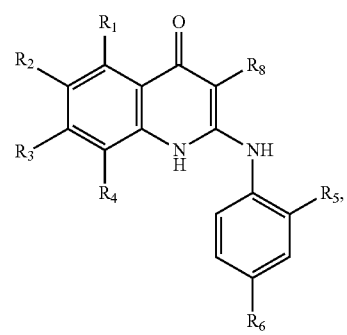

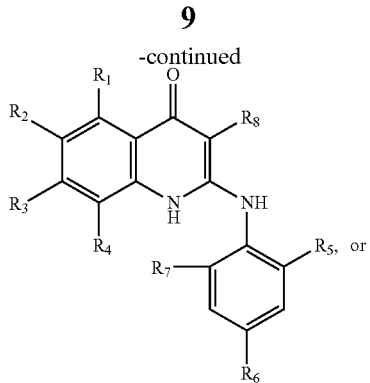

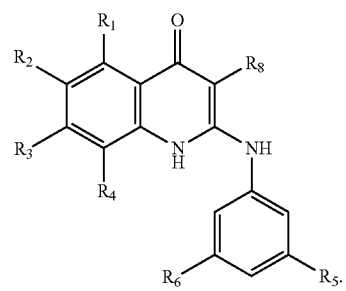

One embodiment of the disclosure provides compounds of formula (I) as otherwise described herein where $R_1$ is hydrogen, halogen, —$NO_2$, —CN, $C_1$-$C_6$ alkyl, $C_1$-$C_6$ haloalkyl, —OH, $C_1$-$C_6$ alkoxy, $C_1$-$C_6$ haloalkoxy, —$CO_2H$, or —$CO_2(C_1$-$C_6$ alkyl). In certain embodiments, $R_1$ is hydrogen, —F, —Cl, —Br, —$NO_2$, —CN, $C_1$-$C_3$ alkyl, $C_1$-$C_3$ haloalkyl, —OH, $C_1$-$C_3$ alkoxy, $C_1$-$C_3$ haloalkoxy, —$CO_2H$, or —$CO_2(C_1$-$C_3$ alkyl). In certain embodiments, $R_1$ is hydrogen, —F, —Cl, —Br, —$NO_2$, —$CH_3$, —$CF_3$, —OH, —$OCH_3$, —$OCF_3$, —$CO_2H$, or —$CO_2CH_3$. In certain embodiments, $R_1$ is —$NO_2$.

Another embodiment of the disclosure provides compounds of formula (I) as otherwise described herein wherein $R_2$ is hydrogen or —$NO_2$. In certain embodiments, $R_2$ is hydrogen.

Another embodiment of the disclosure provides compounds of formula (I) as otherwise described herein wherein $R_3$ is hydrogen or —$NO_2$. In certain embodiments, $R_3$ is hydrogen.

One embodiment of the disclosure provides compounds of formula (I) as otherwise described herein where $R_4$ is hydrogen, halogen, —$NO_2$, —CN, $C_1$-$C_6$ alkyl, $C_1$-$C_6$ haloalkyl, —OH, $C_1$-$C_6$ alkoxy, $C_1$-$C_6$ haloalkoxy, —$CO_2H$, or —$CO_2(C_1$-$C_6$ alkyl). In certain embodiments, $R_4$ is hydrogen, —F, —Cl, —Br, —$NO_2$, —CN, $C_1$-$C_3$ alkyl, $C_1$-$C_3$ haloalkyl, —OH, $C_1$-$C_3$ alkoxy, $C_1$-$C_3$ haloalkoxy, —$CO_2H$, or —$CO_2(C_1$-$C_3$ alkyl). In certain embodiments, $R_4$ is hydrogen, —F, —Cl, —Br, —$NO_2$, —$CH_3$, —$CF_3$, —OH, —$OCH_3$, —$OCF_3$, —$CO_2H$, or —$CO_2CH_3$. In certain embodiments, $R_4$ is hydrogen, —F, —Cl, or —Br. In certain embodiments, $R_4$ is hydrogen. In certain embodiments, $R_4$ is —F, —Cl, or —Br. In certain embodiments, $R_4$ is —Cl.

In certain embodiments of the disclosure, the compound of formula (I) as otherwise described herein is wherein $R_1$ is —$NO_2$, $R_2$ is hydrogen, $R_3$ is hydrogen, and $R_4$ is —Cl. Such compounds are of formula:

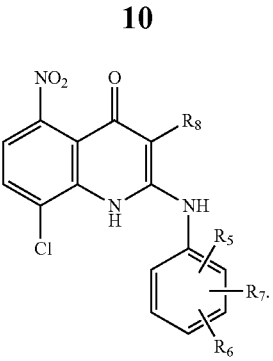

In certain embodiments such compounds are of formula:

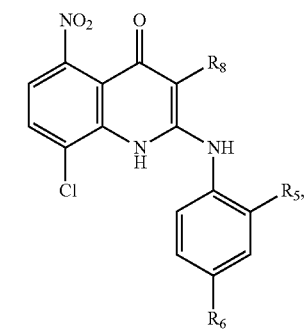

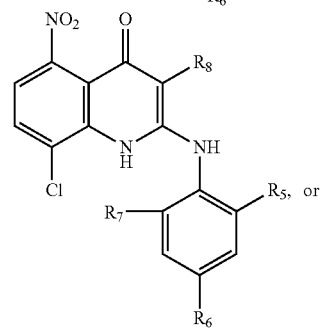

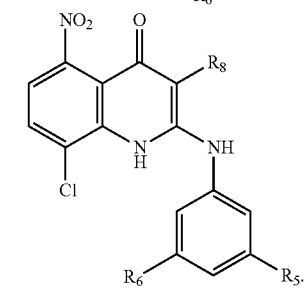

Another embodiment of the disclosure provides compounds of formula (I) as otherwise described herein $R_5$ is hydrogen, halogen, —$NO_2$, —CN, $C_1$-$C_6$ alkyl, $C_1$-$C_6$ haloalkyl, —OH, $C_1$-$C_6$ alkoxy, $C_1$-$C_6$ haloalkoxy, —$CO_2H$, or —$CO_2(C_1$-$C_6$ alkyl). In some embodiments, $R_5$ is —F, —Cl, —Br, —$NO_2$, —CN, $C_1$-$C_3$ alkyl, $C_1$-$C_3$ haloalkyl, —OH, $C_1$-$C_3$ alkoxy, $C_1$-$C_3$ haloalkoxy, —$CO_2H$, or —$CO_2(C_1$-$C_3$ alkyl). In some embodiments, $R_5$ is —F, —Cl, —Br, —$NO_2$, —$CH_3$, —$CF_3$, —OH, —$OCH_3$, —$OCF_3$, —$CO_2H$, or —$CO_2CH_3$. In some embodiments, $R_5$ is —F, —Cl, or —Br. In some embodiments, $R_5$ is —Cl.

Another embodiment of the disclosure provides compounds of formula (I) as otherwise described herein $R_6$ is hydrogen, halogen, —$NO_2$, —CN, $C_1$-$C_6$ alkyl, $C_1$-$C_6$ haloalkyl, —OH, $C_1$-$C_6$ alkyl, $C_1$-$C_6$ haloalkoxy, —$CO_2H$, or —$CO_2$($C_1$-$C_6$ alkyl). In some embodiments, $R_6$ is —F, —Cl, —Br, —$NO_2$, —CN, $C_1$-$C_3$ alkyl, $C_1$-$C_3$ haloalkyl, —OH, $C_1$-$C_3$ alkoxy, $C_1$-$C_3$ haloalkoxy, —$CO_2H$, or —$CO_2$($C_1$-$C_3$ alkyl). In some embodiments, $R_6$ is —F, —Cl, —Br, —$NO_2$, —$CH_3$, —$CF_3$, —OH, —$OCH_3$, —$OCF_3$, —$CO_2H$, or —$CO_2CH_3$. In some embodiments, $R_6$ is —F, —Cl, or —Br. In some embodiments, $R_6$ is —Cl.

In some embodiments, $R_5$ and $R_6$ are independently —F, —Cl, —Br, —$NO_2$, —$CH_3$, —$CF_3$, —OH, —$OCH_3$, —$OCF_3$, —$CO_2H$, or —$CO_2CH_3$. In some embodiments, $R_5$ and $R_6$ are independently —F, —Cl, or —Br. In some embodiments, $R_5$ and $R_6$ are independently —Cl. In certain embodiments, $R_5$ and $R_6$ are the same. In certain embodiments, $R_5$ and $R_6$ are different.

In certain embodiments of the disclosure, the compound of formula (I) as otherwise described herein is wherein $R_7$ is —F, —Cl, —Br, —$NO_2$, —$CH_3$, —$CF_3$, —OH, —$OCH_3$, —$OCF_3$, —$CO_2H$, or —$CO_2CH_3$. In certain embodiments, $R_7$ is —F, —Cl, or —Br. In certain embodiments, $R_7$ is hydrogen. In certain embodiments, —Cl.

One embodiment of the disclosure provides compounds of formula (I) as otherwise described herein where $R^8$ is $C_1$-$C_8$ alkyl optionally substituted with one or more $R_{10}$ or $C_2$-$C_8$ alkenyl optionally substituted with one or more $R_{10}$. In certain embodiments, $R^8$ is $C_1$-$C_6$ alkyl optionally substituted with one or more $R_{10}$ or $C_2$-$C_6$ alkenyl optionally substituted with one or more $R_{10}$. In certain embodiments, $R^8$ is $C_1$-$C_8$ alkyl optionally substituted with one or more $R_{10}$. In certain embodiments, $R^8$ is $C_2$-$C_8$ alkanoyl (e.g., —C(O)($C_1$-$C_7$ alkyl)) optionally substituted with one or more $R_{10}$.

In some embodiments of the compounds of formula (I) as otherwise described herein, $R_{10}$ is —F, —Cl, —Br, —$NO_2$, —$CHF_2$, —$CF_3$, —OH, —$OCH_3$, —$OCF_3$, —$CO_2H$, or —$CO_2CH_3$.

One embodiment of the disclosure provides compounds of formula (I) as otherwise described herein where $R^8$ is unsubstituted $C_2$-$C_8$ alkanoyl. In certain embodiments, $R^8$ is unsubstituted $C_2$-$C_6$ alkanoyl, e.g. —C(O)($C_1$-$C_5$ alkyl).

One embodiment of the disclosure provides compounds of formula (I) as otherwise described herein where $R^8$ is selected from:

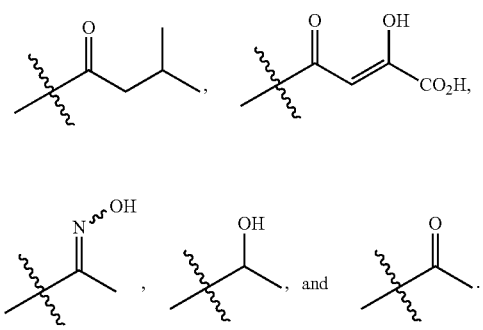

In certain embodiments, $R^8$ is

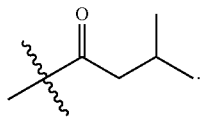 [SMILES: *C(=O)CC(C)C]

Particularly useful compounds of formula (I) are those provided in Table 1.

TABLE 1

| Compound Code | Structure | Compound Name |
| --- | --- | --- |
| RE01 | ![structure] | 8-chloro-2-((2,4-dichlorophenyl)amino)-3-(3-methylbutanoyl)-5-nitroquinolin-4(1H)-one |
| RE03 | ![structure] | 8-chloro-2-((2,3-dichlorophenyl)amino)-3-(3-methylbutanoyl)-5-nitroquinolin-4(1H)-one |

TABLE 1-continued

| Compound Code | Structure | Compound Name |
|---|---|---|
| RE04 | 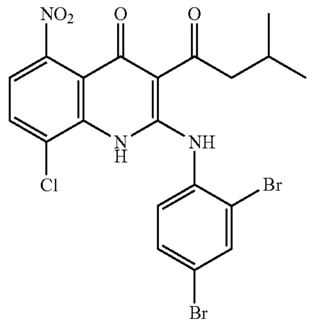 | 8-chloro-2-((2,4-dibromophenyl)amino)-3-(3-methylbutanoyl)-5-nitroquinolin-4(1H)-one |
| RE05 | 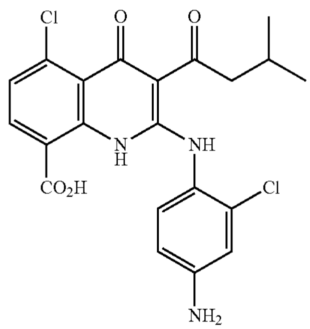 | 2-((4-amino-2-chlorophenyl)amino)-5-chloro-3-(3-methylbutanoyl)-4-oxo-1,4-dihydroquinoline-8-carboxylic acid |
| RE06 | 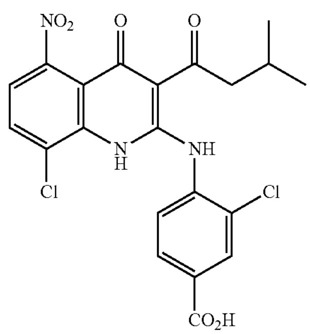 | 3-chloro-4-((8-chloro-3-(3-methylbutanoyl)-5-nitro-4-oxo-1,4-dihydroquinolin-2-yl)amino)benzoic acid |
| RE07 | 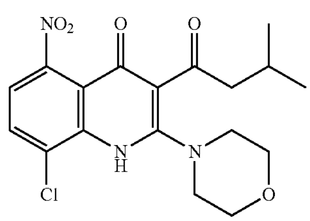 | 8-chloro-3-(3-methylbutanoyl)-2-morpholino-5-nitroquinolin-4(1H)-one |
| RE08 | 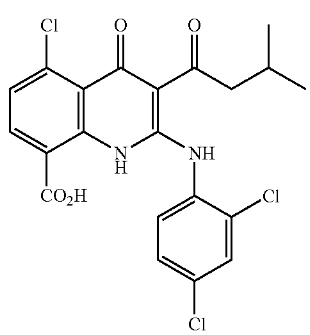 | 5-chloro-2-((2,4-dichlorophenyl)amino)-3-(3-methylbutanoyl)-4-oxo-1,4-dihydroquinoline-8-carboxylic acid |

TABLE 1-continued

| Compound Code | Structure | Compound Name |
|---|---|---|
| RE09 | 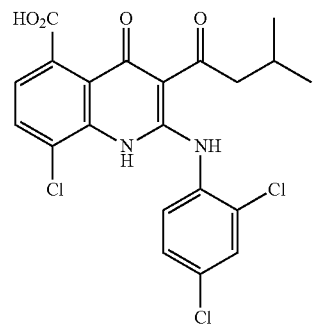 | 8-chloro-2-((2,4-dichlorophenyl)amino)-3-(3-methylbutanoyl)-4-oxo-1,4-dihydroquinoline-5-carboxylic acid |
| RE10 | 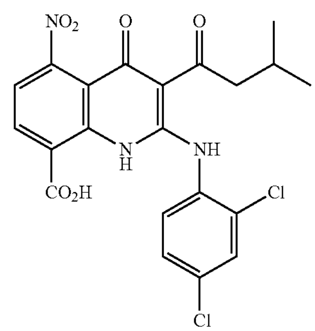 | 2-((2,4-dichlorophenyl)amino)-3-(3-methylbutanoyl)-5-nitro-4-oxo-1,4-dihydroquinoline-8-carboxylic acid |
| RE11 | 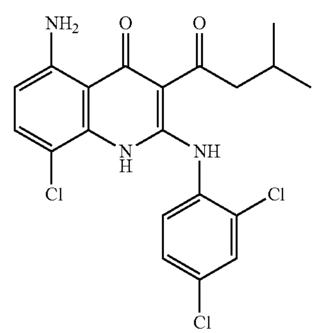 | 5-amino-8-chloro-2-((2,4-dichlorophenyl)amino)-3-(3-methylbutanoyl)quinolin-4(1H)-one |
| RE12 | 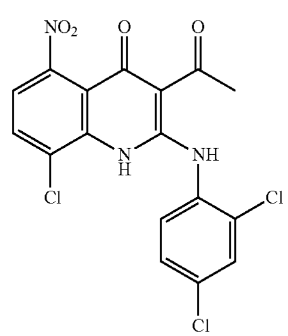 | 3-acetyl-8-chloro-2-((2,4-dichlorophenyl)amino)-5-nitroquinolin-4(1H)-one |

TABLE 1-continued

| Compound Code | Structure | Compound Name |
|---|---|---|
| RE13 | 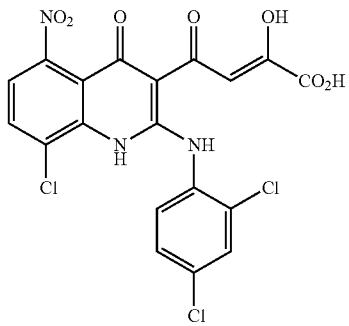 | (Z)-4-(8-chloro-2-((2,4-dichlorophenyl)amino)-5-nitro-4-oxo-1,4-dihydroquinolin-3-yl)-2-hydroxy-4-oxobut-2-enoic acid |
| RE14 | 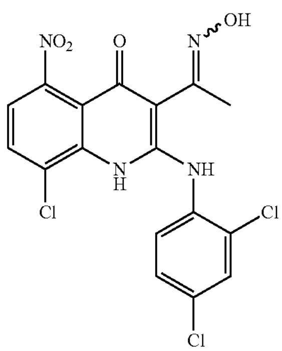 | 8-chloro-2-((2,4-dichlorophenyl)amino)-3-(1-(hydroxyimino)ethyl)-5-nitroquinolin-4(1H)-one |
| RE15 | 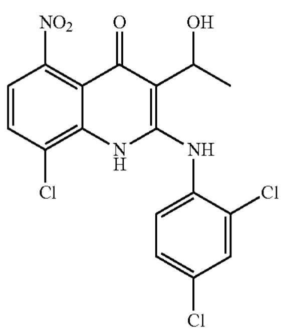 | 8-chloro-2-((2,4-dichlorophenyl)amino)-3-(1-hydroxyethyl)-5-nitroquinolin-4(1H)-one |
| RE16 | 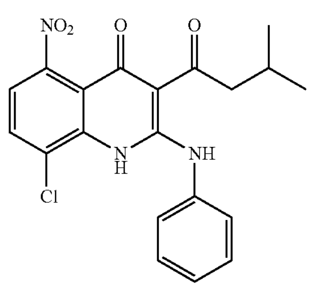 | 8-chloro-3-(3-methylbutanoyl)-5-nitro-2-(phenylamino)quinolin-4(1H)-one |
| RE17 | 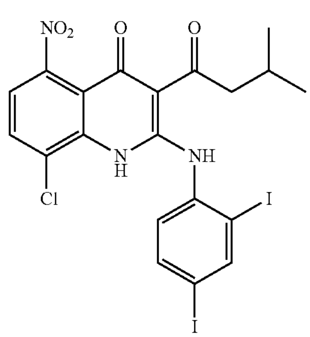 | 8-chloro-2-((2,4-diiodophenyl)amino)-3-(3-methylbutanoyl)-5-nitroquinolin-4(1H)-one |

TABLE 1-continued

| Compound Code | Structure | Compound Name |
|---|---|---|
| RE18 | 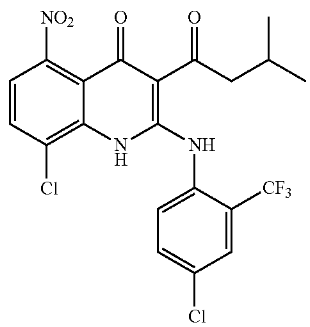 | 8-chloro-2-((4-chloro-2-(trifluoromethyl)phenyl)amino)-3-(3-methylbutanoyl)-5-nitroquinolin-4(1H)-one |
| RE19 | 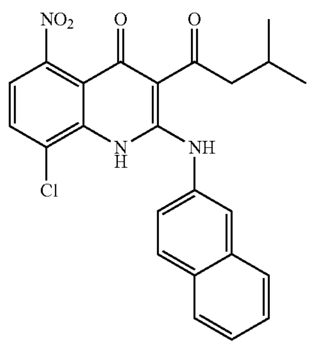 | 8-chloro-3-(3-methylbutanoyl)-2-(naphthalen-2-ylamino)-5-nitroquinolin-4(1H)-one |
| RE20 | 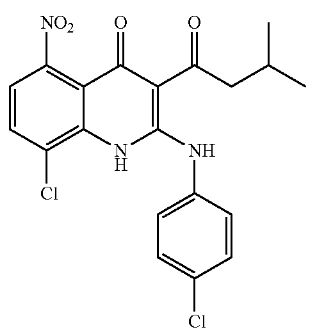 | 8-chloro-2-((4-chlorophenyl)amino)-3-(3-methylbutanoyl)-5-nitroquinolin-4(1H)-one |
| RE21 | 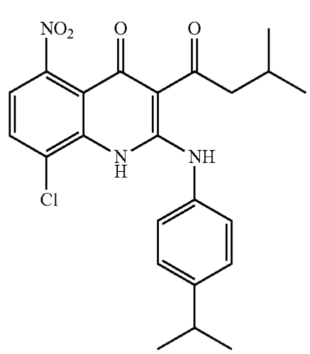 | 8-chloro-2-((4-isopropylphenyl)amino)-3-(3-methylbutanoyl)-5-nitroquinolin-4(1H)-one |

TABLE 1-continued

| Compound Code | Structure | Compound Name |
|---|---|---|
| RE22 | 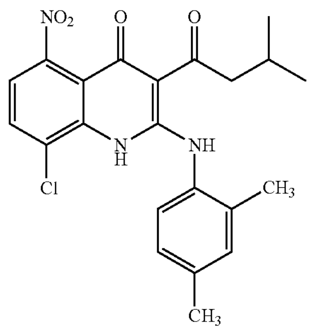 | 8-chloro-2-((2,4-dimethylphenyl)amino)-3-(3-methylbutanoyl)-5-nitroquinolin-4(1H)-one |
| RE23 | 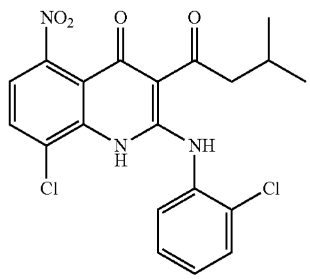 | 8-chloro-2-((2-chlorophenyl)amino)-3-(3-methylbutanoyl)-5-nitroquinolin-4(1H)-one |
| RE24 | 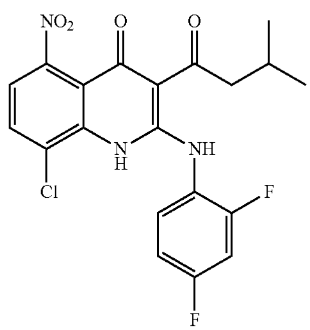 | 8-chloro-2-((2,4-difluorophenyl)amino)-3-(3-methylbutanoyl)-5-nitroquinolin-4(1H)-one |
| RE25 | 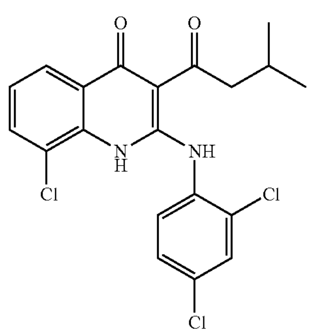 | 8-chloro-2-((2,4-dichlorophenyl)amino)-3-(3-methylbutanoyl)quinolin-4(1H)-one |
| RE26 | 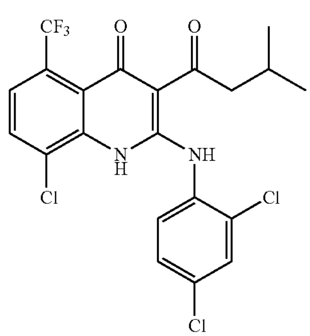 | 8-chloro-2-((2,4-dichlorophenyl)amino)-3-(3-methylbutanoyl)-5-(trifluoromethyl)quinolin-4(1H)-one |

TABLE 1-continued

| Compound Code | Structure | Compound Name |
|---|---|---|
| RE27 | 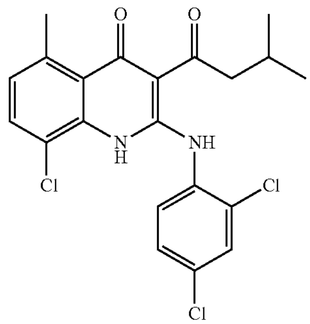 | 8-chloro-2-((2,4-dichlorophenyl)amino)-5-methyl-3-(3-methylbutanoyl)quinolin-4(1H)-one |
| RE28 | 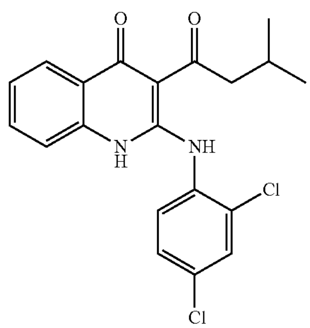 | 2-((2,4-dichlorophenyl)amino)-3-(3-methylbutanoyl)quinolin-4(1H)-one |
| RE29 | 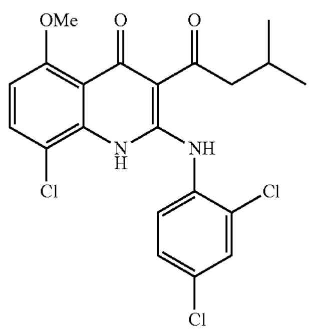 | 8-chloro-2-((2,4-dichlorophenyl)amino)-5-methoxy-3-(3-methylbutanoyl)quinolin-4(1H)-one |
| RE30 | 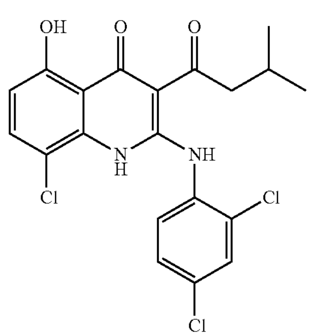 | 8-chloro-2-((2,4-dichlorophenyl)amino)-5-hydroxy-3-(3-methylbutanoyl)quinolin-4(1H)-one |

TABLE 1-continued

| Compound Code | Structure | Compound Name |
|---|---|---|
| RE31 | 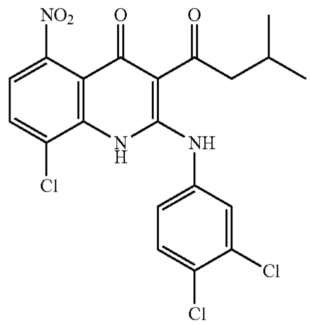 | 8-chloro-2-((3,4-dichlorophenyl)amino)-3-(3-methylbutanoyl)-5-nitroquinolin-4(1H)-one |
| RE32 | 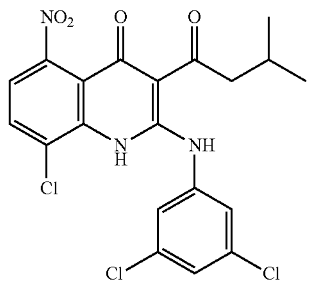 | 8-chloro-2-((3,5-dichlorophenyl)amino)-3-(3-methylbutanoyl)-5-nitroquinolin-4(1H)-one |
| RE33 | 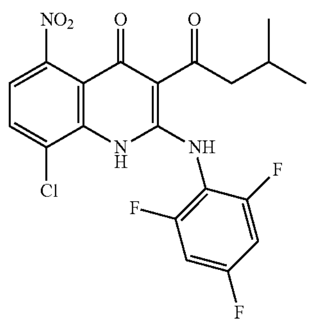 | 8-chloro-3-(3-methylbutanoyl)-5-nitro-2-((2,4,6-trifluorophenyl)amino)quinolin-4(1H)-one |
| RE34 | 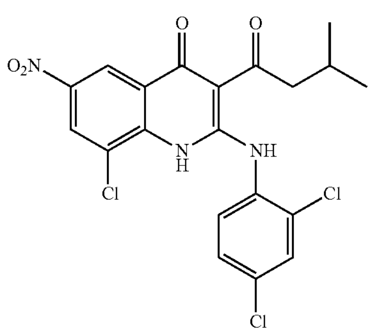 | 8-chloro-2-((2,4-dichlorophenyl)amino)-3-(3-methylbutanoyl)-6-nitroquinolin-4(1H)-one |
| RE35 | 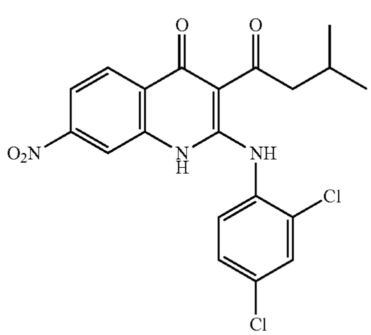 | 2-((2,4-dichlorophenyl)amino)-3-(3-methylbutanoyl)-7-nitroquinolin-4(1H)-one |

TABLE 1-continued

| Compound Code | Structure | Compound Name |
|---|---|---|
| RE36 | 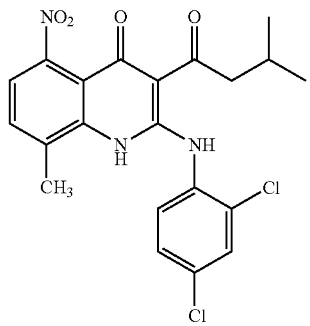 | 2-((2,4-dichlorophenyl)amino)-8-methyl-3-(3-methylbutanoyl)-5-nitroquinolin-4(1H)-one |
| RE37 | 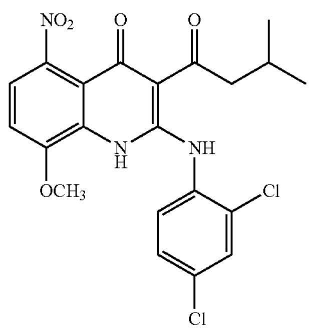 | 2-((2,4-dichlorophenyl)amino)-8-methoxy-3-(3-methylbutanoyl)-5-nitroquinolin-4(1H)-one |
| RE38 | 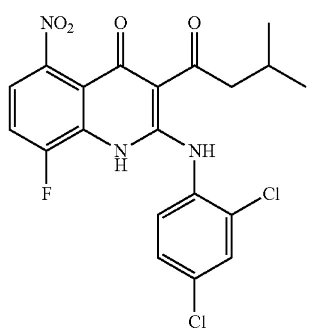 | 2-((2,4-dichlorophenyl)amino)-8-fluoro-3-(3-methylbutanoyl)-5-nitroquinolin-4(1H)-one |
| RE39 | 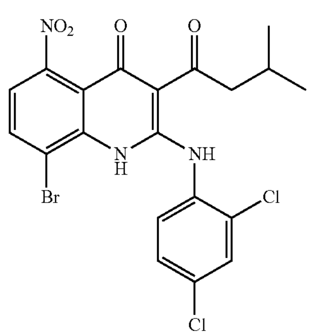 | 8-bromo-2-((2,4-dichlorophenyl)amino)-3-(3-methylbutanoyl)-5-nitroquinolin-4(1H)-one |

In certain embodiments, the compound of formula (I) is RE01.

In certain embodiments, the compound of formula (I) are those listed in Table 2.

Pharmaceutical Compositions

In another aspect, the present disclosure provides pharmaceutical compositions comprising one or more of compounds as described above with respect to formula (I) and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds. In certain embodiments, the composition may include one or more antibiotic compounds.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known. For buccal administration, the compositions may take the form of tablets or lozenges formulated in conventional manner. For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichloro-fluoromethane, dichloro-tetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethyl sulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

In some embodiments, the pharmaceutical composition is formulated for oral administration once a day or QD, and in some such formulations is a unit where the effective amount of the active ingredient ranges from 50 mg to 5000 mg. Alternatively, an oral solution may be provided ranging from a concentration of 1 mg/ml to 50 mg/ml or higher.

One embodiment of the disclosure includes administering a compound of the disclosure to provide a serum concentration ranging from 0.1 µM to 50 µM. One embodiment of the disclosure includes administering a compound of the disclosure to provide a serum concentration ranging from 1 µM to 20 µM. One embodiment of the disclosure includes administering a compound of the disclosure to provide a serum concentration ranging from 5 µM to 20 µM. One embodiment of the disclosure includes administering a compound of the disclosure to provide a serum concentration of 10 µM, 20 µM, 5 µM, 1 µM, 15 µM, or 40 µM.

One embodiment of the disclosure includes administering a compound of the disclosure at a dose of 1 to 100 mg/kg/day, 5-40 mg/kg/day, 10-20 mg/kg/day, 1-2 mg/kg/day, 20-40 mg/kg/day, 45-50 mg/kg/day, 50-60 mg/kg/day, 55-65 mg/kg/day, 60-70 mg/kg/day or 65-75 mg/kg/day.

The compositions described herein may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The disclosure is not limited to dosing intervals that are spaced equally in time, but encompass doses at non-equal intervals, such as a priming schedule consisting of administration at 1 day, 4 days, 7 days, and 25 days, just to provide a non-limiting example.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

As one aspect of the present disclosure contemplates the treatment of the disease/conditions with the compounds of the disclosure, the disclosure further relates to pharmaceutical compositions in kit form. When the composition of the disclosure is a part of a combination therapy with a secondary therapeutic agent, the kit may comprise two separate pharmaceutical compositions: one of compound of the present disclosure, and another of a second therapeutic agent. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Definitions

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" (i.e., the attachment is via the last portion of the name) unless a dash indicates otherwise. For example, $C_1$-$C_6$alkoxycarbonyloxy and —OC(O)$C_1$-$C_6$alkyl indicate the same functionality; similarly arylalkyl and—alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

The term "alkylene" refers to a bivalent alkyl group. An "alkylene chain" is a polymethylene group, i.e., —$(CH_2)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]

nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, 2,3-dihydrothieno[3,4-b][1,4]dioxan-5-yl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The terms "heterocyclyl" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thia" as used herein means a =S group.

The term "unsaturated" as used herein means the referenced chemical structure contains at least one multiple carbon-carbon bond, but is not aromatic. For example, an unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" or "effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art. An effective amount is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

"Treating" or "treatment" as used herein covers the treatment of a disease or disorder described herein, in a subject, preferably a human, and includes:
 i. inhibiting a disease or disorder, i.e., arresting its development;
 ii. relieving a disease or disorder, i.e., causing regression of the disorder;
 iii. slowing progression of the disorder; and/or
 iv. inhibiting, relieving, ameliorating, or slowing progression of one or more symptoms of the disease or disorder.

"Subject" refers to a warm blooded animal such as a mammal, preferably a human, or a human child, which is afflicted with, or has the potential to be afflicted with one or more diseases and disorders described herein.

Methods of Preparation

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/I, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-6, general procedures (below), and/or analogous synthetic procedures. One of skill in the art can adapt the reaction sequences of Schemes 1-6, general procedures, and Examples 1-13 to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

General Procedures

Representative synthetic procedures for the preparation of compounds of the invention are outlined below in Schemes 1-6.

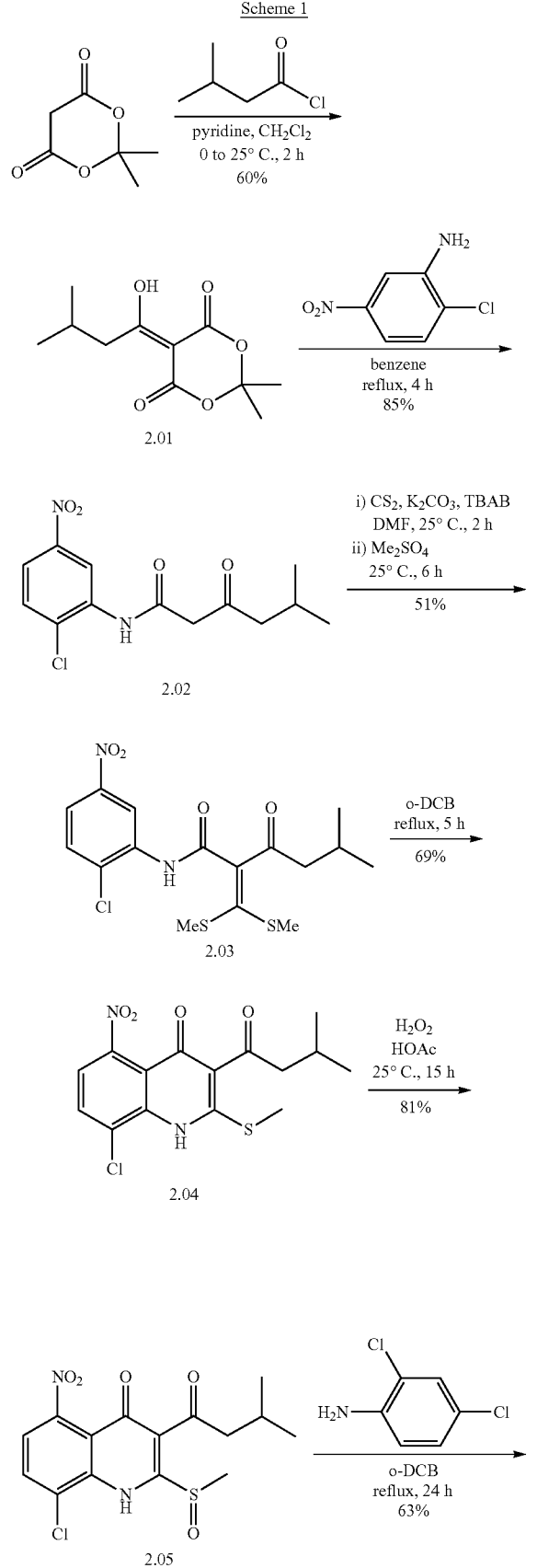
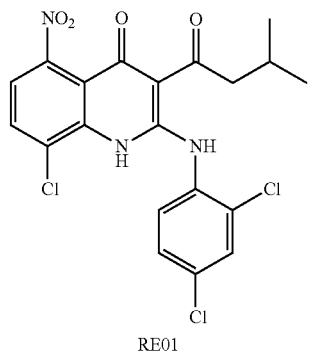
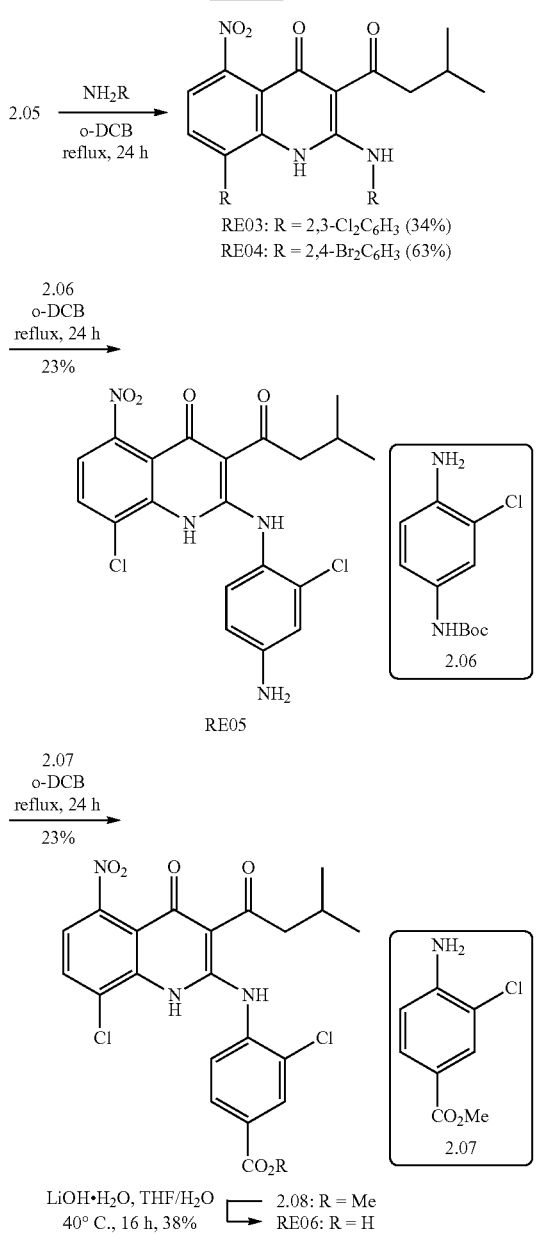

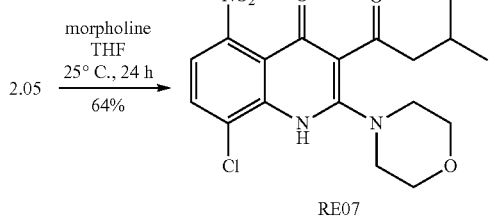

2.05 → morpholine THF 25° C., 24 h 64% → RE07

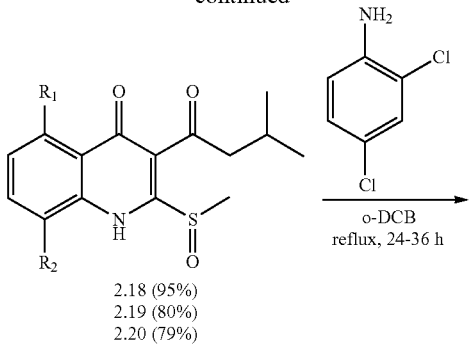

2.18 (95%)
2.19 (80%)
2.20 (79%)

Scheme 3

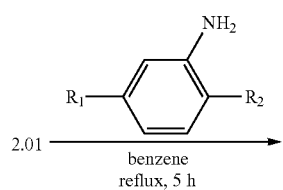

2.01 → benzene reflux, 5 h →

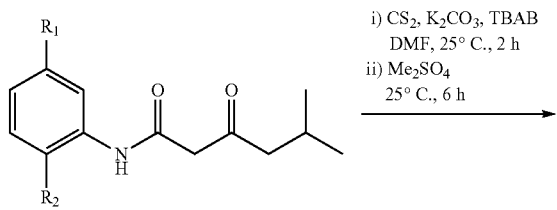

2.09: $R_1$ = Cl, $R_2$ = $CO_2Me$ (88%)
2.10: $R_1$ = $CO_2Me$, $R_2$ = Cl (72%)
2.11: $R_1$ = $NO_2$, $R_2$ = $CO_2Me$ (66%)

i) $CS_2$, $K_2CO_3$, TBAB DMF, 25° C., 2 h
ii) $Me_2SO_4$ 25° C., 6 h

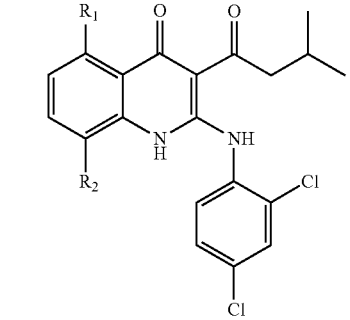

a: 2.21 (50%) → RE08: $R_1$ = Cl, $R_2$ = $CO_2H$ (43%)
b: 2.22 (25%) → RE09: $R_1$ = $CO_2H$, $R_2$ = Cl (60%)
c: 2.23 (35%) → RE10: $R_1$ = $NO_2$, $R_2$ = $CO_2H$ (80%)

a) LiOH·$H_2O$, THF/$H_2O$, 40° C., 20 h
b) NaOH, MeOH, reflux, 6 h

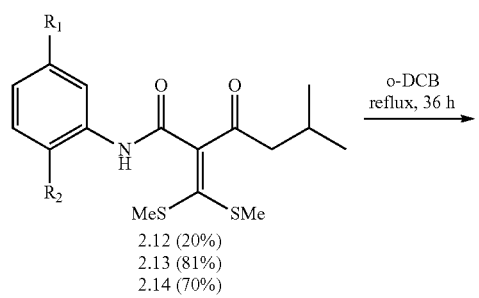

2.12 (20%)
2.13 (81%)
2.14 (70%)

o-DCB reflux, 36 h →

Scheme 4

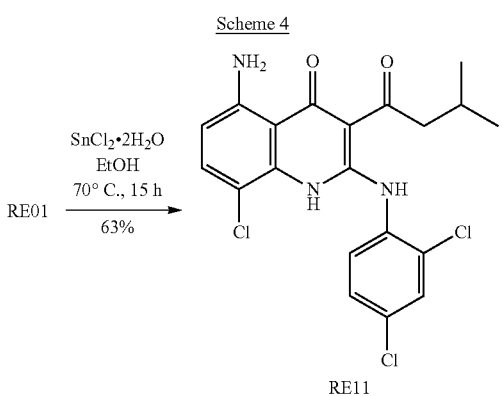 [SMILES: CC(C)CC(=O)c1c(Nc2ccc(Cl)cc2Cl)[nH]c2c(Cl)ccc(N)c2c1=O]

RE01 → $SnCl_2$·$2H_2O$ EtOH 70° C., 15 h 63% → RE11

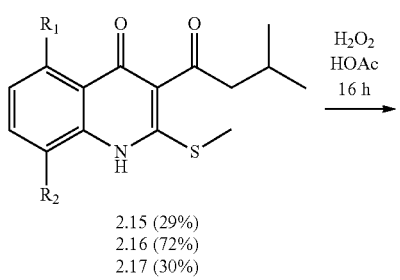

2.15 (29%)
2.16 (72%)
2.17 (30%)

$H_2O_2$ HOAc 16 h →

Scheme 5

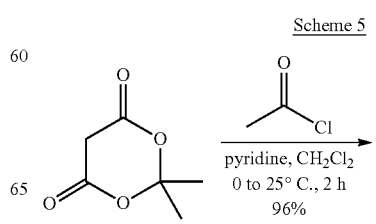

pyridine, $CH_2Cl_2$ 0 to 25° C., 2 h 96%

-continued
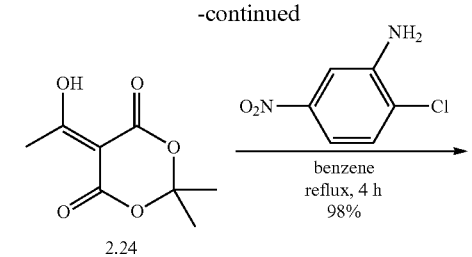
2.24
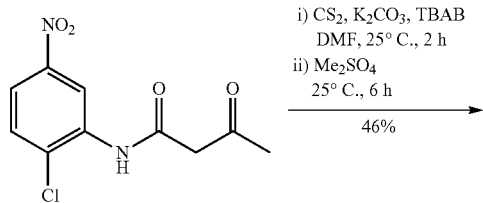
2.25
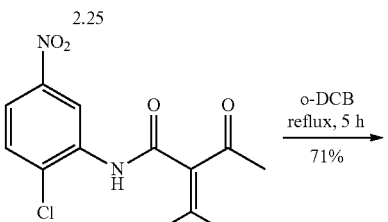
2.26
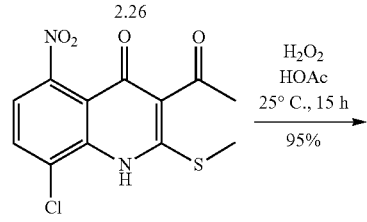
2.27
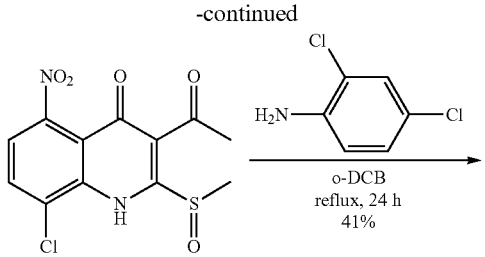
2.28
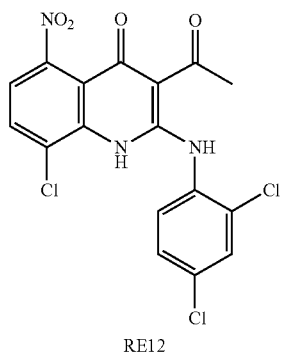
RE12
Scheme 6
RE12
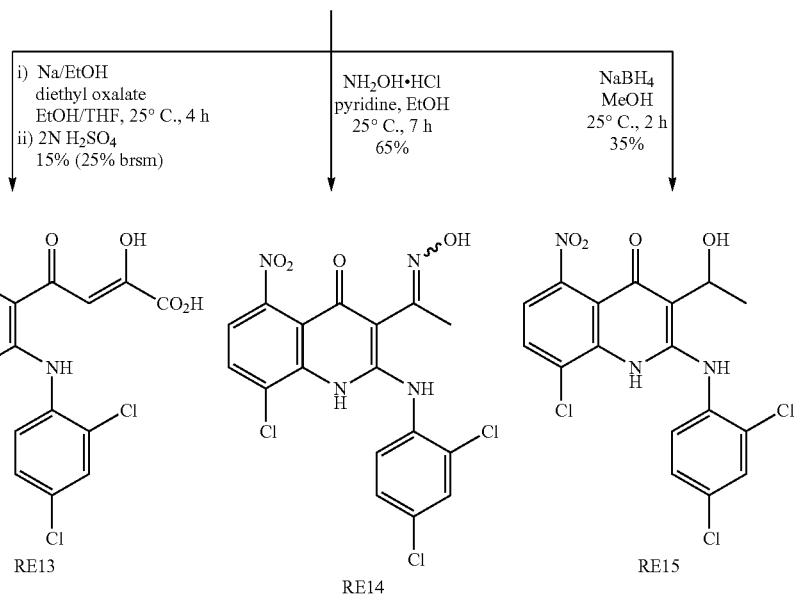
RE13
RE14
RE15

Materials and Methods

All reactions were conducted in oven-dried glassware under nitrogen. Unless otherwise stated all reagents were purchased from Sigma-Aldrich, Acros, or Fisher and were used without further purification. All solvents were ACS grade or better and used without further purification except tetrahydrofuran (THF) which was freshly distilled from sodium/benzophenone each time before use. Analytical thin layer chromatography (TLC) was performed with glass backed silica gel (60 Å) plates with fluorescent indication (Whatman). Visualization was accomplished by UV irradiation at 254 nm and/or by staining with p-anisaldehyde solution. Flash column chromatography was performed by using silica gel (particle size 230-400 mesh, 60 Å). All $^1$H NMR and $^{13}$C NMR spectrum were recorded with a Varian 400 (400 MHz) and a Bruker 500 (500 MHz) spectrometer in $CDCl_3$ by using the signal of residual $CHCl_3$, as an internal standard. All NMR δ values are given in ppm, and all J values are in Hz. Electrospray ionization (ESI) mass spectrometry (MS) were recorded with an Agilent 1100 series (LC/MSD trap) spectrometer and were performed to obtain the molecular masses of the compounds.

EXAMPLES

The preparation of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Example 1

Preparation of 2.03

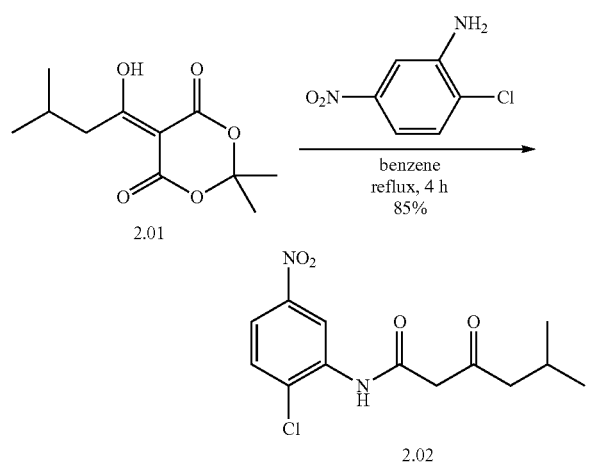

To a solution of the known 2.0159 (1.664 g, 7.29 mmol) in benzene (35 mL) was added 2-chloro-5-nitroaniline (1.006 g, 5.83 mmol) at 25° C. The reaction mixture was refluxed for 4 h and concentrated in vacuo. The residue was purified by column chromatography (silica gel, hexanes/EtOAc, 7/1) to afford 2.02 as a yellow oil (1.481 g, 85%): $^1$H NMR (400 MHz, $CDCl_3$) δ 10.21 (s, 1H), 9.31 (d, J=2.8 Hz, 1H) 7.93 (dd, J=8.8, 2.8 Hz, 1H), 7.56 (d, J=8.8 Hz, 1H), 3.65 (s, 2H), 2.48 (d, J=6.8 Hz, 2H), 2.22 (m, 1H) 0.99 (s, 3H), 0.97 (s, 3H).

Preparation of 2.03

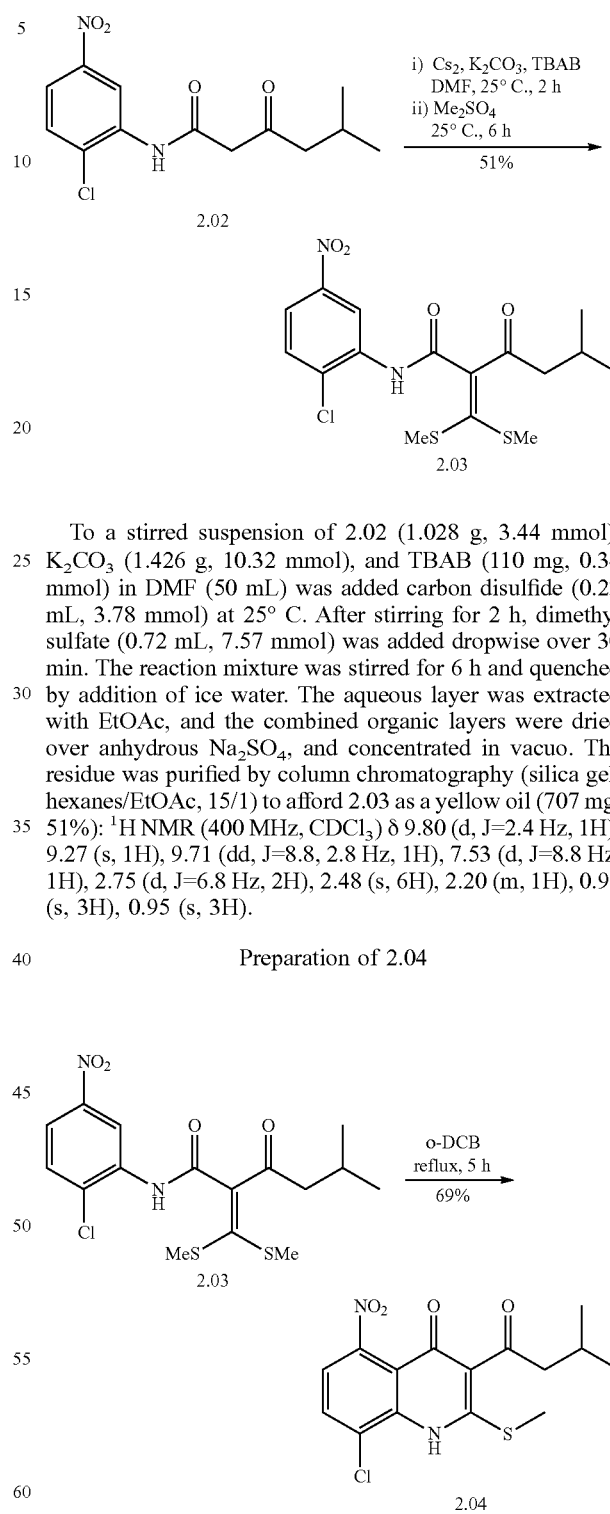

To a stirred suspension of 2.02 (1.028 g, 3.44 mmol), $K_2CO_3$ (1.426 g, 10.32 mmol), and TBAB (110 mg, 0.34 mmol) in DMF (50 mL) was added carbon disulfide (0.23 mL, 3.78 mmol) at 25° C. After stirring for 2 h, dimethyl sulfate (0.72 mL, 7.57 mmol) was added dropwise over 30 min. The reaction mixture was stirred for 6 h and quenched by addition of ice water. The aqueous layer was extracted with EtOAc, and the combined organic layers were dried over anhydrous $Na_2SO_4$, and concentrated in vacuo. The residue was purified by column chromatography (silica gel, hexanes/EtOAc, 15/1) to afford 2.03 as a yellow oil (707 mg, 51%): $^1$H NMR (400 MHz, $CDCl_3$) δ 9.80 (d, J=2.4 Hz, 1H), 9.27 (s, 1H), 9.71 (dd, J=8.8, 2.8 Hz, 1H), 7.53 (d, J=8.8 Hz, 1H), 2.75 (d, J=6.8 Hz, 2H), 2.48 (s, 6H), 2.20 (m, 1H), 0.96 (s, 3H), 0.95 (s, 3H).

Preparation of 2.04

A solution of 2.03 (336 mg, 0.83 mmol) in 1,2-dichlorobenzene (8 mL) was refluxed for 5 h. The reaction mixture was concentrated in vacuo and the residue was purified by column chromatography (silica gel, hexanes/EtOAc, 4/1) to afford 2.04 (203 mg, 69%): $^1$H NMR (400 MHz, $CDCl_3$) δ

7.85 (d, J=8.4 Hz, 1H), 7.36 (d, J=8.4 Hz, 1H), 3.22 (d, J=6.8 Hz, 2H), 2.80 (s, 3H), 2.39 (m, 1H), 1.04 (s, 3H), 1.02 (s, 3H).

Preparation of 2.05

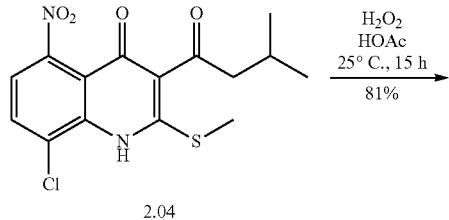

2.04

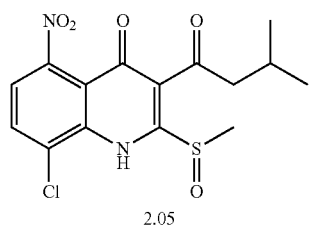

2.05

To a solution of 2.04 (68 mg, 0.19 mmol) in acetic acid (2 mL) was added hydrogen peroxide (30%, 0.05 mL, 0.48 mmol) at 25° C. After stirring for 16 h, the reaction mixture was poured into ice water and the aqueous layer was extracted with EtOAc. The combined organic layers were washed with brine and dried over anhydrous Na₂SO₄, and concentrated in vacuo. The residue was purified by column chromatography (silica gel, hexanes/EtOAc, 3/1) to afford 2.05 as a yellow oil (57 mg, 81%): ¹H NMR (400 MHz, CDCl₃) δ 11.30 (s, 1H), 7.87 (d, J=8.4 Hz, 1H), 7.42 (d, J=8.4 Hz, 1H), 3.10 (m, 2H), 3.05 (s, 3H), 2.21 (m, 1H), 0.95 (dd, J=6.0, 6.8 Hz, 6H).

Preparation of RE01 (8-chloro-2-((2,4-dichlorophenyl)amino)-3-(3-methylbutanoyl)-5-nitroquinolin-4 (1H)-one)

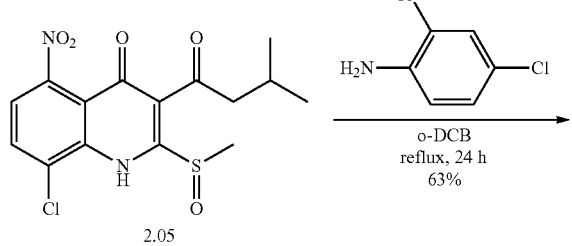

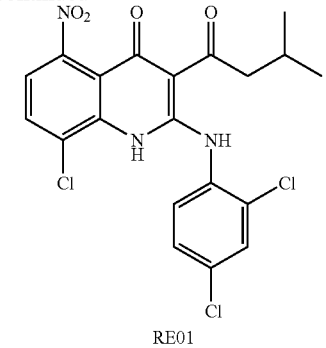

RE01

To a solution of 2.05 (13 mg, 0.035 mmol) in 1,2-dichlorobenzene (1 mL) was added 2,4-dichloroaniline (18 mg, 0.11 mmol) at 25° C. The reaction mixture was refluxed for 24 h and concentrated in vacuo to give a residue, which was dissolved in EtOAc. The ethyl acetate solution was washed with brine, dried over anhydrous Na₂SO₄, and concentrated in vacuo. The residue was purified by column chromatography (silica gel, hexanes/EtOAc, 2/1) to afford RE01 as a yellow solid (9 mg, 57%): ¹H NMR (400 MHz, CDCl₃) δ 13.42 (s, 1H), 8.20 (s, 1H), 7.68 (s, 1H), 7.62 (d, J=8.4 Hz, 1H), 7.48 (m, 2H), 7.17 (d, J=8.4 Hz, 1H), 3.11 (d, J=6.8 Hz, 2H), 2.25 (m, 1H), 0.98 (s, 3H), 0.96 (s, 3H); ¹³C NMR (125 MHz, CDCl₃) b 204.1, 172.8 153.5, 147.9, 135.1, 133.5, 132.5, 131.7, 131.6, 130.4, 129.2, 128.0, 122.3, 117.9, 117.4, 101.8, 52.7, 24.8, 22.9.

Example 2

Preparation of RE03 (8-chloro-2-((2,3-dichlorophenyl)amino)-3-(3-methylbutanoyl)-5-nitroquinolin-4 (1H)-one) bbb

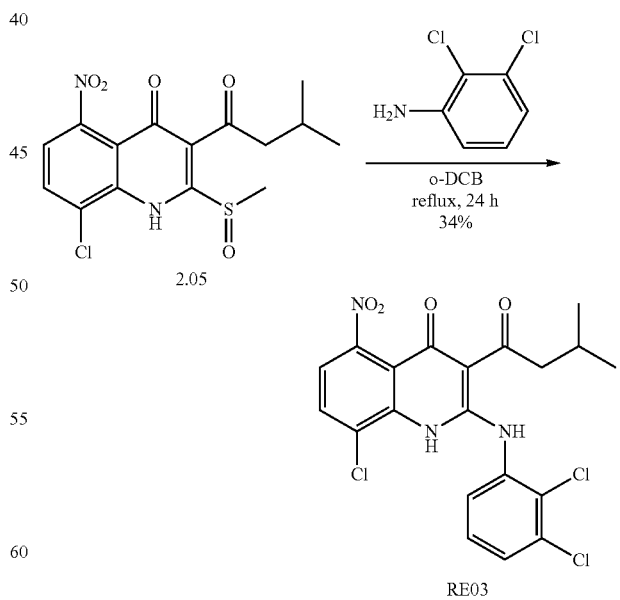

To a solution of 2.05 (24 mg, 0.065 mmol) in 1,2-dichlorobenzene (1 mL) was added 2,3-dichloroaniline (11 mg, 0.065 mmol) at 25° C. The reaction mixture was refluxed for 24 h and concentrated in vacuo to give a residue, which was dissolved in EtOAc. The ethyl acetate solution was washed with brine, dried over anhydrous $Na_2SO_4$, and concentrated in vacuo. The residue was purified by column chromatography (silica gel, hexanes/EtOAc, 4/1) to afford RE03 as a yellow oil (10 mg, 34%): $^1$H NMR (400 MHz, $CDCl_3$) δ 13.55 (s, 1H), 8.32 (s, 1H), 7.61 (d, J=8.0 Hz, 1H), 7.59 (dd, J=7.6, 2.0 Hz, 1H), 7.48-7.41 (m, 2H), 7.17 (d, J=8.0 Hz, 1H), 3.13 (d, J=6.4 Hz, 2H), 2.26 (m, 1H), 0.98 (d, J=6.4 Hz, 6H).

Example 3

Preparation of RE04 (8-chloro-2-((2,4-dibromophenyl)amino)-3-(3-methylbutanoyl)-5-nitroquinolin-4(1H)-one)

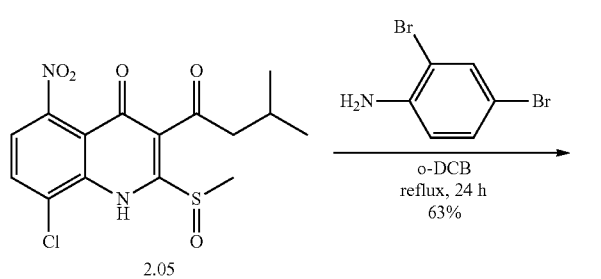

To a solution of 2.05 (20 mg, 0.054 mmol) in 1,2-dichlorobenzene (1 mL) was added 2,4-dibromoaniline (20 mg, 0.081 mmol) at 25° C. The reaction mixture was refluxed for 24 h and concentrated in vacuo to give a residue, which was dissolved in EtOAc. The ethyl acetate solution was washed with brine, dried over anhydrous $Na_2SO_4$, and concentrated in vacuo. The residue was purified by column chromatography (silica gel, hexanes/EtOAc, 3/1) to afford RE04 as a yellow solid (19 mg, 63%): $^1$H NMR (400 MHz, $CDCl_3$) δ 13.41 (s, 1H), 8.17 (s, 1H), 8.00 (d, J=2.0 Hz, 1H), 7.68 (dd, J=8.4, 2.0 Hz, 1H), 7.62 (d, J=8.0 Hz, 1H), 7.40 (d, J=8.4 Hz, 1H), 7.17 (d, J=8.0 Hz, 1H), 3.12 (d, J=6.8 Hz, 2H), 2.26 (m, 1H), 0.98 (d, J=6.8 Hz, 6H).

Example 4

Preparation of RE05 (2-((4-amino-2-chlorophenyl)amino)-8-chloro-3-(3-methylbutanoyl)-5-nitroquinolin-4(1H)-one)

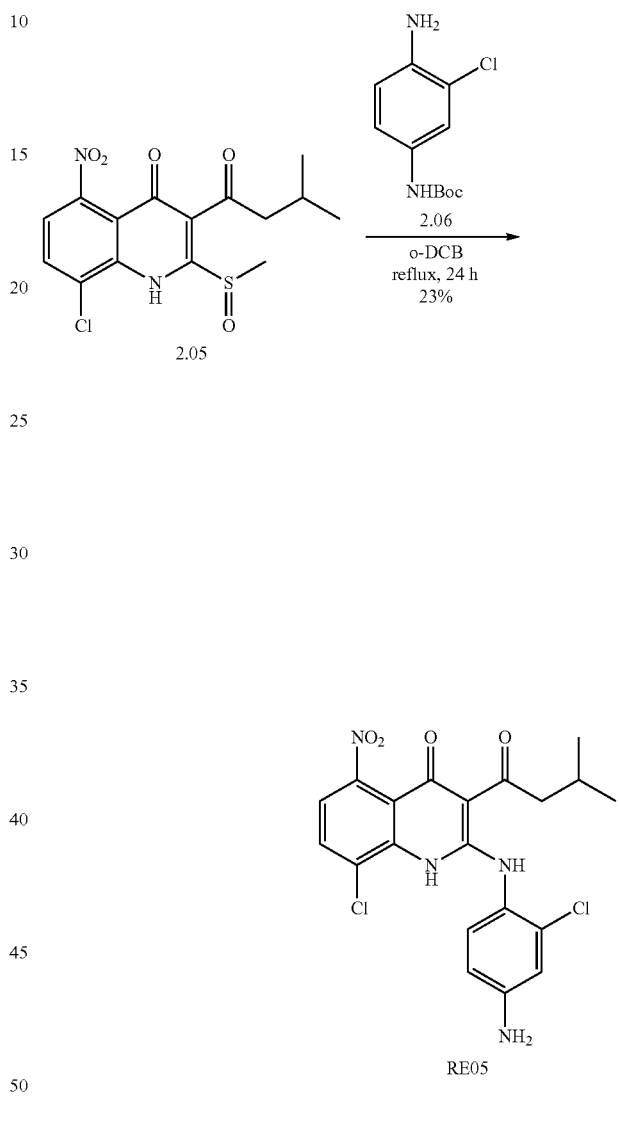

To a solution of 2.05 (12 mg, 0.032 mmol) in 1,2-dichlorobenzene (1 mL) was added tert-butyl (4-amino-3-chlorophenyl)carbamate 2.06 (23 mg, 0.096 mmol) at 25° C. The reaction mixture was refluxed for 24 h and concentrated in vacuo to give a residue, which was dissolved in EtOAc. The ethyl acetate solution was washed with brine, dried over anhydrous $Na_2SO_4$, and concentrated in vacuo. The residue was purified by column chromatography (silica gel, hexanes/EtOAc, 2/1) to afford RE05 as a yellow oil (4 mg, 29%): $^1$H NMR (400 MHz, $CDC_3$) δ 12.92 (s, 1H), 8.38 (s, 1H), 7.58 (d, J=8.0 Hz, 1H), 7.31 (s, 1H), 7.13 (d, J=8.0 Hz, 1H), 7.09 (d, J=8.4 Hz, 1H), 6.92 (d, J=8.4 Hz, 1H), 4.34 (s, 2H), 3.11 (d, J=6.4 Hz, 2H), 2.24 (m, 1H), 0.97 (d, J=6.4 Hz, 6H); HRMS (ESI) m/z 449.0778 [(M+H)$^+$, $C_{20}H_{18}Cl_2N_4O_4$ requires 449.0778].

Example 5

Preparation of RE06 (methyl 3-chloro-4-((8-chloro-3-(3-methylbutanoyl)-5-nitro-4-oxo-1,4-dihydroquinolin-2-yl)amino)benzoate)

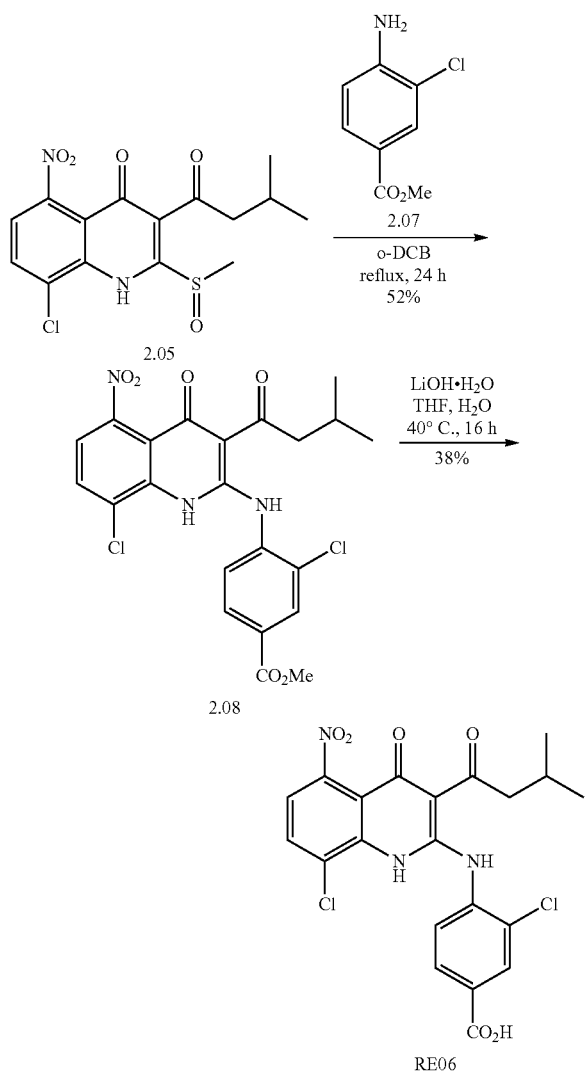

To a solution of 2.05 (17 mg, 0.046 mmol) in 1,2-dichlorobenzene (1 mL) was added methyl 4-amino-3-chlorobenzoate 2.07 (26 mg, 0.14 mmol) at 25° C. The reaction mixture was refluxed for 24 h and concentrated in vacuo to give a residue, which was dissolved in EtOAc. The ethyl acetate solution was washed with brine, dried over anhydrous $Na_2SO_4$, and concentrated in vacuo. The residue was purified by column chromatography (silica gel, hexanes/EtOAc, 4/1) to afford 2.08 as a yellow oil (12 mg, 52%): $^1$H NMR (400 MHz, $CDCl_3$) δ 13.71 (s, 1H), 8.45 (s, 1H), 8.32 (d, J=1.6 Hz, 1H), 8.14 (dd, J=8.4, 1.6 Hz, 1H), 7.63 (d, J=8.4 Hz, 2H), 7.19 (d, J=8.4 Hz, 1H), 3.99 (s, 3H), 3.13 (d, J=6.8 Hz, 2H), 2.16 (m, 1H), 0.97 (d, J=6.8 Hz, 6H); HRMS (ESI) m/z 442.0723 [(M+H)+, $C_{22}H_{19}Cl_2N_3O_6$ requires 429.0734]. [Hydrolysis] To a solution of 2.08 (8 mg, 0.016 mmol) in THF (0.3 mL) was added a solution of $LiOH·H_2O$ (7 mg, 0.16 mmol) in $H_2O$ (0.1 mL). The resulting mixture was stirred at 40° C. for 16 h. 2 N HCl (1 mL) was added and the aqueous layer was extracted with EtOAc. The combined organic layers were dried over anhydrous $Na_2SO_4$, and concentrated in vacuo. The residue was purified by column chromatography (silica gel, hexanes/EtOAc/HOAc, 4/1/0.01) to afford RE06 as a yellow oil (3 mg, 38%): HRMS (ESI) m/z 478.0571 [(M+H)+, $C_{21}H_{17}Cl_2N_3O_6$ requires 478.0567].

Example 6

Preparation of RE07 (8-chloro-3-(3-methylbutanoyl)-2-morpholino-5-nitroquinolin-4(1H)-one)

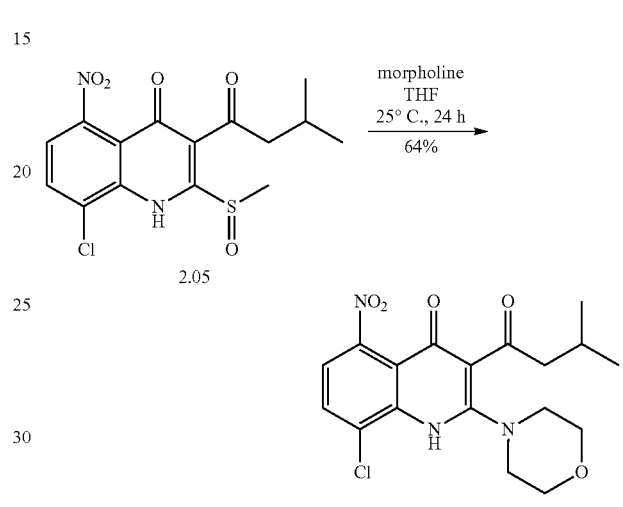

To a solution of 2.05 (10 mg, 0.027 mmol) in dry THF (0.5 mL) was added morpholine (0.01 mL, 0.081 mmol). The reaction mixture was stirred at 25° C. for 24 h and concentrated in vacuo lgiving a residue, which was dissolved in EtOAc. The ethyl acetate solution was washed with brine, dried over anhydrous $Na_2SO_4$, and concentrated in vacuo.

The residue was purified by column chromatography (silica gel, hexanes/EtOAc, 3/1) to afford RE07 as a yellow oil (7 mg, 64%): $^1$H NMR (400 MHz, $CDCl_3$) δ 13.77 (s, 1H), 7.75 (d, J=8.4 Hz, 1H), 7.26 (d, J=8.4 Hz, 1H), 3.82 (m, 4H), 3.60 (m, 4H), 2.94 (d, J=6.8 Hz, 2H), 2.15 (m, 1H), 0.85 (d, J=6.8 Hz, 6H).

Example 7

Preparation of 2.09

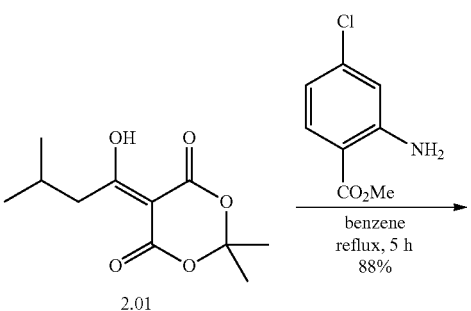

-continued

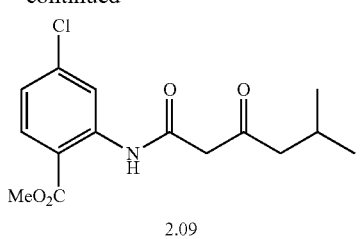
2.09

To a solution of the known 2.01 (300 mg, 1.31 mmol) in benzene (5 mL) was added methyl 2-amino-4-chlorobenzoate (195 mg, 1.05 mmol) at 25° C. The reaction mixture was refluxed for 5 h and concentrated in vacuo. The residue was purified by column chromatography (silica gel, hexanes/EtOAc, 10/1) to afford 2.09 as a yellow oil (287 g, 88%): $^1$H NMR (400 MHz, CDCl$_3$) δ 11.37 (s, 1H), 8.75 (d, J=2.0 Hz, 1H), 7.93 (d, J=8.4 Hz, 1H), 7.04 (dd, J=8.4, 2.0 Hz, 1H), 3.92 (s, 3H), 3.55 (s, 2H), 2.48 (d, J=6.8 Hz, 2H), 2.18 (m, 1H), 0.94 (d, J=6.8 Hz, 6H).

Preparation of 2.12

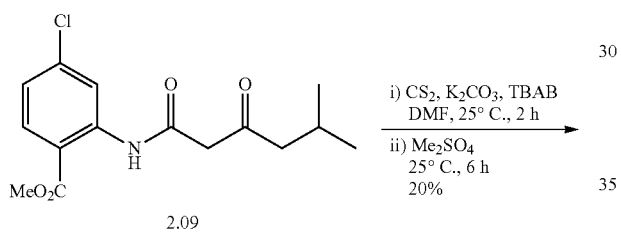

To a stirred suspension of 2.09 (287 mg, 0.92 mmol), K$_2$CO$_3$ (381 g, 2.76 mmol), and TBAB (30 mg, 0.092 mmol) in DMF (10 mL) was added carbon disulfide (0.06 mL, 1.01 mmol) at 25° C. After stirring for 2 h, dimethyl sulfate (0.2 mL, 2.02 mmol) was added dropwise over 30 min. The reaction mixture was stirred for 6 h and quenched by addition of ice water. The aqueous layer was extracted with EtOAc, and the combined organic layers were dried over anhydrous Na$_2$SO$_4$, and concentrated in vacuo. The residue was purified by column chromatography (silica gel, hexanes/EtOAc, 5/1) to afford 2.12 as a yellow oil (77 mg, 20%): $^1$H NMR (400 MHz, CDCl$_3$) δ 11.32 (s, 1H), 8.88 (d, J=2.0 Hz, 1H), 7.98 (d, J=8.4 Hz, 1H), 7.10 (dd, J=8.4, 2.0 Hz, 1H), 3.92 (s, 3H), 2.62 (d, J=6.8 Hz, 2H), 2.44 (s, 6H), 2.24 (m, 1H), 0.94 (d, J=6.8 Hz, 6H).

Preparation of 2.15

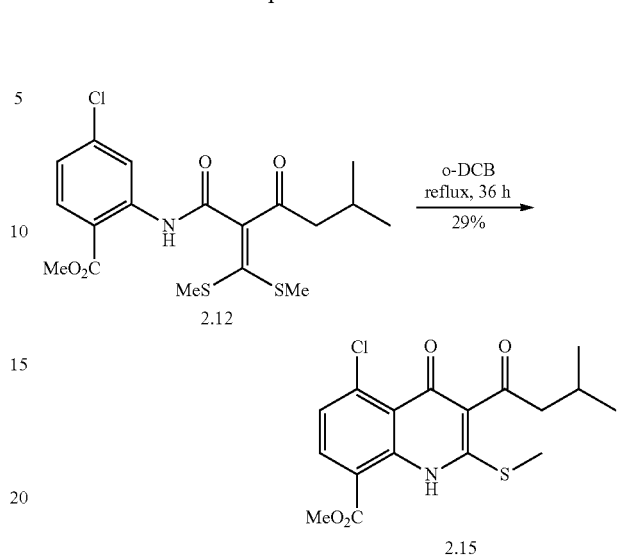

A solution of 2.12 (77 mg, 0.19 mmol) in 1,2-dichlorobenzene (2 mL) was refluxed for 36 h. The reaction mixture was concentrated in vacuo and the residue was purified by column chromatography (silica gel, hexanes/EtOAc, 4/1) to afford 2.15 (20 mg, 29%): $^1$H NMR (400 MHz, CDCl$_3$) δ 12.37 (s, 1H), 8.17 (d, J=8.4 Hz, 1H), 7.33 (d, J=8.4 Hz, 1H), 4.02 (s, 3H), 3.03 (d, J=6.8 Hz, 2H), 2.62 (s, 3H), 2.29 (m, 1H), 0.96 (d, J=6.8 Hz, 6H).

Preparation of 2.18

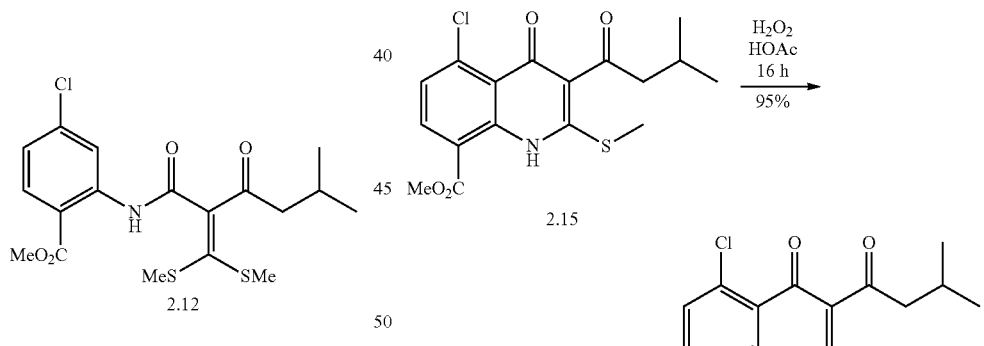

To a solution of 2.15 (20 mg, mmol) in acetic acid (1 mL) was added hydrogen peroxide (0.013 mL, 0.13 mmol) at 25° C. After stirring for 16 h, the reaction mixture was poured into ice water and the aqueous layer was extracted with EtOAc. The combined organic layers were washed with brine and dried over anhydrous Na$_2$SO$_4$, and concentrated in vacuo. The residue was purified by column chromatography (silica gel, hexanes/EtOAc, 1/1) to afford 2.18 as a yellow oil (18 mg, 95%): $^1$H NMR (400 MHz, CDCl$_3$) δ 13.63 (s, 1H), 8.29 (d, J=8.4 Hz, 1H), 7.48 (d, J=8.4 Hz, 1H), 4.05 (s, 3H), 3.14 (d, J=6.8 Hz, 1H), 3.13 (d, J=6.8 Hz, 1H), 3.03 (s, 3H), 2.25 (m, 1H), 0.98 (d, J=6.8 Hz, 3H), 0.95 (d, J=6.8 Hz, 3H).

Preparation of RE08 (5-chloro-2-((2,4-dichlorophenyl)amino)-3-(3-methylbutanoyl)-4-oxo-1,4-dihydroquinoline-8-carboxylic acid)

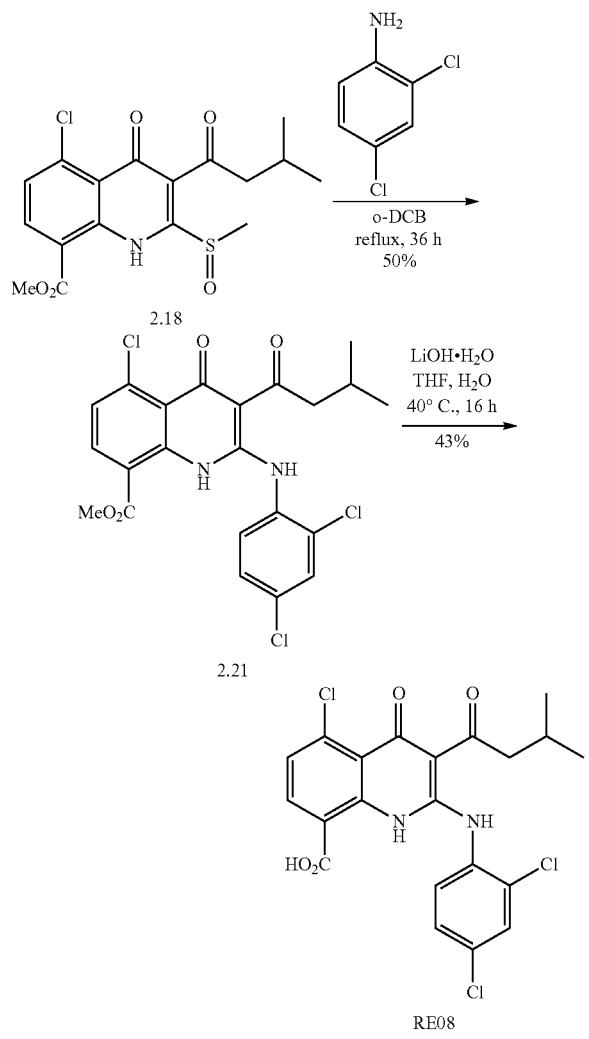

To a solution of 2.18 (11 mg, 0.029 mmol) in 1,2-dichlorobenzene (1 mL) was added 2,4-dichloroaniline (14 mg, 0.087 mmol) at 25° C. The reaction mixture was refluxed for 36 h and concentrated in vacuo to give a residue, which was dissolved in EtOAc. The ethyl acetate solution was washed with brine, dried over anhydrous Na$_2$SO$_4$, and concentrated in vacuo. The residue was purified by column chromatography (silica gel, hexanes/EtOAc, 4/1) to afford 2.21 as a yellow solid (7 mg, 50%): $^1$H NMR (400 MHz, CDCl$_3$) δ 13.16 (s, 1H), 11.88 (s, 1H), 8.04 (d, J=8.8 Hz, 1H), 7.62 (d, J=2.4 Hz, 1H), 7.43 (m, 2H), 7.25 (d, J=8.8 Hz, 1H), 3.85 (s, 3H), 3.19 (d, J=6.8 Hz, 2H), 2.33 (m, 1H), 1.01 (d, J=6.8 Hz, 6H) [Hydrolysis] To a solution of 2.21 (7 mg, 0.015 mmol) in THF (0.3 mL) was added a solution of LiOH·H$_2$O (6 mg, 0.15 mmol) in H$_2$O (0.1 mL). The resulting mixture was stirred at 40° C. for 20 h. 2 N HCl (1 mL) was added and the aqueous layer was extracted with EtOAc. The combined organic layers were dried over anhydrous Na$_2$SO$_4$, and concentrated in vacuo. The residue was purified by column chromatography (silica gel, hexanes/EtOAc/HOAc, 4/1/0.01) to afford RE08 as a yellow oil (3 mg, 43%): $^1$H NMR (400 MHz, CD3OD) b 8.15 (d, J=8.4 Hz, 1H), 7.74 (d, J=2.4 Hz, 1H), 7.65 (d, J=8.4 Hz, 1H), 7.52 (dd, J=8.4, 2.4 Hz, 1H), 7.33 (d, J=8.4 Hz, 1H), 3.06 (d, J=6.8 Hz, 2H), 2.28 (m, 1H), 1.00 (d, J=6.8 Hz, 6H).

Example 8

Preparation of 2.10

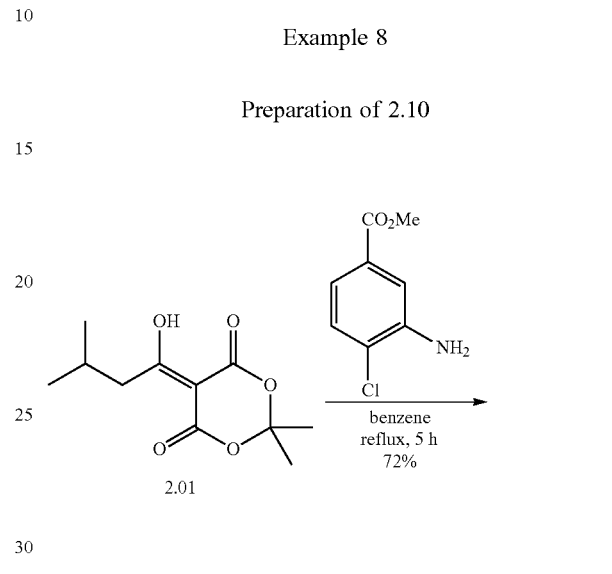

To a solution of the known 2.01 (492 mg, 2.16 mmol) in benzene (10 mL) was added methyl 3-amino-4-chlorobenzoate (320 mg, 1.72 mmol) at 25° C. The reaction mixture was refluxed for 5 h and concentrated in vacuo. The residue was purified by column chromatography (silica gel, hexanes/EtOAc, 7/1) to afford 2.10 as a yellow oil (386 mg, 72%): 1H NMR (400 MHz, CDCl$_3$) δ; 9.79 (s, 1H), 8.89 (m, 1H), 7.67 (m, 1H), 7.39 (dd, J=8.0, 4.0 Hz, 1H), 3.86 (s, 3H), 3.59 (s, 2H), 2,43 (d, J=6.8 Hz, 2H), 2.17 (m, 1H), 0.92 (d, J=6.8 Hz, 6H).

Preparation of 2.13

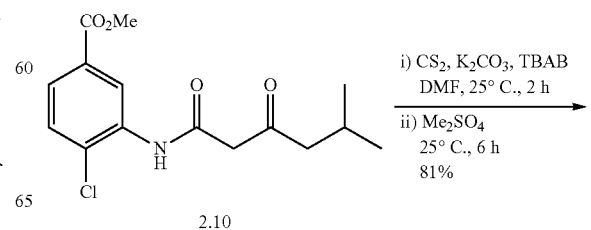

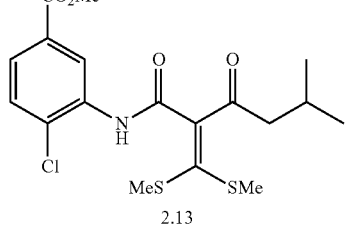

2.13

To a stirred suspension of 2.10 (340 mg, 1.09 mmol), K$_2$CO$_3$ (452 g, 3.27 mmol), and TBAB (35 mg, 0.11 mmol) in DMF (10 mL) was added carbon disulfide (0.07 mL, 1.12 mmol) at 25° C. After stirring for 2 h, dimethyl sulfate (0.23 mL, 2.40 mmol) was added dropwise over 30 min. The reaction mixture was stirred for 7 h and quenched by addition of ice water.

The aqueous layer was extracted with EtOAc, and the combined organic layers were dried over anhydrous Na$_2$SO$_4$, and concentrated in vacuo. The residue was purified by column chromatography (silica gel, hexanes/EtOAc, 4/1) to afford 2.13 as a yellow oil (367 mg, 81%): $^1$H NMR (400 MHz, CDCl$_3$) b 9.07 (s, 1H), 8.90 (s, 1H), 7.75 (dd, J=8.4, 2.4 Hz, 1H), 7.45 (d, J=8.4 Hz, 1H), 3.91 (s, 3H), 2.72 (d, J=6.8 Hz, 2H), 2.47 (s, 6H), 2.22 (m, 1H), 0.96 (d, J=6.8 Hz, 6H).

Preparation of 2.16

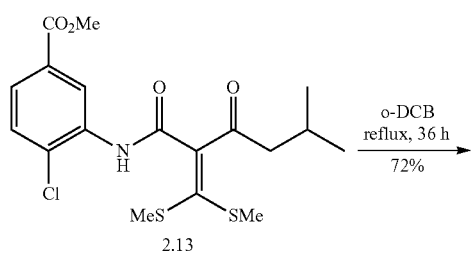

2.13

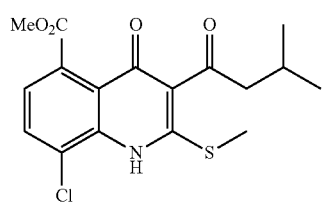

2.16

A solution of 2.13 (350 mg, 0.84 mmol) in 1,2-dichlorobenzene (8 mL) was refluxed for 16 h.

The reaction mixture was concentrated in vacuo and the residue was purified by column chromatography (silica gel, hexanes/EtOAc, 2/1) to afford 2.16 (222 mg, 72%): 1H NMR (400 MHz, CDCl$_3$) b 8.65 (s, 1H), 7.63 (d, J=8.0 Hz, 1H), 7.20 (d, J=8.0 Hz, 1H), 3.99 (s, 3H), 3.00 (d, J=6.8 Hz, 2H), 2.60 (s, 3H), 2.21 (m, 1H), 0.93 (d, J=6.8 Hz, 6H).

Preparation of 2.19

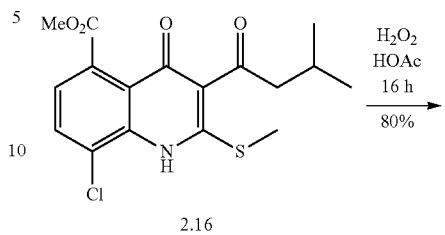

2.16

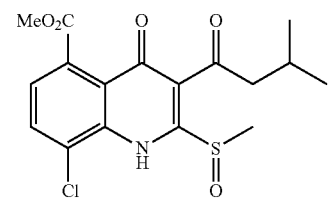

2.19

To a solution of 2.16 (202 mg, 0.60 mmol) in acetic acid (6 mL) was added hydrogen peroxide (0.15 mL, 1.50 mmol) at 25° C. After stirring for 16 h, the reaction mixture was poured into ice water and the aqueous layer was extracted with EtOAc. The combined organic layers were washed with brine and dried over anhydrous Na2SO4, and concentrated in vacuo. The residue was purified by column chromatography (silica gel, hexanes/EtOAc, 2/1) to afford 2.19 as a yellow oil (184 mg, 80%): $^1$H NMR (400 MHz, CDC$_3$) δ 11.17 (s, 1H), 7.78 (d, J=8.0 Hz, 1H), 7.33 (d, J=8.0 Hz, 1H), 4.01 (s, 3H), 3.11 (d, J=6.8 Hz, 1H), 3.08 (d, J=6.8 Hz, 1H), 3.01 (s, 3H), 2.19 (m, 1H), 0.95 (d, J=6.8 Hz, 3H), 0.94 (d, J=6.8 Hz, 3H).

Preparation of 2.22 and RE09 (2-((2,4-dichlorophenyl)amino)-3-(3-methylbutanoyl)-4-oxo-1,4-dihydroquinoline-5,8-dicarboxylic acid)

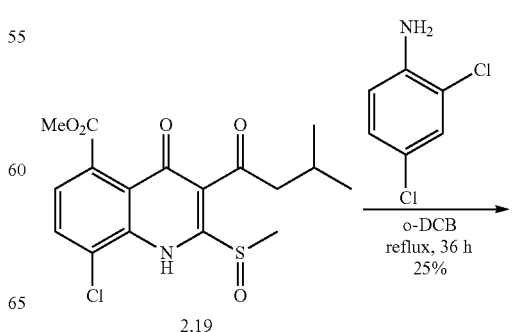

2.19

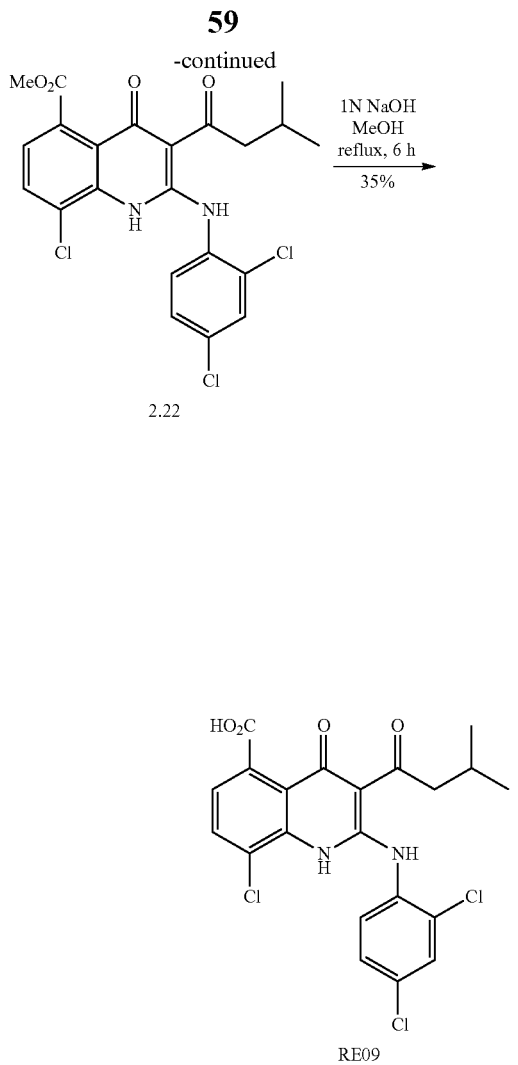

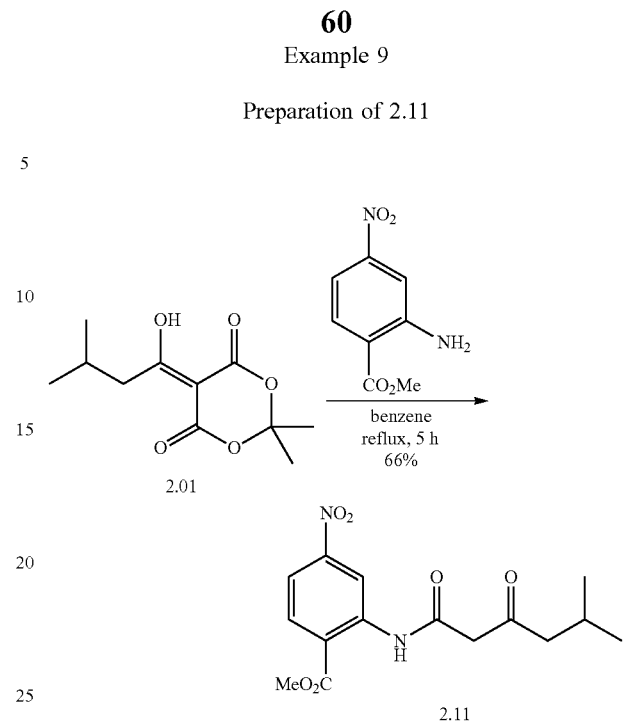

Example 9

Preparation of 2.11

To a solution of the known 2.01 (482 mg, 2.11 mmol) in benzene (10 mL) was added methyl 2-amino-4-nitrobenzoate (332 mg, 1.69 mmol) at 25° C. The reaction mixture was refluxed for 5 h and concentrated in vacuo. The residue was purified by column chromatography (silica gel, hexanes/EtOAc, 5/1) to afford 2.11 as a yellow oil (450 g, 66%): 1H NMR (400 MHz, CDCl3) δ 11.42 (s, 1H), 9.50 (d, J=2.4 Hz, 1H), 8.15 (d, J=8.8 Hz, 1H), 7.85 (dd, J=8.8, 2.4 Hz, 1H), 3.98 (s, 3H), 3.60 (s, 2H), 2.48 (d, J=6.8 Hz, 2H), 2.18 (m, 1H), 0.93 (d, J=6.8 Hz, 6H).

To a solution of 2.19 (36 mg, 0.094 mmol) in 1,2-dichlorobenzene (2 mL) was added 2,4-dichloroaniline (45 mg, 0.28 mmol) at 25° C. The reaction mixture was refluxed for 38 h and concentrated in vacuo to give a residue, which was dissolved in EtOAc. The ethyl acetate solution was washed with brine, dried over anhydrous Na$_2$SO$_4$, and concentrated in vacuo. The residue was purified by column chromatography (silica gel, hexanes/EtOAc, 4/1) to afford 2.22 as a yellow solid (11 mg, 25%): $^1$H NMR (400 MHz, CDCl$_3$) δ 13.40 (s, 1H), 8.17 (s, 1H), 7.66 (s, 1H), 7.55 (d, J=8.0 Hz, 1H), 7.46 (m, 2H), 7.13 (d, J=8.0 Hz, 1H), 4.00 (s, 3H), 3.15 (d, J=6.8 Hz, 2H), 2.45 (m, 1H), 0.99 (d, J=6.8 Hz, 6H) [Hydrolysis] To a solution of 2.22 (10 mg, 0.02 mmol) in methanol (0.5 mL) was added 1 M NaOH (0.5 mL, 0.50 mmol) at 25° C. The reaction mixture was refluxed for 6 h and 1 M HCl was added to pH 2 while the solution cooled in ice bath. The aqueous layer was extracted with EtOAc, and the combined organic layers were dried over anhydrous Na$_2$SO$_4$, and concentrated in vacuo.

The residue was purified by column chromatography (silica gel, hexanes/EtOAc/HOAc, 3/1/0.01) to afford RE09 as a yellow oil (6 mg, 60%): $^1$H NMR (400 MHz, CDCl$_3$) δ 12.92 (s, 1H), 8.70 (s, 1H), 8.43 (s, 1H), 7.73 (d, J=8.0 Hz, 1H), 7.70 (s, 1H), 7.49 (s, 2H), 3.13 (d, J=6.4 Hz, 2H), 2.29 (m, 1H), 1.00 (d, J=6.4 Hz, 6H).

Preparation of 2.14

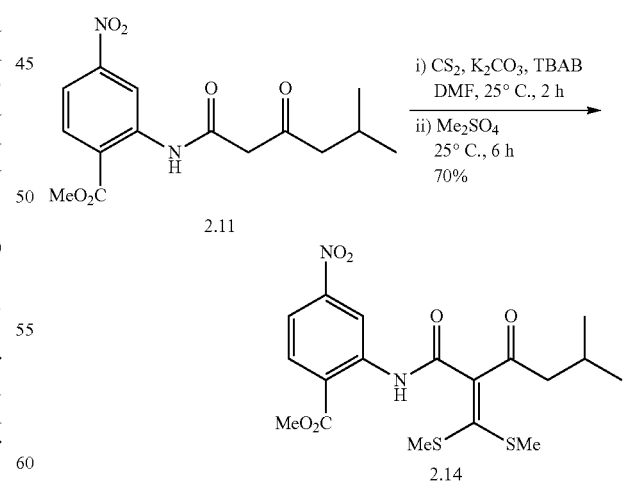

To a stirred suspension of 2.11 (175 mg, 0.54 mmol), K$_2$CO$_3$ (224 g, 1.62 mmol), and TBAB (17 mg, 0.054 mmol) in DMF (6 mL) was added carbon disulfide (0.04 mL, 0.59 mmol) at 25° C. After stirring for 2 h, dimethyl sulfate (0.11 mL, 1.19 mmol) was added dropwise over 30 min. The reaction mixture was stirred for 10 h and quenched by addition of ice water. The aqueous layer was extracted with EtOAc, and the combined organic layers were dried over anhydrous Na$_2$SO$_4$, and concentrated in vacuo. The residue was purified by column chromatography (silica gel, hexanes/EtOAc, 3/1) to afford 2.14 as a yellow oil (161 mg, 70%): $^1$H NMR (400 MHz, CDCl$_3$) δ 11.34 (s, 1H), 9.63 (d, J=2.0 Hz, 1H), 8.20 (d, J=8.8 Hz, 1H), 7.90 (dd, J=8.8, 2.0 Hz, 1H), 3.98 (s, 3H), 2.64 (d, J=6.8 Hz, 2H), 2.44 (s, 6H), 2.22 (m, 1H), 0.93 (d, J=6.8 Hz, 6H).

Preparation of 2.17

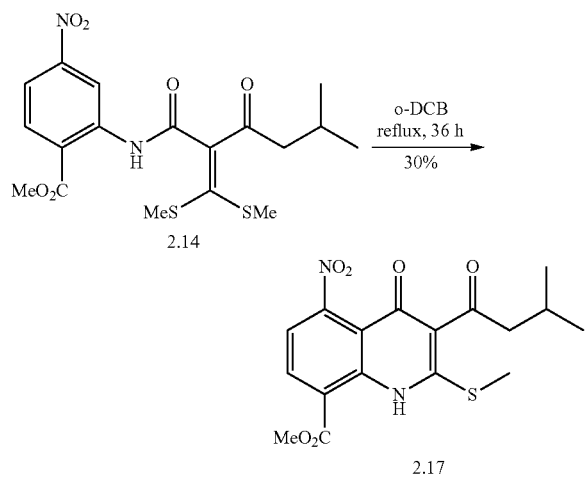

A solution of 2.14 (141 mg, 0.33 mmol) in 1,2-dichlorobenzene (3 mL) was refluxed for 36 h. The reaction mixture was concentrated in vacuo and the residue was purified by column chromatography (silica gel, hexanes/EtOAc, 2/1) to afford 2.17 (38 mg, 30%): $^1$H NMR (400 MHz, CDCl$_3$) δ 12.33 (s, 1H), 8.42 (d, J=8.8 Hz, 1H), 7.27 (d, J=8.8 Hz, 1H), 4.07 (s, 3H), 2.99 (d, J=6.8 Hz, 2H), 2.64 (s, 3H), 2.23 (m, 1H), 0.93 (d, J=6.8 Hz, 6H).

Preparation of 2.20

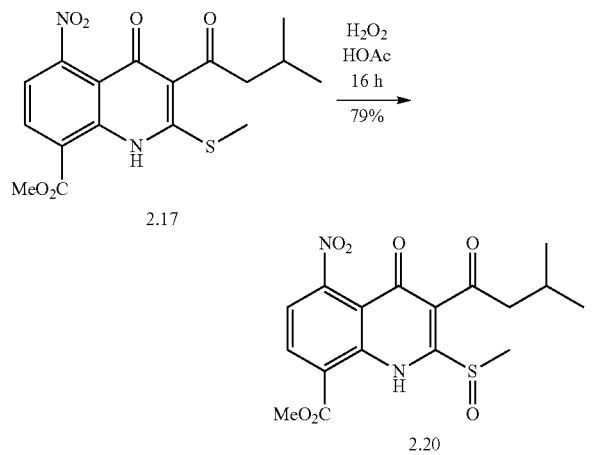

To a solution of 2.17 (27 mg, 0.07 mmol) in acetic acid (1 mL) was added hydrogen peroxide (0.018 mL, 0.18 mmol) at 25° C. After stirring for 16 h, the reaction mixture was poured into ice water and the aqueous layer was extracted with EtOAc. The combined organic layers were washed with brine and dried over anhydrous Na$_2$SO$_4$, and concentrated in vacuo. The residue was purified by column chromatography (silica gel, hexanes/EtOAc, 1/1) to afford 2.20 as a yellow oil (22 mg, 79%): $^1$H NMR (400 MHz, CDCl$_3$) δ 13.61 (s, 1H), 8.56 (d, J=8.4 Hz, 1H), 7.44 (d, J=8.4 Hz, 1H), 4.11 (s, 3H), 3.09 (d, J=6.8 Hz, 1H), 3.08 (d, J=6.8 Hz, 1H), 3.04 (s, 3H), 2.20 (m, 1H), 0.94 (t, J=6.8 Hz, 6H).

Preparation of 2.13 and RE10 (2-((2,4-dichlorophenyl)amino)-3-(3-methylbutanoyl)-5-nitro-4-oxo-1,4-dihydroquinoline-8-carboxylic acid)

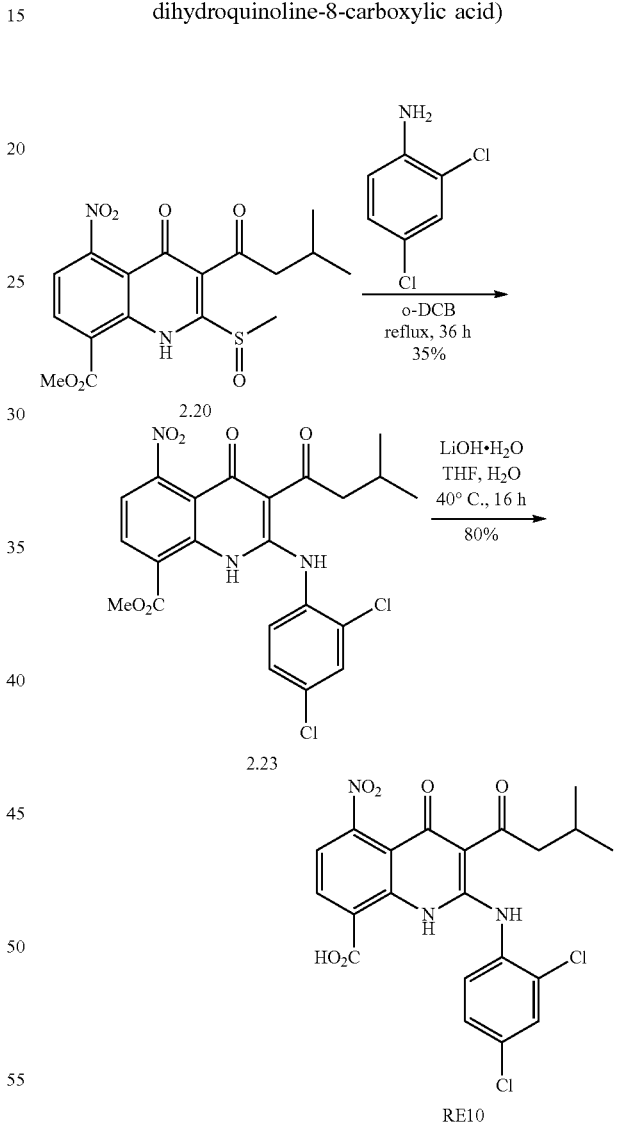

To a solution of 2.20 (14 mg, 0.035 mmol) in 1,2-dichlorobenzene (1 mL) was added 2,4-dichloroaniline (17 mg, 0.11 mmol) at 25° C. The reaction mixture was refluxed for 36 h and concentrated in vacuo to give a residue, which was dissolved in EtOAc. The ethyl acetate solution was washed with brine, dried over anhydrous Na$_2$SO$_4$, and concentrated in vacuo. The residue was purified by column chromatography (silica gel, hexanes/EtOAc, 3/1) to afford 2.23 as a yellow solid (6 mg, 35%): $^1$H NMR (400 MHz, CDCl$_3$) δ 13.32 (s, 1H), 11.74 (s, 1H), 8.28 (d, J=8.4 Hz, 1H), 7.65 (d, J=2.0 Hz, 1H), 7.60-7.50 (m, 2H), 7.16 (d, J=8.4 Hz, 1H), 3.91 (s, 3H), 3.14 (d, J=6.8 Hz, 2H), 2.67 (m, 1H), 0.98 (d, J=6.8 Hz, 6H) [Hydrolysis] To a solution of 2.23 (5 mg, 0.01 mmol) in THF (0.3 mL) was added a solution of LiOH·H$_2$O (4 mg, 0.10 mmol) in H$_2$O (0.1 mL). The resulting mixture was stirred at 40° C. for 16 h. 2 N HCl (1 mL) was added and the aqueous layer was extracted with EtOAc. The combined organic layers were dried over anhydrous Na$_2$SO$_4$, and concentrated in vacuo.

The residue was purified by column chromatography (silica gel, hexanes/EtOAc/HOAc, 1/1/0.01) to afford RE10 as a yellow oil (4 mg, 80%): $^1$H NMR (400 MHz, CDCl$_3$) δ 13.23 (s, 1H), 11.50 (s, 1H), 8.42 (d, J=8.4 Hz, 1H), 7.64 (s, 1H), 7.44 (m, 2H), 7.21 (d, J=8.4 Hz, 1H), 3.13 (d, J=6.8 Hz, 2H), 2.26 (m, 1H), 0.98 (d, J=6.8 Hz, 6H).

Example 10

Preparation of RE11 (5-amino-8-chloro-2-((2,4-dichlorophenyl)amino)-3-(3-methylbutanol) qinolin-4(1H)-one)

2H), 7.16 (d, J=8.8 Hz, 1H), 6.79 (bs, 2H), 6.29 (d, J=8.8 Hz, 1H), 3.14 (d, J=6.4 Hz, 2H), 2.30 (m, 1H), 1.01 (d, J=6.4 Hz, 6H).

Example 10A

Preparation of RE12 (8-chloro-2-((2,4-dichlorophenyl)amino)-3-(3-methylbutanoyl)-5-nitroquinolin-4(1H)-one)

Compound RE12 is prepared essentially as shown in Scheme 4. The acyl Meldrum's acid 2.24 was treated with 2-chloro-5-nitroanline under reflux to give the β-oxo amide 2.25. Subsequent transformation into acyl(arylcarbamoyl) ketene dithioacetal 2.26 followed by cyclization and oxidation provided the sulfoxide 2.27. Final coupling of the sulfoxide 2.28 with aniline completed the synthesis of RE12.

Example 11

Preparation of RE13 (5-amino-8-chloro-2-((2,4-dichlorophenyl)amino)-3-(3-methylbutanoyl)quinolin-4(1H)-one

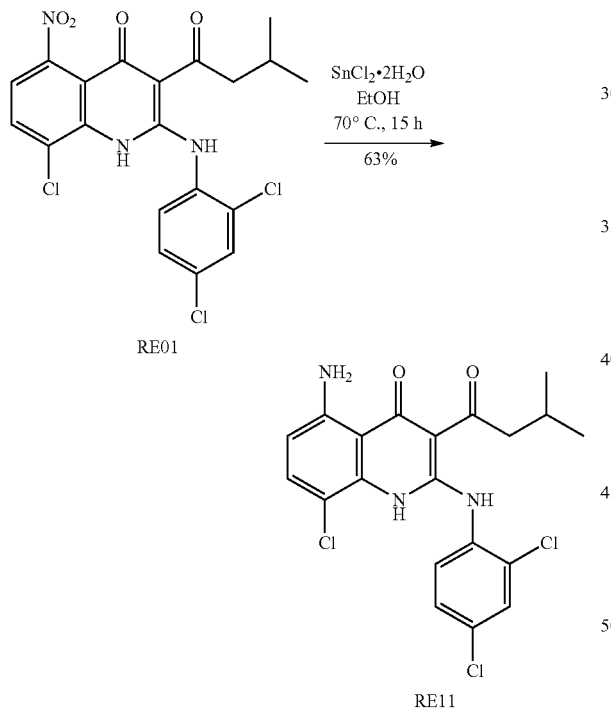

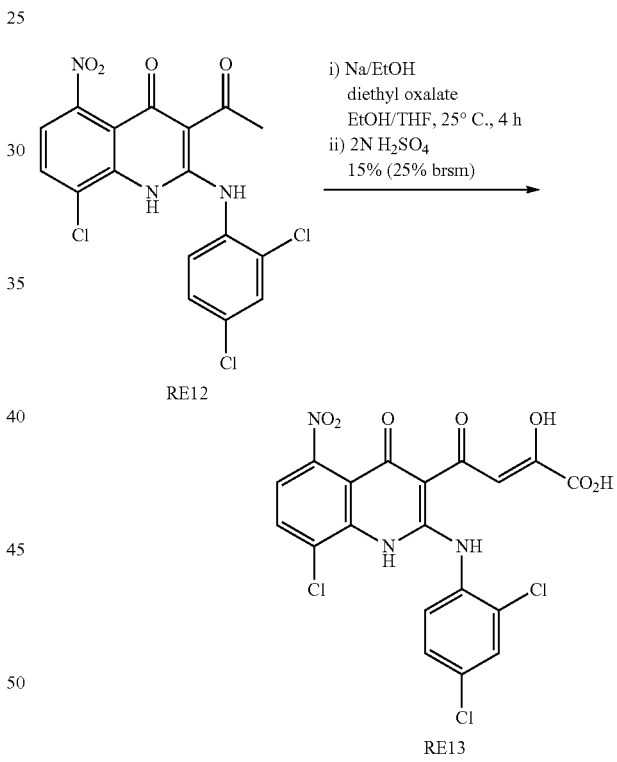

To a solution of RE01 (9 mg, 0.019 mmol) in ethanol (0.5 mL) was added tin chloride dihydrate (13 mg, 0.057 mmol) at 25° C. The reaction mixture was heated to 70° C. overnight. The solution was poured into ice water and the pH was made slightly basic by addition of aqueous NaHCO$_3$. The aqueous layer was extracted with EtOAc, and the combined organic layers were dried over anhydrous Na$_2$SO$_4$, and concentrated in vacuo.

The residue was purified by column chromatography (silica gel, hexanes/EtOAc, 8/1) to afford RE11 as a yellow oil (5 mg, 63%): $^1$H NMR (400 MHz, CDCl$_3$) δ 13.28 (s, 1H), 18.09 (s, 1H), 7.63 (d, J=2.0 Hz, 1H), 7.47-7.41 (m, To a cooled (0° C.) solution of sodium (22 mg, 0.94 mmol) in absolute EtOH (0.3 mL) was added dropwise a mixture of diethyl oxalate (0.012 mL, 0.094 mmol) and RE12 (20 mg, 0.047 mmol) in THF (0.3 mL). The reaction mixture was stirred at 25° C. for 4 h and water was added with stirring and the solvent was removed under reduced pressure. The residue was poured into 2 N H$_2$SO$_4$, extracted with Et$_2$O, dried over anhydrous Na$_2$SO$_4$, and concentrated in vacuo. The residue was purified by column chromatography (silica gel, CH$_2$Cl$_2$/MeOH/NH$_4$OH, 6/4/0.5) to afford RE13 as a yellow oil (3.5 mg, 15%, 25% brsm): $^1$H NMR (400 MHz, CD$_3$OD) δ 6.10 (d, J=7.6 Hz, 1H), 6.02 (m, 1H), 5.88 (m, 2H), 5.57 (d, J=7.6 Hz, 1H), 4.80 (s, 1H).

Example 12

Preparation of RE14 (8-chloro-2-((2,4-dichlorophenyl)amino)-3-(1-(hydroxyimino)ethyl)-5-nitroquinolin-4(1H)-one)

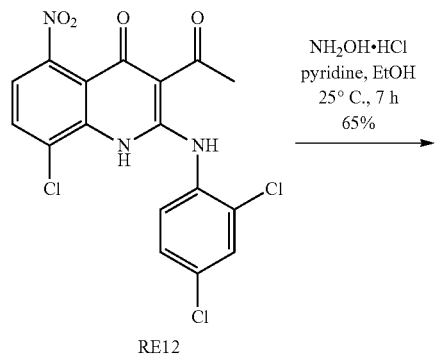

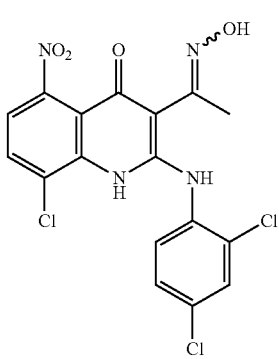

To a solution of RE12 (19 mg, 0.045 mmol) in EtOH (1 mL) and pyridine (0.5 mL) was added hydroxylamine hydrochloride (6 mg, 0.09 mmol) at 25° C. The reaction mixture was stirred at 25° C. for 7 h and concentrated in vacuo. The residue was dissolved in CH$_2$Cl$_2$ and washed successively with aqueous 5% HCl, H$_2$O, and brine. The combined organic layers were dried over anhydrous Na$_2$SO$_4$, and concentrated in vacuo. The residue was purified by column chromatography (silica gel, hexanes/EtOAc, 1/2) to afford RE14 as a yellow oil (13 mg, 65%).

Example 13

Preparation of RE15 (8-chloro-2-((2,4-dichlorophenyl)amino)-3-(1-hydroxyethyl)-5-nitroquinolin-4(1H)-one)

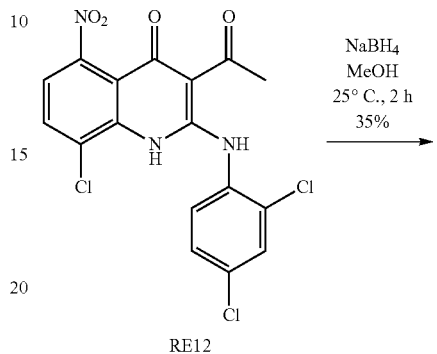

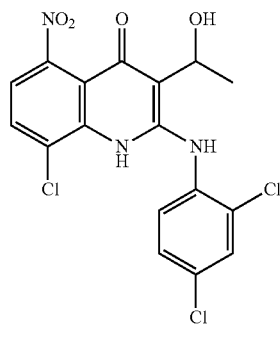

To a solution of RE12 (19 mg, 0.045 mmol) in MeOH (1 mL) was added NaBH$_4$ (2 mg, 0.054 mmol) at 25° C. The reaction mixture was stirred at 25° C. for 2 h, quenched by addition of saturated aqueous NaHCO$_3$ and extracted with EtOAc. The combined organic layers were washed with brine, dried over anhydrous Na$_2$SO$_4$, and concentrated in vacuo.

The residue was purified by column chromatography (silica gel, hexanes/EtOAc, 3/1) to afford RE15 (7 mg, 35%). $^1$H NMR (400 MHz, CDC$_3$) b 9.42 (s, 1H), 8.42 (s, 1H), 7.60 (m, 1H), 7.44-7.39 (m, 3H), 7.04 (m, 1H), 5.59 (m, 1H), 1.58 (s, 3H).

Example 13A

Compounds RE16-RE39, shown below in Table 2, are prepared essentially according to the synthetic methodology described herein, Examples 1-13 and Schemes 1-6, and/or by using methodology well known in the art.

TABLE 2

| Compound | Structure | Chemical Name |
|---|---|---|
| RE16 | 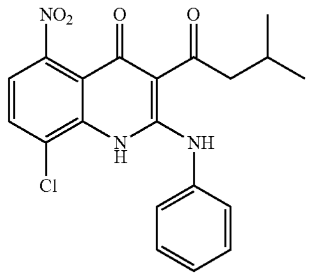 | 8-chloro-3-(3-methylbutanoyl)-5-nitro-2-(phenylamino)quinolin-4(1H)-one |
| RE17 | 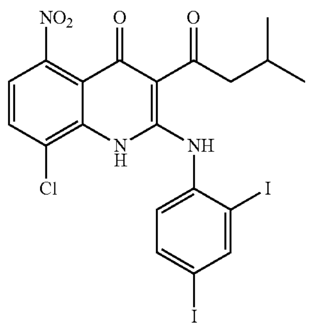 | 8-chloro-2-((2,4-diiodophenyl)amino)-3-(3-methylbutanoyl)-5-nitroquinolin-4(1H)-one |
| RE18 | 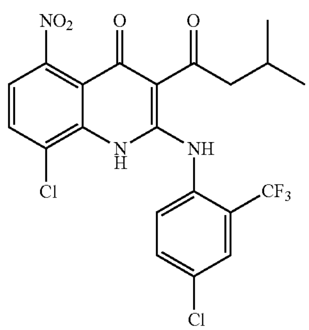 | 8-chloro-2-((4-chloro-2-(trifluoromethyl)phenyl)amino)-3-(3-methylbutanoyl)-5-nitroquinolin-4(1H)-one |
| RE19 | 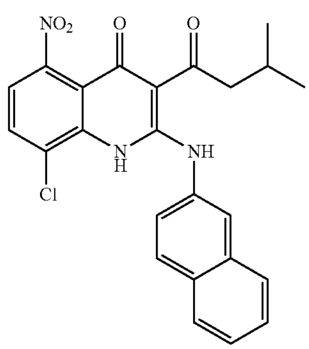 | 8-chloro-3-(3-methylbutanoyl)-2-(naphthalen-2-ylamino)-5-nitroquinolin-4(1H)-one |
| RE20 | 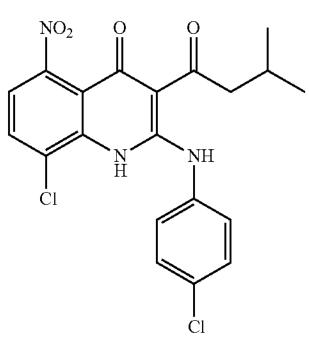 | 8-chloro-2-((4-chlorophenyl)amino)-3-(3-methylbutanoyl)-5-nitroquinolin-4(1H)-one |

TABLE 2-continued

| Compound | Structure | Chemical Name |
|---|---|---|
| RE21 | 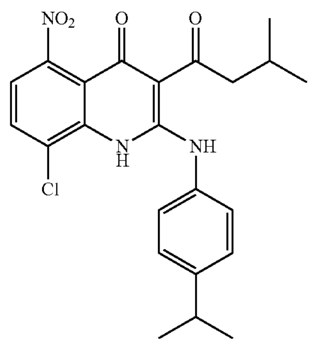 | 8-chloro-2-((4-isopropylphenyl)amino)-3-(3-methylbutanoyl)-5-nitroquinolin-4(1H)-one |
| RE22 | 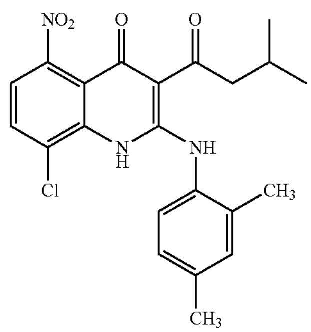 | 8-chloro-2-((2,4-dimethylphenyl)amino)-3-(3-methylbutanoyl)-5-nitroquinolin-4(1H)-one |
| RE23 | 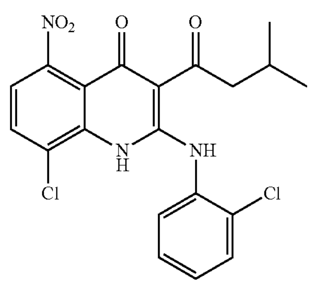 | 8-chloro-2-((2-chlorophenyl)amino)-3-(3-methylbutanoyl)-5-nitroquinolin-4(1H)-one |
| RE24 | 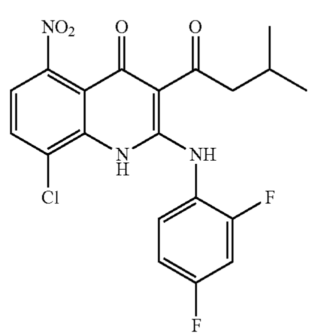 | 8-chloro-2-((2,4-difluorophenyl)amino)-3-(3-methylbutanoyl)-5-nitroquinolin-4(1H)-one |

TABLE 2-continued

| Compound | Structure | Chemical Name |
|---|---|---|
| RE25 | 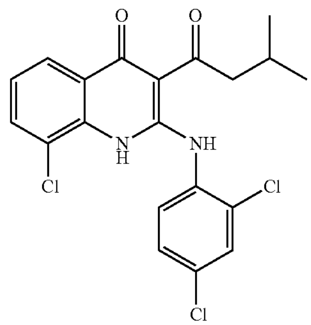 | 8-chloro-2-((2,4-dichlorophenyl)amino)-3-(3-methylbutanoyl)quinolin-4(1H)-one |
| RE26 | 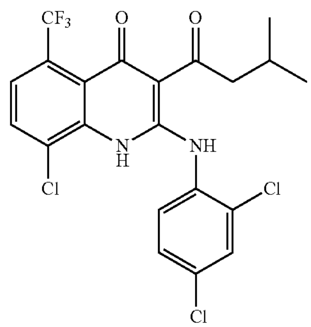 | 8-chloro-2-((2,4-dichlorophenyl)amino)-3-(3-methylbutanoyl)-5-(trifluoromethyl)quinolin-4(1H)-one |
| RE27 | 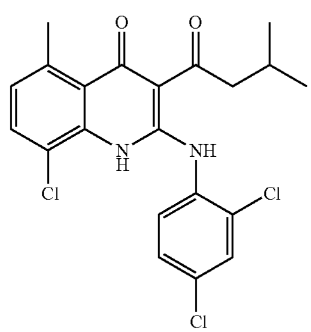 | 8-chloro-2-((2,4-dichlorophenyl)amino)-5-methyl-3-(3-methylbutanoyl)quinolin-4(1H)-one |
| RE28 | 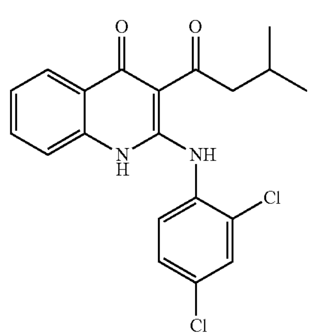 | 2-((2,4-dichlorophenyl)amino)-3-(3-methylbutanoyl)quinolin-4(1H)-one |

TABLE 2-continued

| Compound | Structure | Chemical Name |
|---|---|---|
| RE29 | 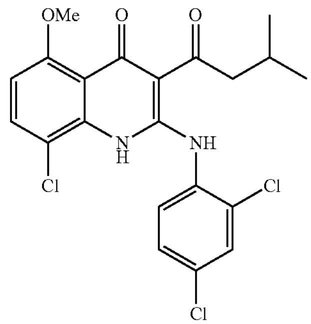 | 8-chloro-2-((2,4-dichlorophenyl)amino)-5-methoxy-3-(3-methylbutanoyl)quinolin-4(1H)-one |
| RE30 | 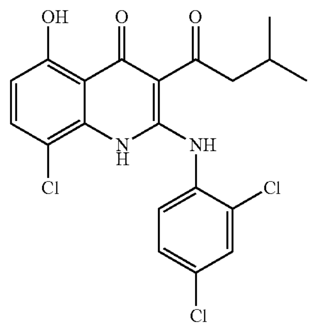 | 8-chloro-2-((2,4-dichlorophenyl)amino)-5-hydroxy-3-(3-methylbutanoyl)quinolin-4(1H)-one |
| RE31 | 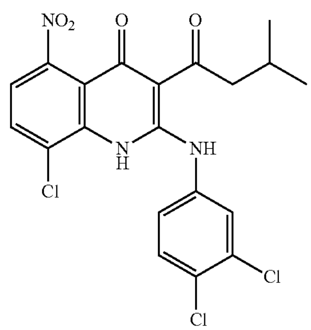 | 8-chloro-2-((3,4-dichlorophenyl)amino)-3-(3-methylbutanoyl)-5-nitroquinolin-4(1H)-one |
| RE32 | 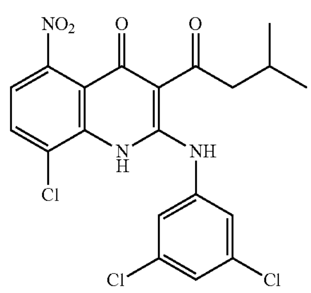 | 8-chloro-2-((3,5-dichlorophenyl)amino)-3-(3-methylbutanoyl)-5-nitroquinolin-4(1H)-one |
| RE33 | 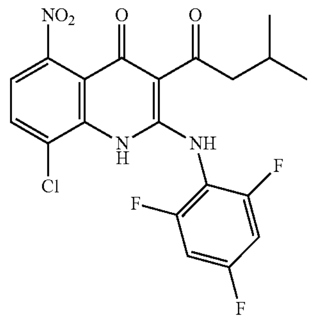 | 8-chloro-3-(3-methylbutanoyl)-5-nitro-2-((2,4,6-trifluorophenyl)amino)quinolin-4(1H)-one |

TABLE 2-continued

| Compound | Structure | Chemical Name |
|---|---|---|
| RE34 | 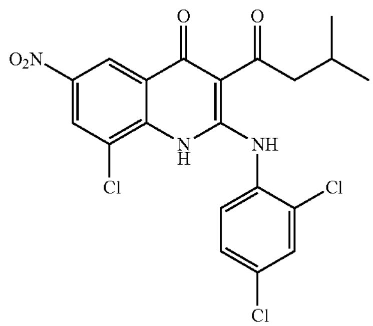 | 8-chloro-2-((2,4-dichlorophenyl)amino)-3-(3-methylbutanoyl)-6-nitroquinolin-4(1H)-one |
| RE35 | 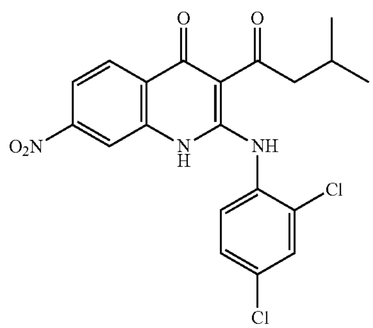 | 2-((2,4-dichlorophenyl)amino)-3-(3-methylbutanoyl)-7-nitroquinolin-4(1H)-one |
| RE36 | 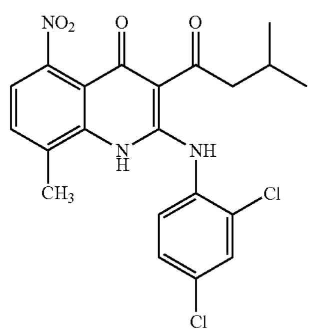 | 2-((2,4-dichlorophenyl)amino)-8-methyl-3-(3-methylbutanoyl)-5-nitroquinolin-4(1H)-one |
| RE37 | 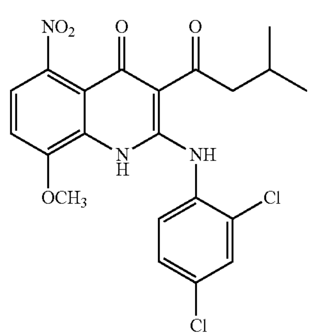 | 2-((2,4-dichlorophenyl)amino)-8-methoxy-3-(3-methylbutanoyl)-5-nitroquinolin-4(1H)-one |

TABLE 2-continued

| Compound | Structure | Chemical Name |
|---|---|---|
| RE38 | 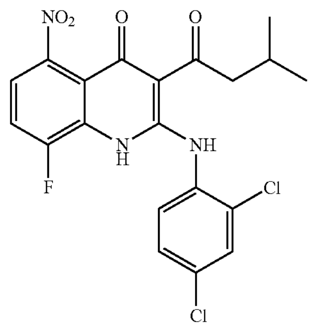 | 2-((2,4-dichlorophenyl)amino)-8-fluoro-3-(3-methylbutanoyl)-5-nitroquinolin-4(1H)-one |
| RE39 | 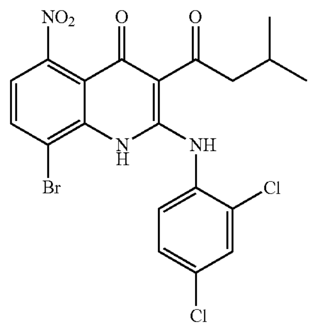 | 8-bromo-2-((2,4-dichlorophenyl)amino)-3-(3-methylbutanoyl)-5-nitroquinolin-4(1H)-one |

Biological Examples

Bacterial Strains and Growth Media: BL21 Star™ (DE3) E. coli (ThermoFisher Scientific) and K12 JM109 E. coli (New England Biolabs) cells were used for protein expression and the gapped plasmid TLS assay, respectively. Selection and growth of E. coli was performed in the Lysogeny Broth (LB) medium supplemented with the appropriate antibiotics [100 μg/mL Ampicillin for the pET15b (Novagen/Sigma-Aldrich) or pUC19 (NEB) vectors or 50 μg/mL Streptomycin for the pCDFDuet-1 (Novagen/Sigma-Aldrich) vector] at 37° C.

Mammalian Cell Culturing: HT1080 cells (male, fibrosarcoma epithelial cells purchased from ATCC) were grown at 37° C. with 5% $CO_2$ in RPMI 1640 (Gibco), 10% (v/v) FBS (HyClone), and 1% Penicillin-Streptomycin antibiotic (Corning). A375 cells (female, malignant melanoma; kindly gifted by Oliver Jonas, Koch Institute, MIT), KP cells (female, mouse $Kras^{G12D}$;$p53^{-/-}$ lung adenocarcinoma; kindly gifted by Tyler Jackson Laboratory), and MEF (Mouse Embryonic Fibroblasts, sex unspecified in the original publication) wild-type ($Rev1^{+/+}$) and Rev1 knockout ($Rev1^{-/-}$) cells were grown at 37° C. with 5% $CO_2$ in DMEM (Gibco), 10% (v/v) FBS (HyClone), and 1% Penicillin-Streptomycin antibiotic (Corning). LNCap cells (male, human prostate adenocarcinoma; kindly gifted by Michael Yaffe Lab, Koch Institute, MIT) were also grown at 37° C. with 5% $CO_2$ in RPMI 1640 (-phenol) (Gibco), 10% (v/v) FBS (HyClone), and 1% Penicillin-Streptomycin antibiotic (Corning). AG01522 cells (male, human primary cells purchased from Coriell Institute) were grown at 37° C. with 5% $CO_2$ in MEM (-Glutamine; +Earle's Salts; +Non-Essential Amino Acids) (Gibco) and 20% (v/v) FBS (HyClone). All cells were trypsinized using 0.25% Trypsin-EDTA (ThermoFisher) for passaging.

Mice: Six- to eight-week-old, female NCRNU-F nude mice (immunodeficient; nomenclature: CrTac:NCr-Foxn1$^{nu}$; genotype: homozygous sp/sp) were purchased from Taconic Biosciences for experimentation. All mice were drug and test naïve and were not involved in any previous procedure. All mice were housed in micro-isolator cages in the animal research facility of the MIT Division of Comparative Medicine (DCM), which is fully accredited by the AAALAC (Animal Welfare Assurance number A-3125) and meets NIH standards as set forth in the "Guide for Care and Use of Laboratory Animals" (DHHS). The MIT animal facility is maintained under specific pathogen free (SPF) conditions.

Quantification and Statistical Analysis: Cell culture results were statistically analyzed using one-way analysis of variance (ANOVA) followed by Tukey's post hoc tests or with the Student's t-test. For murine xenograft tumor studies, differences of tumor volumes and survival curves of tumor-bearing mice between treatment groups were analyzed by the Welch's t-test and the Mantel-Cox log-rank test, respectively. Multiple biological replicates (n≥3) were performed in all cases, unless otherwise noted. Variation is indicated using standard error of the mean (SEM) and presented as mean±SEM unless otherwise noted.

Significance was defined as *$p<0.05$ or **$p<0.01$. Statistical details of individual experiments can be found in the corresponding Figure Legends.

Example 14: Molecular Cloning and Protein Purification

The gene encoding the mouse POL $_\kappa$ RIR (K564-N577), a di-glycine linker, and the mouse REV1 CTD (F1150-T1249) was synthesized and cloned into a modified pET15b vector as the C-terminal fusion protein to the solubility tag His$_{10}$-GB1 separated by a TEV protease site. The FLAG-tagged chimeric POL $_\kappa$ RIR-REV1 CTD was generated by inserting the FLAG tag immediately after the TEV protease site. Both expression constructs were verified by DNA sequencing. The chimeric POL $_\kappa$ RIR-REV1 CTD and FLAG-tagged POL $_\kappa$ RIR-REV1 CTD were expressed in BL21 Star™ (DE3) *E. coli* cells (ThermoFisher Scientific). Cells were induced at O.D.$_{600}$ of 0.5 with 0.1 mM isopropyl 1-thio-β-D-galactopyranoside (IPTG) at 18° C. overnight. Harvested cells were lysed in a buffer containing 50 mM sodium phosphate (pH 8.0), 300 mM sodium chloride, and 0.1% p-mercaptoethanol using a French Pressure cell at 1250 psi. His$_{10}$-GB1-tagged REV1 proteins were purified using Ni-NTA affinity chromatography (HisPur Ni-NTA, Pierce Biotechnology) and eluted with the lysis buffer containing 300 mM imidazole. Elution fractions were combined and exchanged into the FPLC buffer containing 25 mM HEPES (pH 7.5), 100 mM KCl, and 2 mM tris(2-carboxyethyl)phosphine (TCEP). Following TEV protease cleavage (1:20 molar ratio, 4 hours at room temperature) and a second Ni-NTA column to remove the His$_{10}$-GB1 tag, POL $_\kappa$ RIR-REV1 CTD and its FLAG-tagged counterpart were further purified to homogeneity by size-exclusion chromatography (Superdex 200, GE Healthcare Life Sciences) in the FPLC buffer.

Codon-optimized genes encoding mouse His$_8$-REV7 containing a stabilizing R124A mutation and mouse REV3L (L1845-D1895) were synthesized, cloned into the pCDF-Duet-1 vector, and verified by DNA sequencing. His$_8$-tagged REV7/3 was expressed in BL21 Star™ (DE3) cells (ThermoFisher Scientific). Cells were induced at O.D.$_{600}$ of 0.5 with 1 mM IPTG at 37° C. for 6 hours. After lysing cells in a buffer containing 50 mM sodium phosphate (pH 8.0), 300 mM sodium chloride, and 0.1% p-mercaptoethanol using a French Pressure cell at 1250 psi, the His$_8$-REV7/3 complex was purified by Ni-NTA chromatography (HisPur Ni-NTA, Pierce Biotechnology) and eluted with the lysis buffer containing 300 mM imidazole.

The eluted His$_8$-REV7/3 complex was further purified to homogeneity by size-exclusion chromatography (Superdex 200; GE Healthcare Life Sciences) in a buffer containing 25 mM HEPES (pH 7.5), 100 mM KCl and 2 mM TCEP.

Example 15: Inhibition of the REV1 CTD-REV7/3 Interaction by the AlphaScreen Assay The FLAG-tagged mouse POL $_\kappa$-REV1 CTD was diluted in PBS containing 1 mM Tris(2-carboxyethyl)phosphine (TCEP) and 0.005% Tween-20 at a final protein concentration of 1 nM and transferred to individual wells of a 96-well, half-area, white opaque plate (PerkinElmer). Serially diluted RE01 stock solutions in 50% DMSO were added to the wells to yield final inhibitor concentrations of 0-25 μM in 2% DMSO. After 30 min incubation, anti-FLAG Donor Beads (PerkinElmer) were added to a final concentration of 20 ng/μL to individual wells and incubated for an hour. His$_8$-tagged mouse REV7/3 was subsequently added to the reaction mixture to a final concentration of 10 nM and incubated for 30 min. Anti-His Acceptor Beads (PerkinElmer) were added to a final concentration of 20 ng/μL and incubated for an hour. The chemiluminescent signals were observed with a PerkinElmer Enspire Reader at the excitation wavelength of 680 nm and detection wavelength of 615 nm.

Figure 1B:
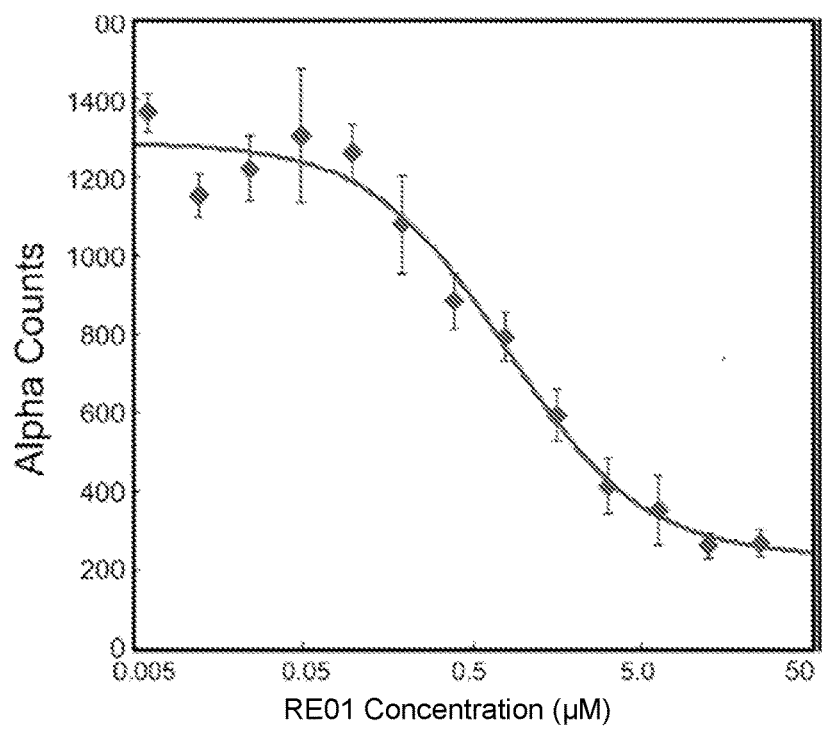
FIG. 1B is a graph showing dose-dependent inhibition of the Rev1 CTD-Rev7 interaction by RE01 as determined using the AlphaScreen™ assay described in Example 15.
Figure 2A:
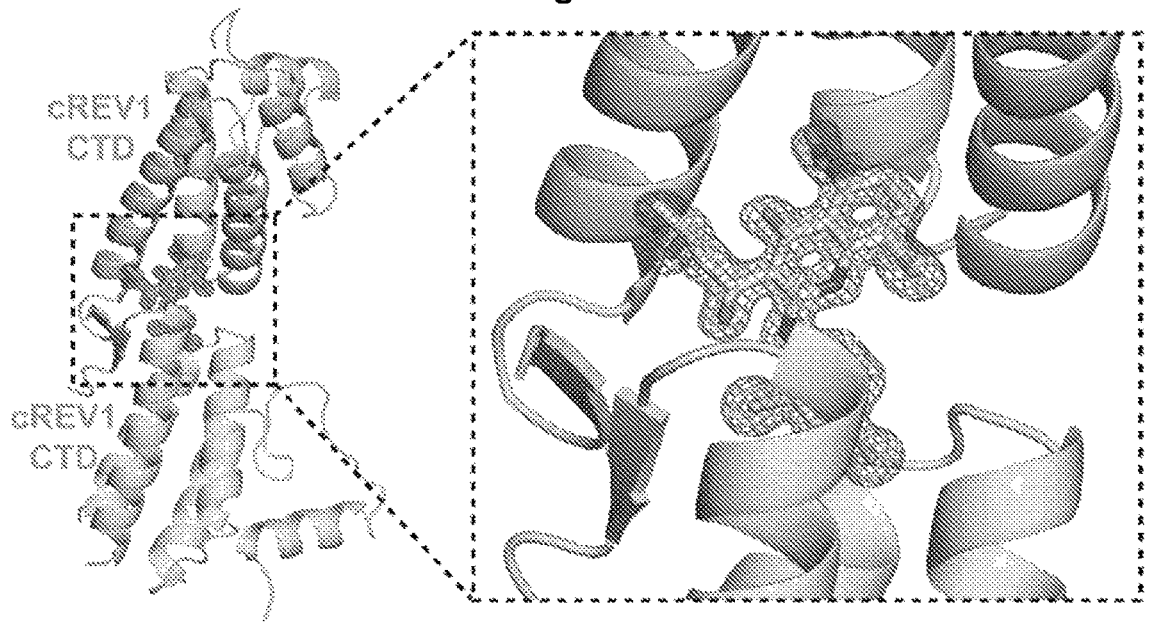
FIG. 2A is an illustration showing the structure of the cREV1 CTD/RE01 complex. Proteins are shown in the cartoon model, with protomer A colored in green and protomer B colored in cyan. RE01 is shown in the stick model, with the purple mesh representing the inhibitor omit map (2mFo-DFc) contoured at 1.0σ.
Figure 2B:
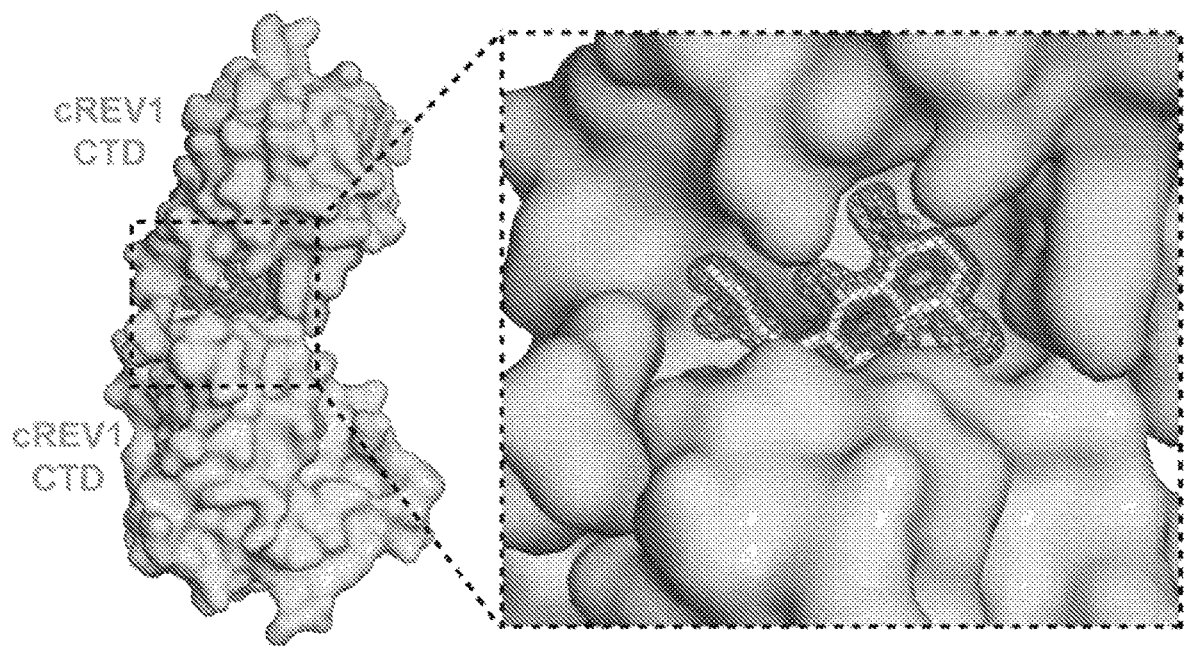
FIG. 2B is an illustration showing the surface representation of the cREV1 CTD/RE01 complex, illustrating the formation of a large ligand cavity at the dimeric REV1 CTD interface and the near encapsulation of RE01 within the cavity.
Figure 2C:
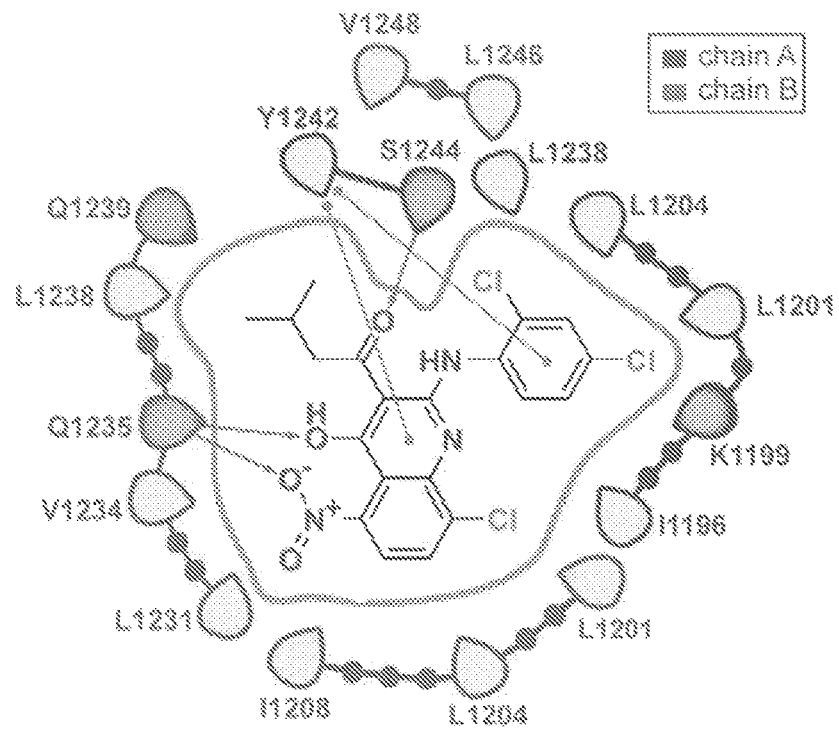
FIG. 2C is an illustration showing interactions of RE01 with REV1 CTD residues. Denoted residue numbers correspond to the full-length REV1 protein.
Figure 2D:
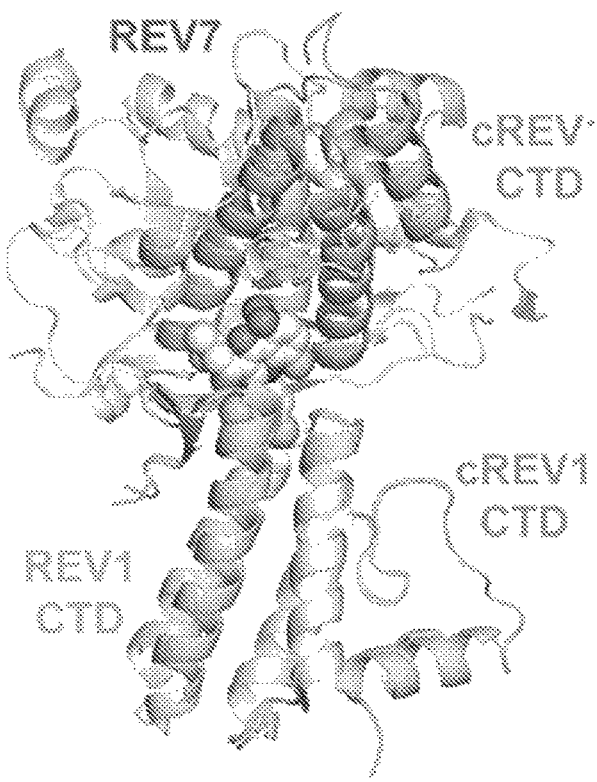
FIG. 2D is an illustration depicting superimposition of the RE01-bound cREV1 CTD dimer (colored in green and cyan) with the POL $_K$ RIR-REV1 CTD-REV7/3 translesionsome complex (colored in grey and pale cyan), illustrating the blockage of the REV1-REV7 interaction in the RE01-bound REV1 complex.
Figure 2E:
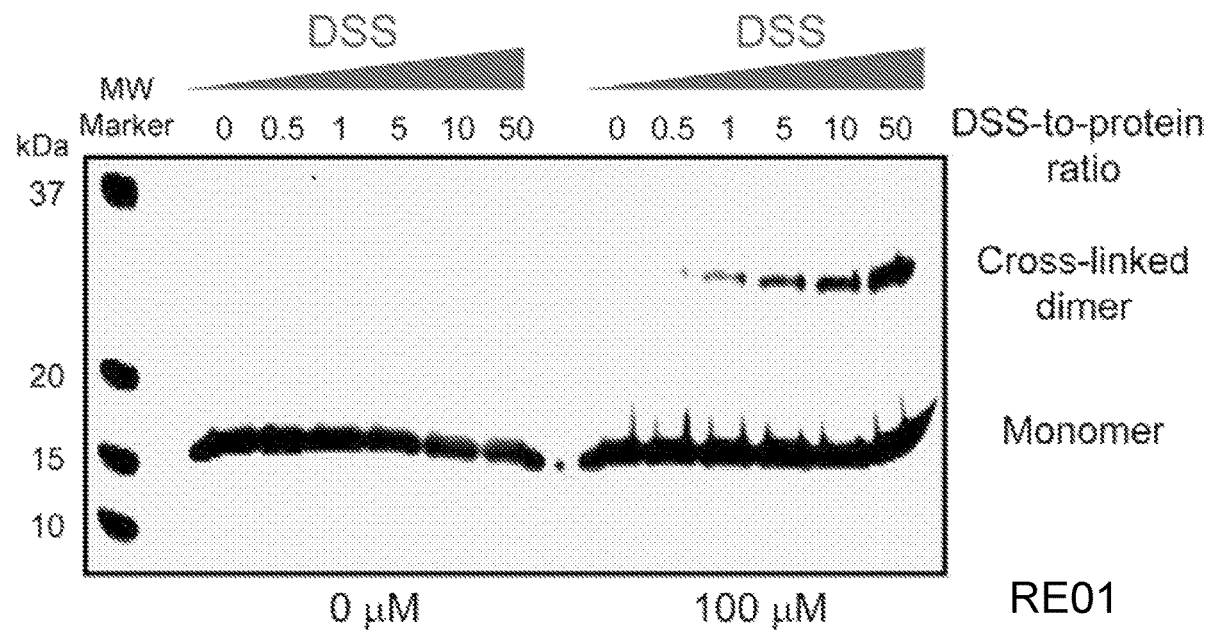
FIG. 2E is a western blot showing that binding of RE01 promotes the dimerization of the REV1 CTD in solution.

Fitting of the inhibition curve (FIG. 1B) yields an IC$_{50}$ value of 0.78 μM+/−0.16 μM for compoiund RE01. Error bars represent standard error (n=3).

Example 16: Compound Screening Using ELISA Assay

The ELISA assay for probing the REV1 CTD-REV7 interaction was carried out by immobilizing 50 nM His$_8$-tagged REV7/3 in 200 μL phosphate-buffered saline (PBS, Gibco) containing 0.2% BSA in a Ni-NTA coated 96-well plate (HisSorb, Qiagen) for 30 minutes. Unbound His$_8$-tagged REV7/3 was removed by washing the wells four times with PBS containing 0.05% Tween-20. In parallel, 80 nM FLAG-tagged POL $_\kappa$ RIR-REV1 CTD was pre-incubated with 10 μM small molecules in 200 μL PBS containing 2% DMSO for 30 minutes before transferring to the His$_8$-REV7/3 coated wells. After incubation for 30 minutes, the wells were washed four times with PBS containing 0.05% Tween-20 to remove the unbound FLAG-tagged POL $_\kappa$ RIR-REV1 CTD. A solution of the anti-FLAG horseradish peroxidase (HRP)-conjugated antibody (Sigma-Aldrich) in PBS containing 0.2% BSA was then added to the wells. After incubating for 1 hour, the antibody was washed off four times with PBS containing 0.05% Tween-20. The 3,3′,5,5′-tetramethylbenzedine (TMB) substrate (SureBlue TMB, Seracare) was added to the wells. After incubation of 20-30 minutes, the reaction was quenched with 1 M HCl. A SpectraMax plate reader (Molecular Devices) was used to measure absorbance at 450 nm.

The IC$_{50}$ values for several exemplary compounds useful in the methods of the invention are listed below. Their relative activities are shown in Table 3 below, where A represents a ratio of test compound IC$_{50}$ to RE01 IC$_{50}$ of less than 0.8; B represents a ratio of test compound IC$_{50}$ so to RE1 IC$_{50}$ between 0.8 and 1.5; C represents a ratio of test compound IC$_{50}$ to RE01 IC$_{50}$ between 1.5-10; and C represents a ratio of test compound IC$_{50}$ to RE01 IC$_{50}$ of greater than >10.

TABLE 3

| Test Compound | Relative IC$_{50}$ Ratio |
| --- | --- |
| RE04 | B |
| RE06 | C |
| RE07 | D |
| RE08 | B |
| RE09 | B |
| RE10 | B |
| RE11 | C |
| RE12 | B |
| RE13 | A |
| RE14 | B |
| RE15 | B |
| RE16 | C |
| RE17 | B |
| RE18 | A |
| RE19 | B |
| RE20 | C |
| RE21 | C |
| RE22 | C |
| RE23 | B |
| RE24 | C |
| RE25 | C |
| RE26 | C |
| RE27 | C |
| RE28 | A |
| RE29 | A |
| RE30 | C |
| RE31 | C |
| RE32 | D |
| RE33 | C |
| RE34 | A |
| RE35 | A |
| RE36 | C |
| RE37 | C |
| RE38 | B |
| RE39 | B |

Example 17: Isothermal Titration Calorimetry

Isothermal titration calorimetry measurements were carried out using a MicroCal VP-ITC instrument at 25° C., with the chimeric REV1 CTD protein (300 µM) in the syringe and compound (15 µM) in the cell. Compounds were initially dissolved in 50% MPD. Protein and compound samples were diluted in a buffer containing 50 mM HEPES pH 7.5, 50 mM KCl, 2 mM TCEP, 2% DMSO and 0.1% MPD. Microcal Origin 7 software was used to analyze the data.

Figure 7A:
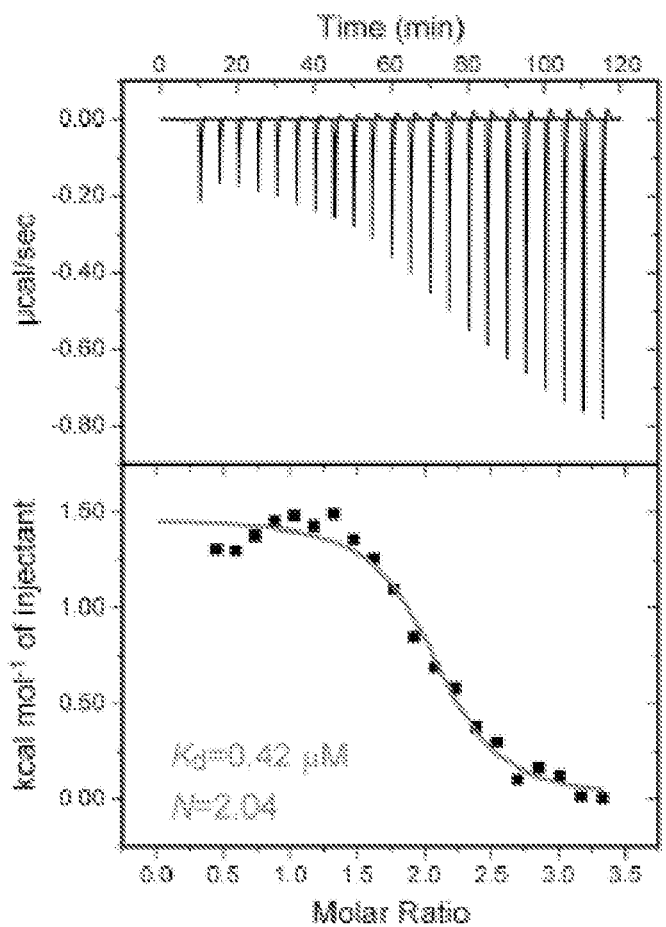
FIG. 7A is a graph showing the results of isothermal titration calorimetry measurements of the REV1 CTD/RE01 interaction with RE01.
Figure 7B:
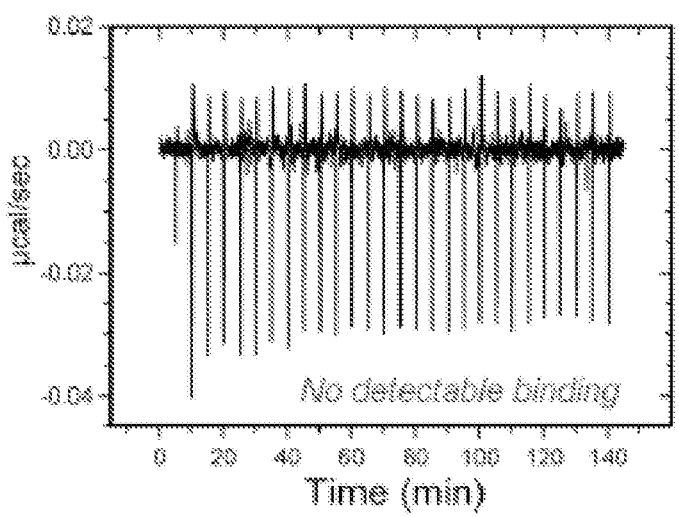
FIG. 7B is a graph showing the results of isothermal titration calorimetry measurements of the REV1 CTD/RE01 interaction with RE07.

Results are shown in FIG. 7A. Isothermal titration calorimetry measurements of the REV1 CTD/RE01 interaction yielded a dissociation constant ($K_d$) of 0.42±0.11 µM and a protein-to-ligand stoichiometry of 2.04±0.03. FIG. 7B shows that substituting the hydrophobic dicholoraniline group in RE01 with a hydrophilic morpholine group in RE07 abolished the REV1 CTD binding as measured by isothermal titration calorimetry.

Example 18

X-ray crystallography: Apo POL $_\kappa$ RIR-REV1 CTD. A sample of 0.6 mM chimeric mouse POL $_\kappa$-REV1 CTD in 25 mM HEPES pH 7.2, 100 mM KCl, 30 mM CHAPS, and 2 mM TCEP was mixed with the mother liquor containing 0.1 M sodium acetate, 25% w/v PEG 4000, 8% w/v isopropanol at a 1:1 drop ratio and crystallized upon incubation at 20° C. Crystals were flash frozen in liquid nitrogen without additional cryoprotectants.

The POL $_\kappa$ RIR-REV1 CTD/RE01 complex. A random micro-seed matrix screen was performed using a sample solution containing 0.6 mM of the chimeric POL $_\kappa$ RIR-REV1 CTD and 4 mM RE01 NaOH salt in a crystallization buffer of 25 mM HEPES pH 7.0, 100 mM KCl, 16.7% MPD and 0.1% β-mercaptoethanol and crystal seeds derived from apo protein crystals, yielding diffracting crystals in a mother liquor containing 20% PEG 3350, and 0.2 M magnesium formate. High-quality crystals were obtained through repeated seeding, and the final crystallization conditions contain 12.5 mM HEPES (pH 7.5), 50 mM KCl, 8.35% MPD, 0.05% p-mercaptoethanol, 10% PEG3350 and 0.1 M magnesium formate. The crystals were harvested and cryoprotected with the mother liquor containing 15% MPD and 1.88 mM RE01 NaOH salt.

X-ray diffraction datasets were collected on the SERCAT 22-ID beamline at Argonne National Laboratory and processed with XDS. The structures of the apo POL $_\kappa$ RIR-REV1 CTD and the POL $_\kappa$ RIR-REV1 CTD/RE01 complex were determined by molecular replacement using the coordinate of the mouse REV1 CTD and POL $_\kappa$ RIR components of our previously determined quaternary complex crystal structure (PDB 4FJO) as the search model. The final coordinates were constructed by iterative cycles of model building with COOT and refinement with PHENIX and were deposited to the Protein Data Bank with accession numbers of 6C59 and 6C8C for the apo protein and the inhibitor-bound complex, respectively.

Figure 6A:
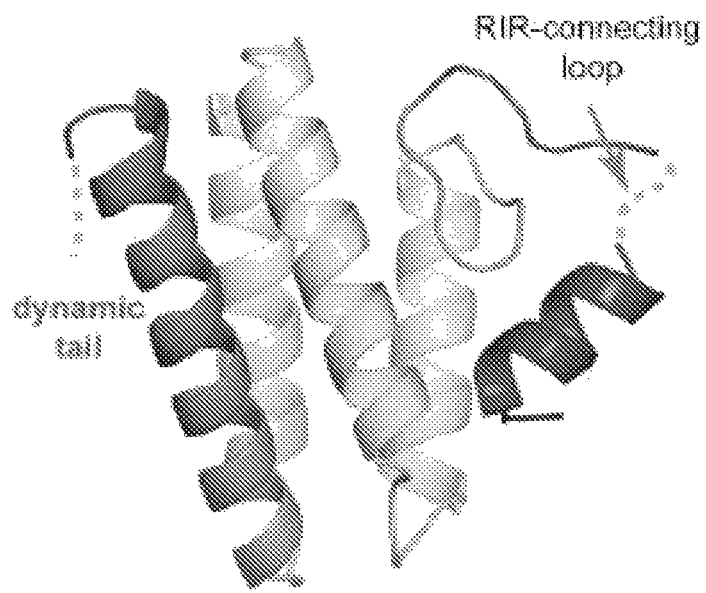
FIG. 6A is an illustration of the the crystal structure of the chimeric POL $_K$ RIR-REV1 CTD (cREV1 CTD) in the apo state.
Figure 6B:
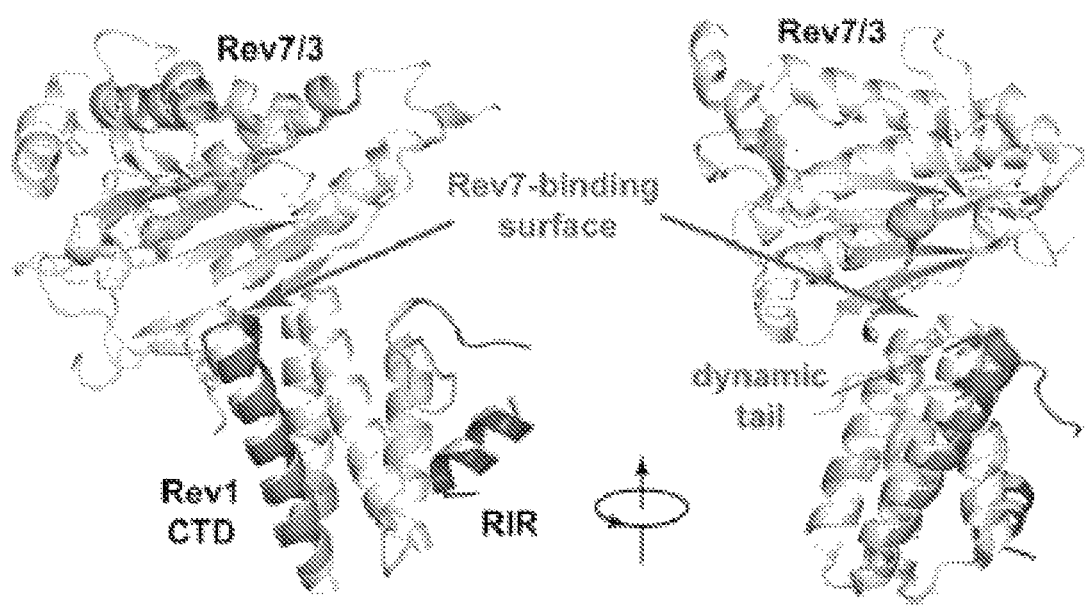
FIG. 6B is an illustration of the superimposition of the apo cREV1 CTD with the corresponding components in the POL $_K$ RIR-REV1 CTD-REV7/3 translesionsome complex (PDB 4FJO).

The crystal structure of the chimeric POL $_\kappa$ RIR-REV1 CTD (cREV1 CTD) in the apo state is shown in FIGS. 6A and 6B. FIG. 6A is a ribbon diagram of the cREV1 CTD, with the N-terminus in blue and C-terminus in red. The POL $_\kappa$ RIR-connecting loop and the C-terminal tail of the REV1 CTD, which are invisible in the electron density, are indicated by dashed grey lines. FIG. 6B illustrates a superimposition of the apo cREV1 CTD with the corresponding components in the POL $_\kappa$ RIR-REV1 CTD-REV7/3 translesionsome complex (PDB 4FJO) reveals similar conformations of the REV1 CTD and POL $_\kappa$ RIR and verifies that the REV7-binding surface of the REV1 CTD (indicated by blue arrows) is unoccupied. The C-terminal tail, which is dynamic and invisible in the apo protein but structured in the translesionsome complex, is labeled in red.

Example 19: In Vitro DSS-Crosslinking

Samples of the chimeric FLAG-tagged POL $_\kappa$ RIR-REV1 CTD in the presence of 0 µM or 100 µM RE01 were treated with increasing molar ratios of DSS (disuccinimidyl suberate) and analyzed by SDS-PAGE followed by Western blotting with anti-FLAG antibody. Monomer and cross-linked dimer bands are labeled.

More specifically, chimeric FLAG-tagged POL $_\kappa$ RIR-REV1 CTD in a buffer containing 25 mM HEPES (pH 7.0), 100 mM KCl, and 4 mM TCEP was mixed with either MPD (control) or RE01 NaOH salt in MPD to yield a reaction solution containing 1 µM protein, 5% MPD, and either 0 or 100 µM compound. Appropriate dilutions of DSS in DMSO were added to the reaction mixture to yield DSS-to-protein molar ratios of 0:1, 0.5:1, 1:1, 5:1, 10:1, and 50:1 and a final DMSO concentration of 5% (v/v). The reaction mixture was incubated for 30 min at room temperature and then quenched by addition of 1 M Tris (pH 8.5). The SDS-loading dye containing 4 mM TCEP and 10.8 mM iodoacetamide (to block free cysteines) was added to each reaction mixture, and the samples were loaded onto a Pre-cast 4-20% gradient SDS-PAGE gel (Bio-Rad). The gel samples were transferred to a 0.45 µm nitrocellulose membrane (Bio-Rad) for Western blotting with the anti-FLAG primary antibody M2 (Sigma-Aldrich) and the HRP-conjugated secondary antibody (LI-COR) and imaging with the LI-COR Odyssey system.

Example 20: Clonogenic survival assay 300 cells were plated in triplicate in 6-well plates for 24 hours. Cisplatin (cis-diammineplatinum(II) dichloride, Sigma-Aldrich) was added to relevant wells for 24 hours. All plates were incubated at 37° C. for 24 hours. Media were changed the next day and in fresh media RE01 (at 1.5 µM concentration) was added to untreated or cisplatin-treated cells for another 24 hours. Media were changed at the end of these combination treatments, and cells were allowed to recover for 7 days. To stain the resulting colonies, media were aspirated and the fixative (50% methanol and 10% glacial acetic acid) was added for 10 minutes, followed by the addition of 0.02% Coomassie brilliant blue R-250 stain (ThermoFisher) in methanol: acetic acid: water in a ratio of 46.5:7:46.5 (v/v/v). Colonies that stained blue and contained at least 40 cells were counted. Relative cell survival or colony formation was calculated by dividing colony counts from treated samples by the DMSO or untreated controls.

Example 21: Viability Assay

Relative viability of cells in response to RE01 and DNA-damaging agents was assessed by the CellTiter-Glo Luminescence cell viability assay (Promega) that determines the number of viable cells based on the relative amount of ATP in the culture, which is directly proportional to the number of metabolically active cells. Briefly, 10,000 cells were plated in each well of a 96-well, white, clear flat bottom plate (Corning). Increasing doses of drugs in various combinations-RE01 alone or in combination with DNA-damaging agents-were added into the plates after 24 hours. The RE01 compound was dissolved in 0.1% DMSO and other drugs were dissolved in solvents ascribed by the manufacturer. In all cases, DMSO controls were run in parallel to the drug treatments. Cells were treated with DMSO or cisplatin (0.5 uM) for 24 hours, followed by RE01 (1.5 uM) treatment for additional 24 hours. Cells were washed and allowed to form colonies for 5-7 days and counted after staining with Coomassie brilliant blue R-250 stain. The relative viability of cells was monitored after 24 hours of drug treatment by adding CellTiter-Glo Luminescence stain to an equilibrated plate per the manufacturer's instructions. Luminescence was measured on the plate reader (Tecan Spark 10M). Relative luminescence, which is indicative of relative survival of metabolically active cells, was calculated by dividing the luminescence of treated samples with DMSO controls.

Figure 3A:
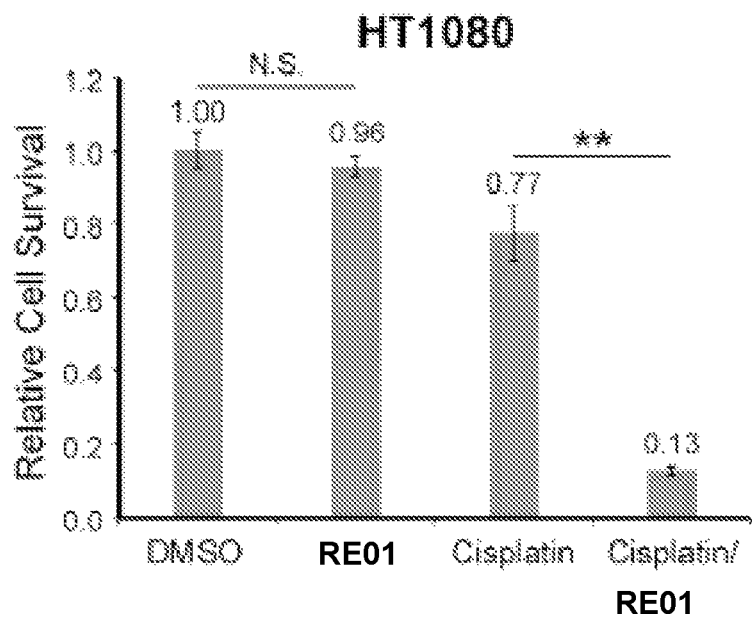
FIG. 3A is a graph showing the relative colony forming ability of HT1080 (human fibrosarcoma) cells in response to DMSO, RE01, cisplatin, and a combination dose of cisplatin and RE01.
Figure 3B:
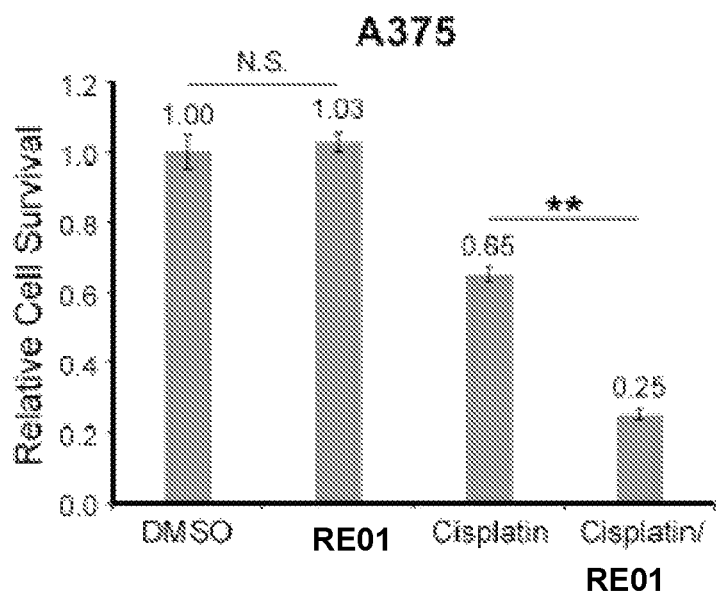
FIG. 3B is a graph showing the relative colony forming ability of A375 (human melanoma) cells in response to DMSO, RE01, cisplatin, and a combination dose of cisplatin and RE01.
Figure 3C:
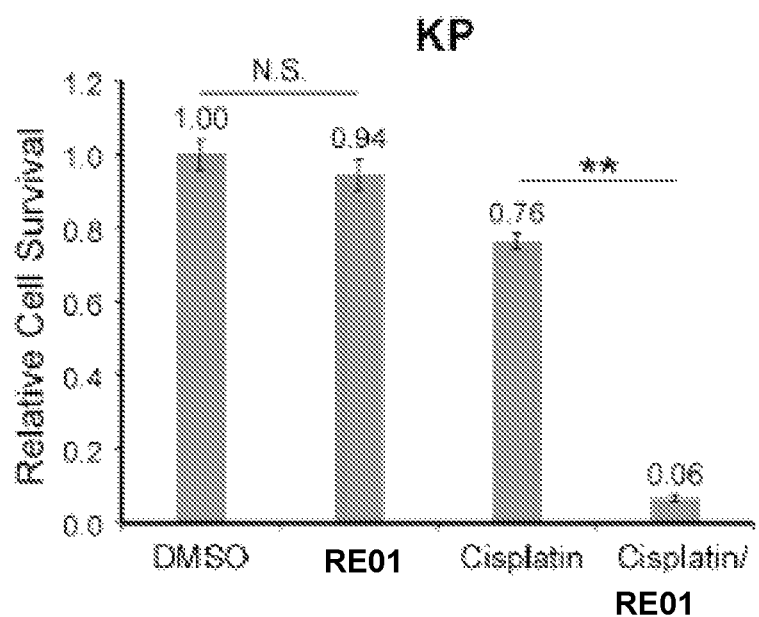
FIG. 3C is a graph showing the relative colony forming ability of KP (mouse Kras$^{G12D}$;p53$^{-/-}$ lung adenocarcinoma) cells in response to DMSO, RE01, cisplatin, and a combination dose of cisplatin and RE01.
Figure 3D:
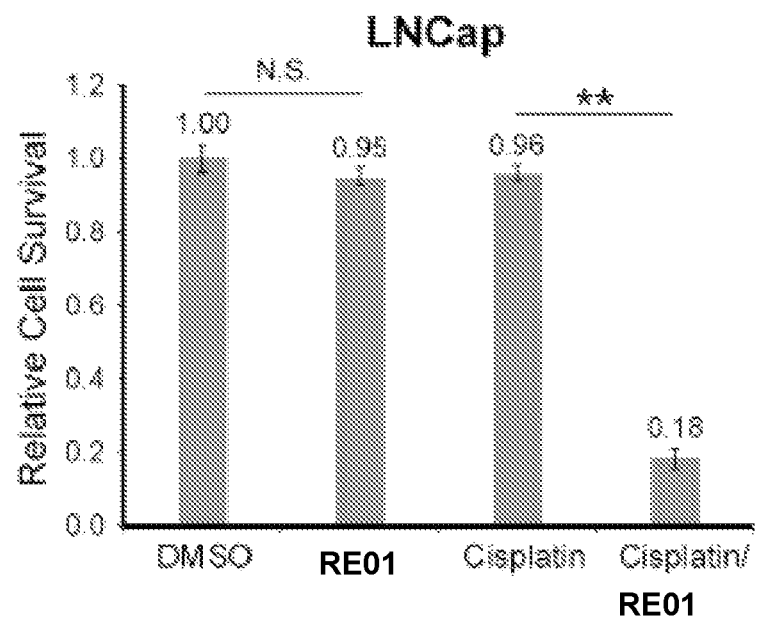
FIG. 3D is a graph showing the relative colony forming ability of LNCap (human prostate adenocarcinoma cells in response to DMSO, RE01, cisplatin, and a combination dose of cisplatin and RE01.
Figure 3E:
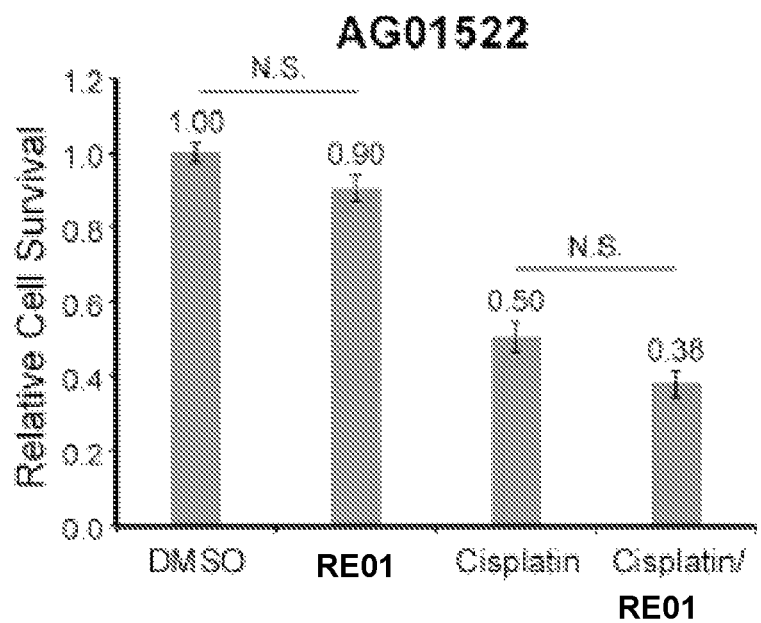
FIG. 3E is a graph showing the relative colony forming ability of AG01522 (human primary fibroblasts) cells in response to DMSO, RE01, cisplatin, and a combination dose of cisplatin and RE01.
Figure 3F:
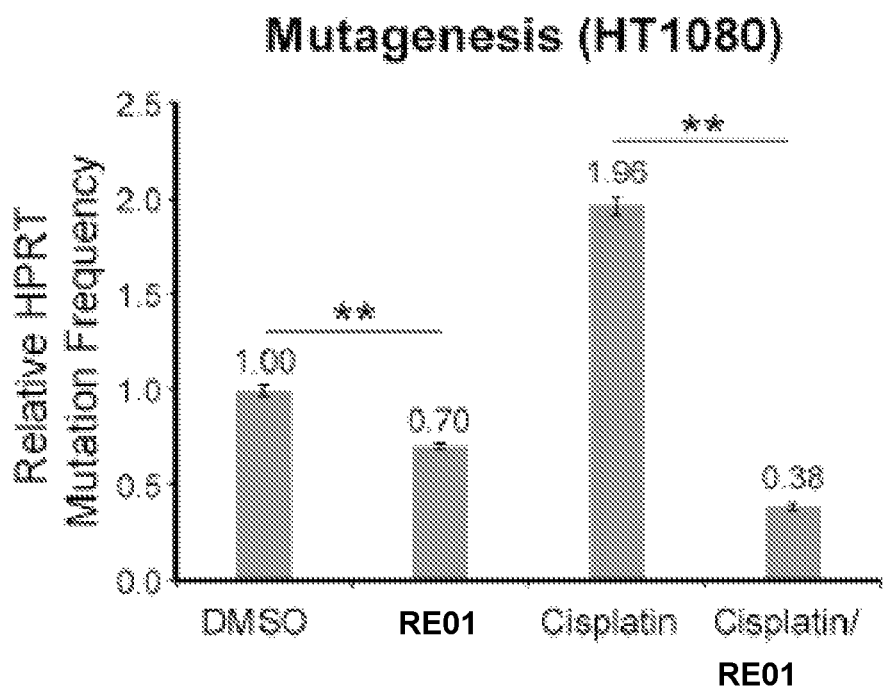
FIG. 3F is a graph showing the relative ability of HPRT$^+$ HT1080 cells to mutate and form HPRT colonies in 6-TG media in the presence of DMSO, 1.5 μM RE01, 0.5 μM cisplatin, and the combination dose of 0.5 μM cisplatin and 1.5 μM RE01.

Shown in FIGS. 3A-3E are the relative colony forming ability of (FIG. 3A) HT1080 (human fibrosarcoma), (FIG. 3B) A375 (human melanoma), (FIG. 3C) KP (mouse $Kras^{G12D};p53^{-/-}$ lung adenocarcinoma), (FIG. 3D) LNCap (human prostate adenocarcinoma), and (FIG. 3E) AG01522 (human primary fibroblasts) cells in response to DMSO, RE01, cisplatin, and a combination dose of cisplatin and RE01. FIG. 3F shows the relative ability of HPRT$^+$ HT1080 cells to mutate and form HPRT colonies in 6-TG media in the presence of DMSO, 1.5 µM RE01, 0.5 µM cisplatin, and the combination dose of 0.5 µM cisplatin and 1.5 µM RE01. Error bars represent standard error of the mean (n=6 for panels A-E and n=12 for panel F). Statistical analysis: one-way ANOVA with Tukey HSD post-hoc test. **P<0.01, N.S., not significant.

Figure 7C:
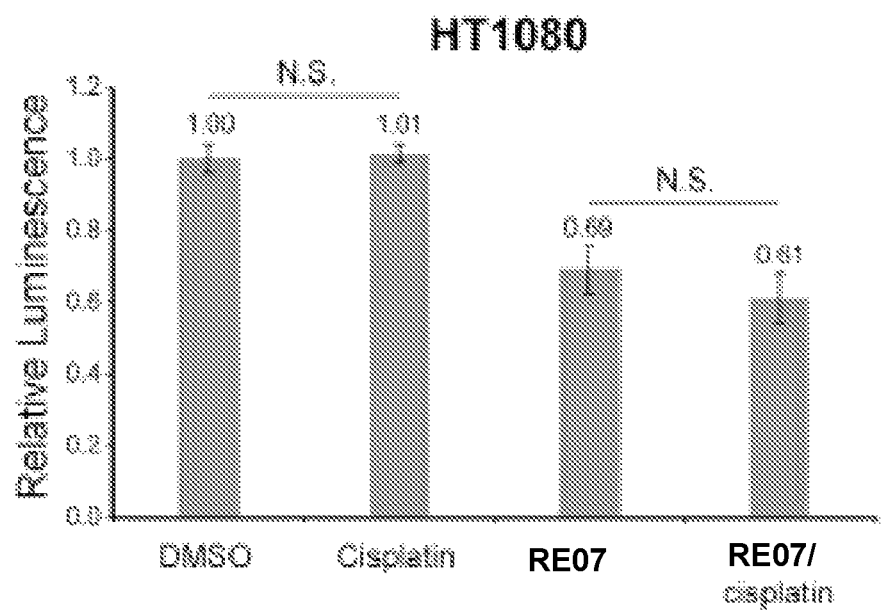
FIG. 7C is a graph of relative cell viabilities of HT1080 cells treated with DMSO, cisplatin (1 μM), RE07 (1.5 μM), or the combination of cisplatin (1 μM) and RE07 (1.5 μM) are shown in panels (D) and (E) respectively.
Figure 7D:
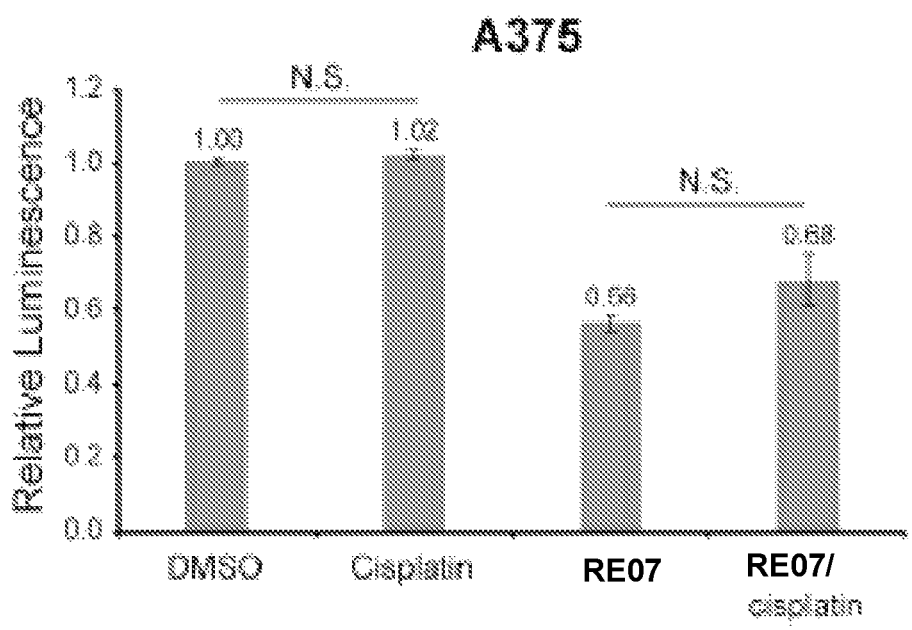
FIG. 7D is a graph of relative cell viabilities of A375 cells treated with DMSO, cisplatin (1 μM), RE07 (1.5 μM), or the combination of cisplatin (1 μM) and RE07 (1.5 μM).
Figure 8A:
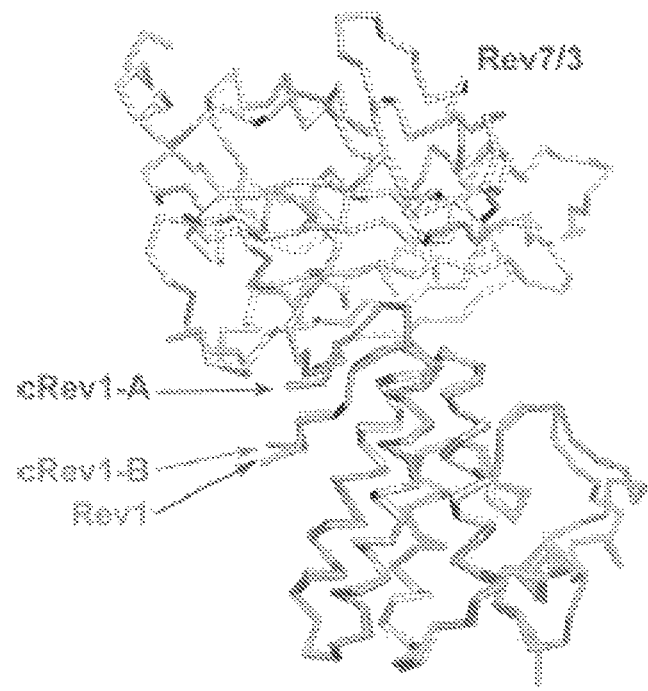
FIG. 8A is an illustration of a superimposition of the subunits of the cREV1 CTD to the corresponding fragments in the POL $_\kappa$ RIR-REV1 CTD-REV7/3 translesionsome complex (PDB 4FJO). Protomers A and B are colored in green and cyan respectively; and the translesionsome complex is colored in grey, except for the REV1 CTD, which is colored in pale cyan.
Figure 8B:
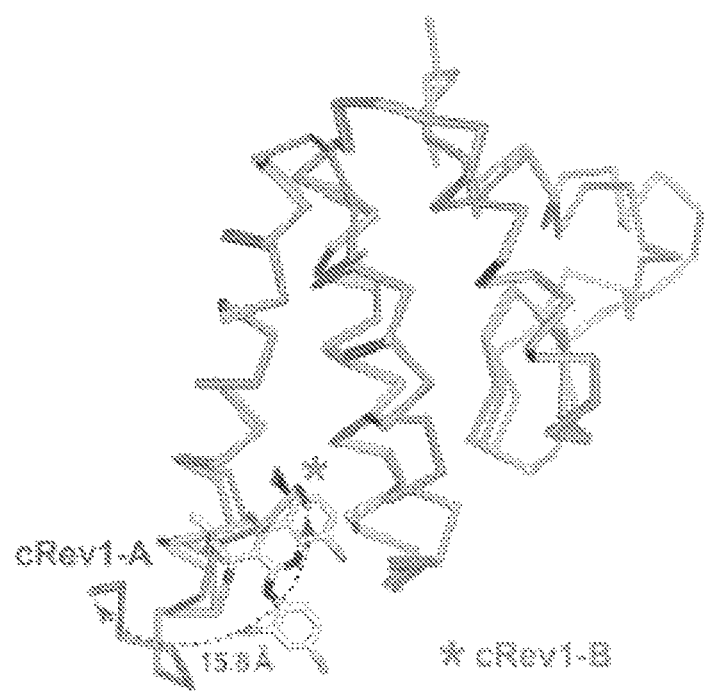
FIG. 8B is an illustration of a superimposition of the two protomers in the cREV1 CTD/RE01 complex, with protomer A colored in green and protomer B colored in cyan. The distance of the C-terminal residue movement is labeled. Proteins are shown in Ca traces whereas RE01 is shown in the stick model.

Relative cell viabilities of HT1080 and A375 cells treated with DMSO, cisplatin (1 µM), RE07 (1.5 µM), or the combination of cisplatin (1 µM) and RE07 (1.5 µM) are shown in FIGS. 7C and 7D respectively. Cell viability was assessed by the Promega CellTiter-Glo Luminescence cell viability assay and normalized to DMSO control samples. Error bars represent standard error of the mean (n=6 for all measurements). Statistical analysis: one-way ANOVA with Tukey HSD post-hoc test. N.S., not significant.

Figure 9B:
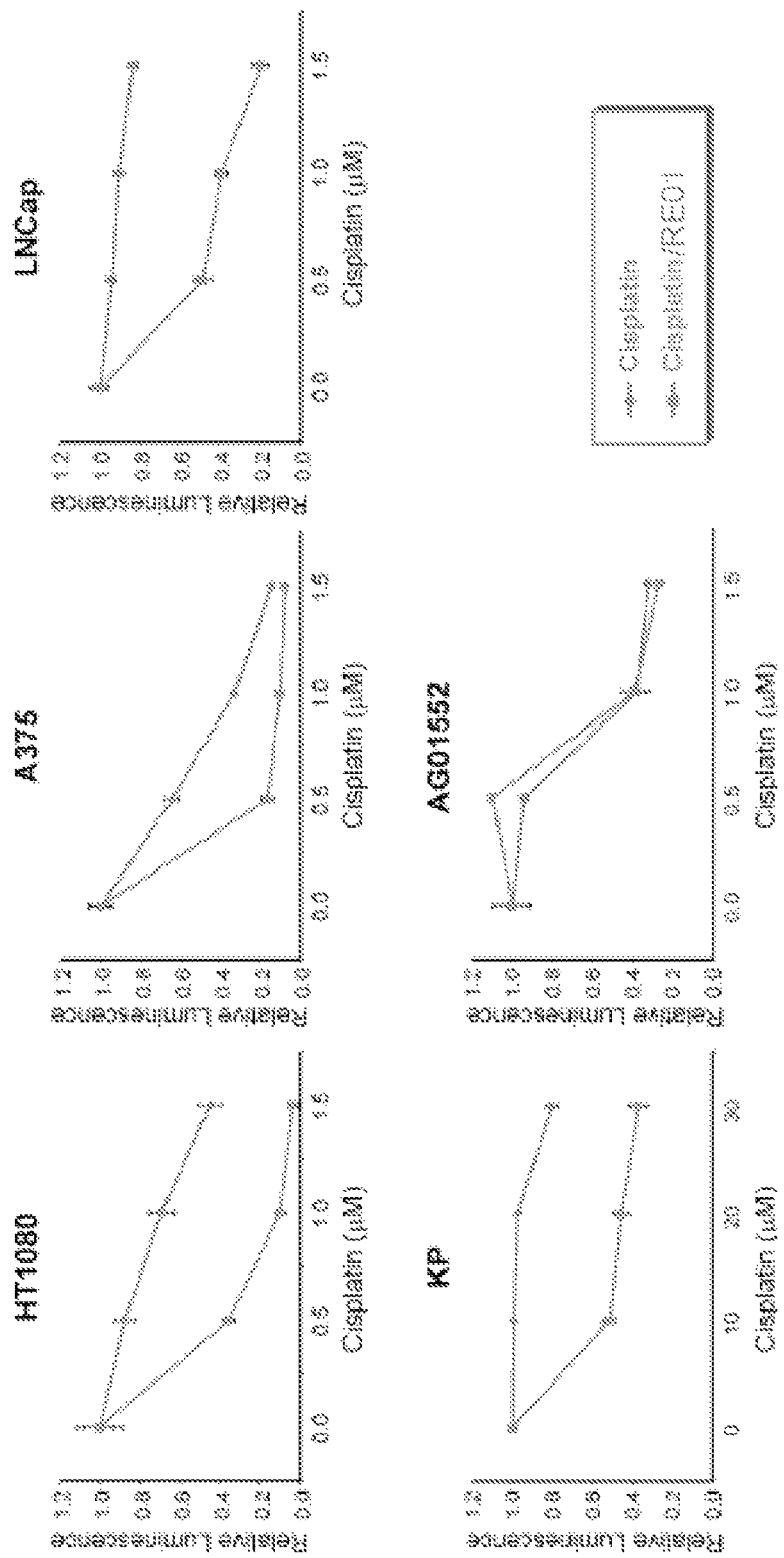
FIG. 9B is a graph showing relative survivability with increasing doses of cisplatin in RE01 treated cells.
Figure 9C:
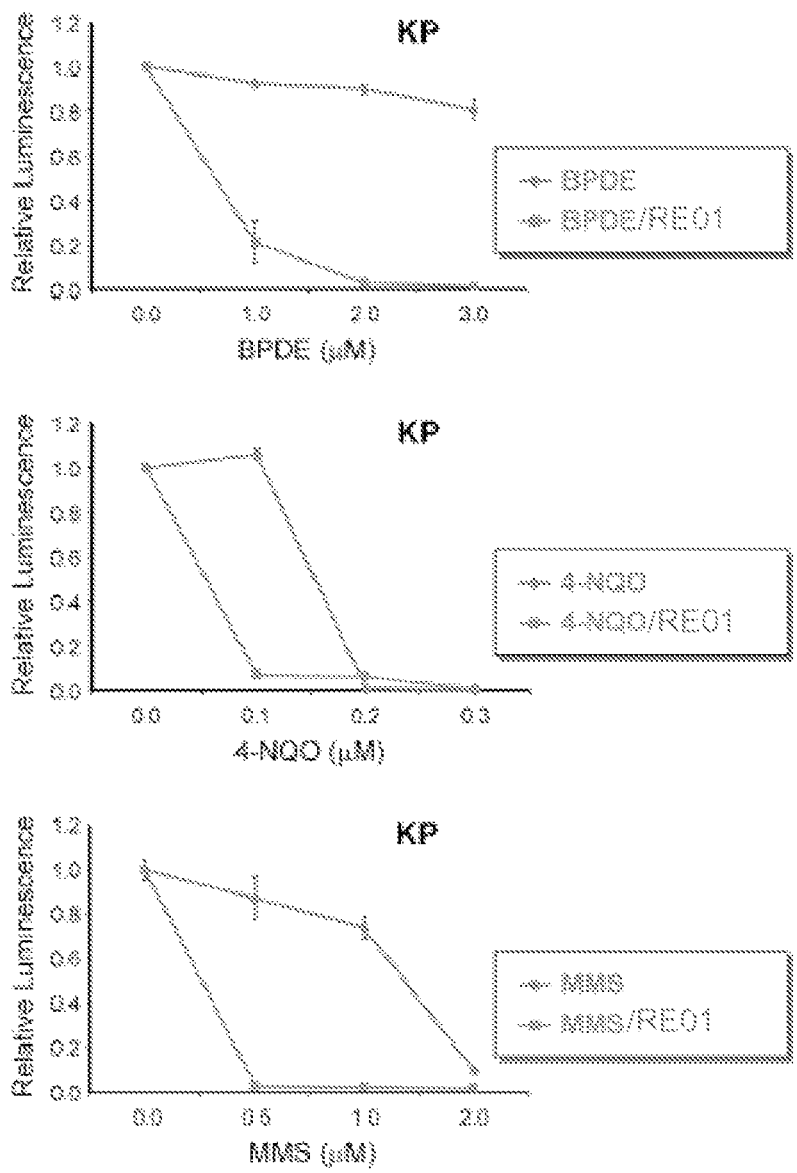
FIG. 9C is a graph showing that RE01 sensitizes cells to DNA-damaging agents beyond cisplatin.
Figure 9D:
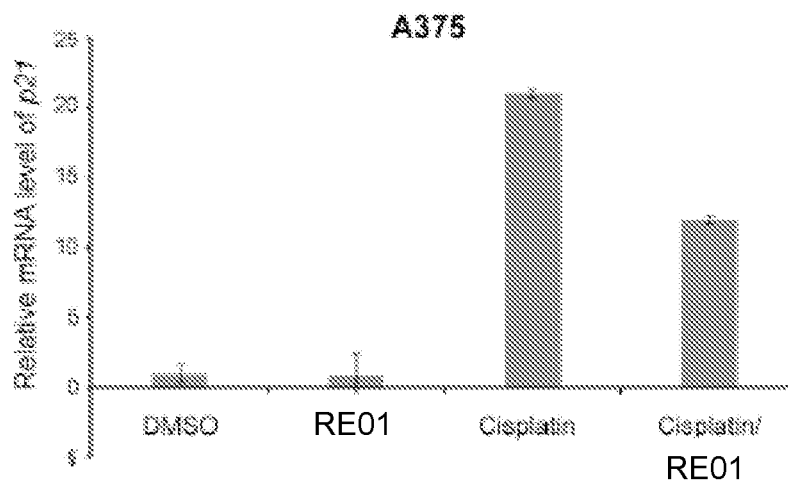
FIG. 9D is a graph showing qRT-PCR measurements of p21 mRNA induction in A375 cells treated with DMSO, RE01, cisplatin and the cisplatin/RE01 combination.
Figure 10A:
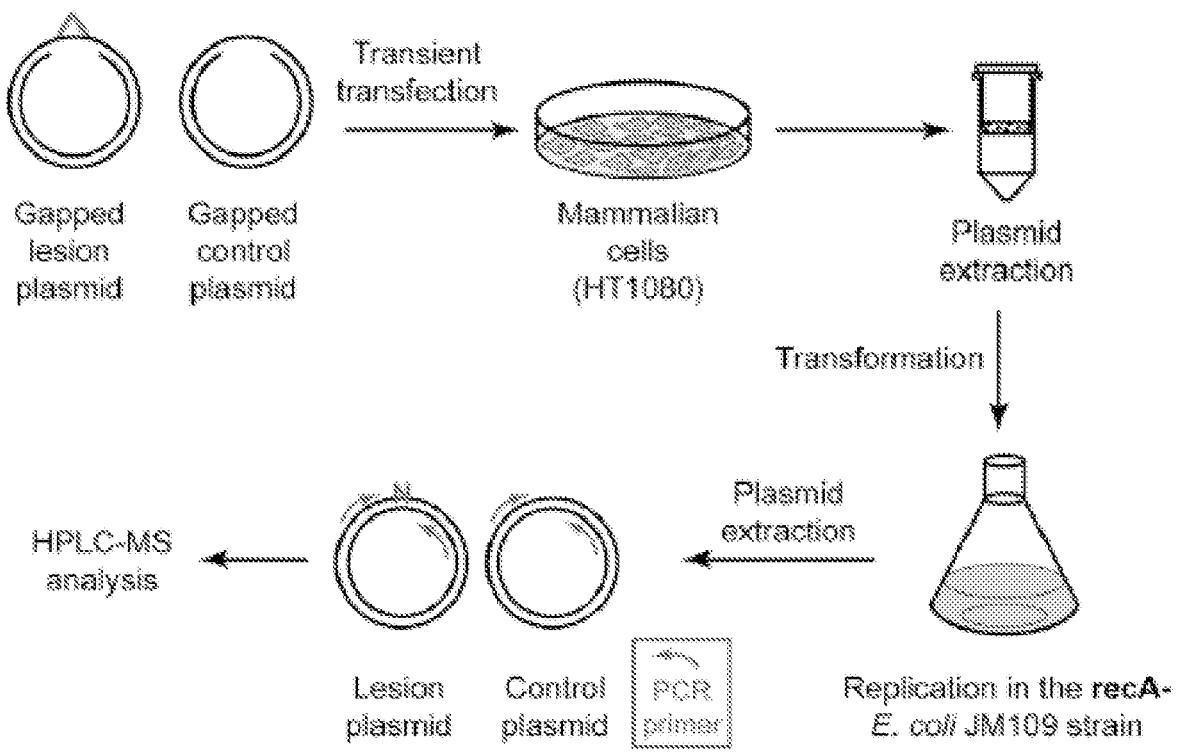
FIG. 10A is an illustration of the experimental design for the gapped plasmid TLS assay.
Figures 10B, 10C:
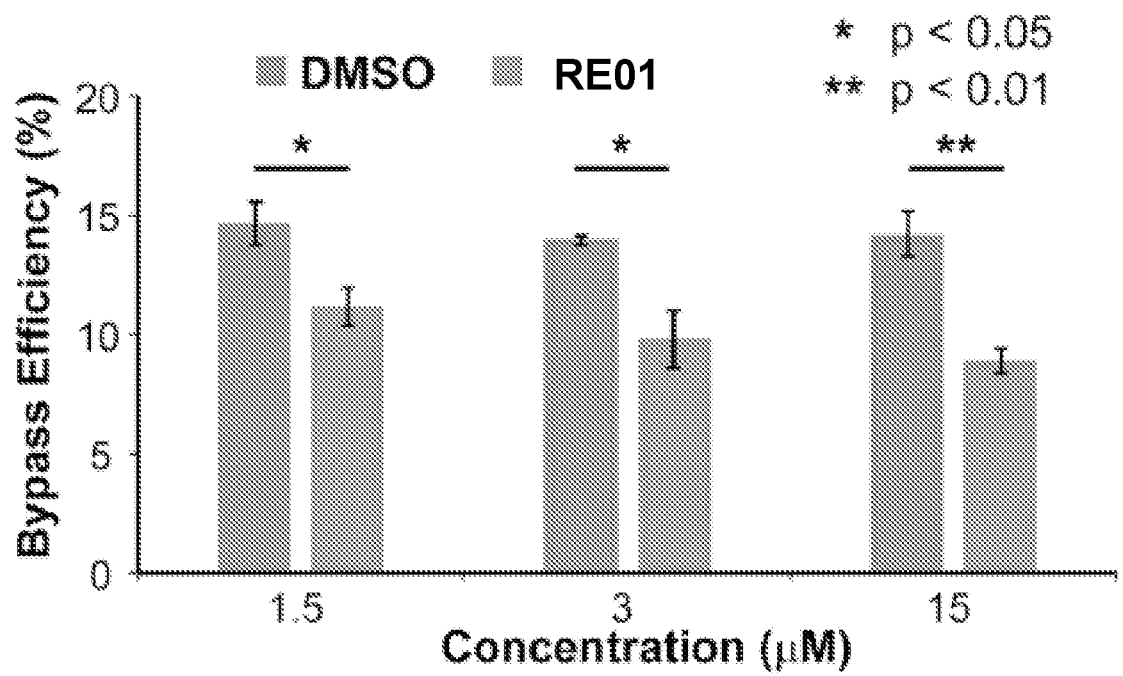
FIG. 10B is a graph showing that RE01 suppresses the bypass efficiency of 1,2-GG cisplatin DNA adduct in HT1080 cell
FIG. 10C is a table showing dose-dependent inhibition of bypass efficiency with different concentrations of RE01. Error bars represent standard error of the mean (n=3 for all measurements). Statistical analysis: Student's t-test. *$P<0.05$; **$P<0.01$.

Consistent with RE01 acting by inhibiting TLS, we found that RE01 sensitized KP cells to other DNA-damaging agents besides cisplatin, including the bulky DNA-damaging agent benzo[a]pyrene diol epoxide (BPDE), the UV-mimetic 4-nitroquinolone 1-oxide (4-NQO), and the alkylating agent methyl methanesulfonate (MMS) (FIG. 9C). Even more importantly, our observations indicated that RE01 acts by inhibiting mutagenic TLS because it also decreased the frequency of both spontaneous and cisplatin-induced HPRT mutations in HT1080 cells (FIG. 3F). In this assay, mutations that inactivate the HPRT gene prevent cells from incorporating the toxic guanine analog, 6-thioguanine (6-TG), into DNA and allow cells to survive in the 6-TG selection medium.

Viabilities of HT1080 (human fibrosarcoma), A375 (human melanoma), LNCap (human prostate adenocarcinoma), KP (mouse $Kras^{G12D};p53^{-/-}$ lung adenocarcinoma), and AG01522 (human primary fibroblasts) cells were assessed by the Promega CellTiter-Glo Luminescence cell viability assay. Relative luminescence intensities to samples treated with 0 µM RE01 (panel A) or with 0 µM DNA-damaging agents (panels B and C) are plotted. Blue lines represent single agent treatments, and orange lines represent RE01 combination treatments. RE01 at a concentration of 1.5 µM was used in all experiments except for the RE01 dose response tests in panel A. Combination treatments in panel A contained cisplatin at concentrations of 0.5 µM for HT1080, A375, LNCap, and AG01522 cells, and 10 µM for KP cells. Error bars represent standard error of the mean (n=6 for panels A-C and n=3 for panel D).

Example 22: HPRT Mutagenesis Assay

For the hypoxanthine-guanine phosphoribosyl transferase (HPRT) mutagenesis assay, cells were first grown in HAT (complete media with 100 µM Hypoxanthine, 0.4 µM Aminopterin and 16 µM Thymidine) media (ThermoFisher) for 14 days to weed out any spontaneous HPRT mutants. After HAT selection, cells were exposed to cisplatin at the 0.5 µM concentration for 24 hours. Then, in fresh media, RE01 at a concentration of 1.5 µM was added to cells. After 24 hours of drug treatment, cells were trypsinized and washed with PBS. While 200-600 cells were plated in complete media in triplicates in 6-well plates to determine clonal efficiency, the rest of the cells were plated in complete media to allow the expression of the phenotype for 8 days. Then, 500,000 cells per treatment were plated in sextuplicate in 10 cm dishes in 6-TG media to allow the proliferation of mutated HPRT$^-$ cells. Colonies were fixed (50% methanol and 10% glacial acetic acid), stained (0.02% Coomassie brilliant blue R-250 stain in methanol: acetic acid: water in a ratio of 46.5:7:46.5 (v/v/v)), and counted after 14-20 days. The HPRT mutation frequency was calculated as the ratio of the number of HPRT$^-$ colonies in 6-TG media to the number of surviving colonies plated in complete media to determine clonal efficiency.

Figure 4A:
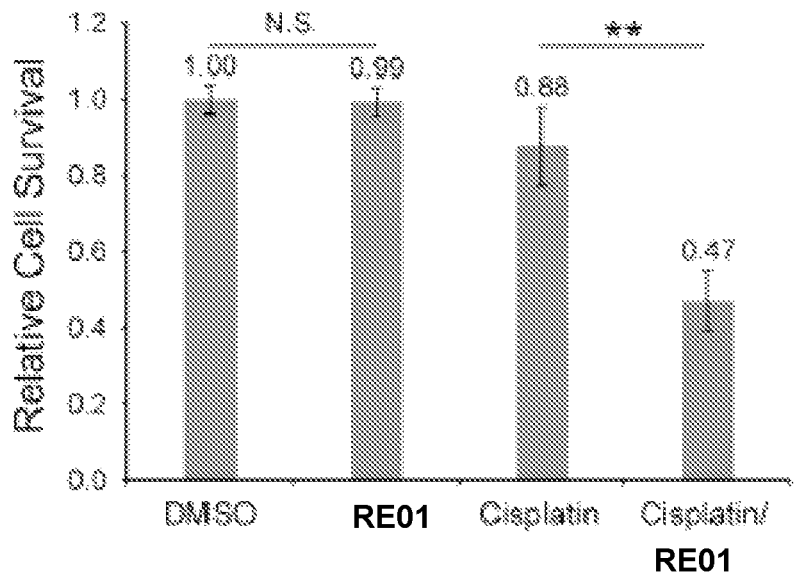
FIG. 4A is a graph showing the results of combination treatment of RE01 (1.5 μM) and cisplatin (0.5 μM) in comparison with cisplatin treatment alone on the colony forming ability in Rev1$^{+/+}$ MEF cells.
Figure 4B:
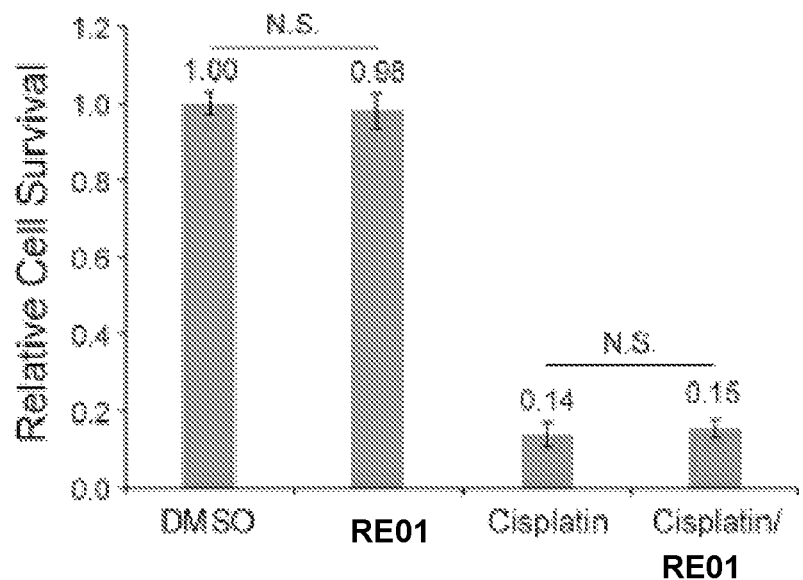
FIG. 4B is a graph showing the results of combination treatment of RE01 (1.5 μM) and cisplatin (0.5 μM) in comparison with cisplatin treatment alone on the colony forming ability in Rev1$^{-/-}$ MEF cells.
Figure 4C:
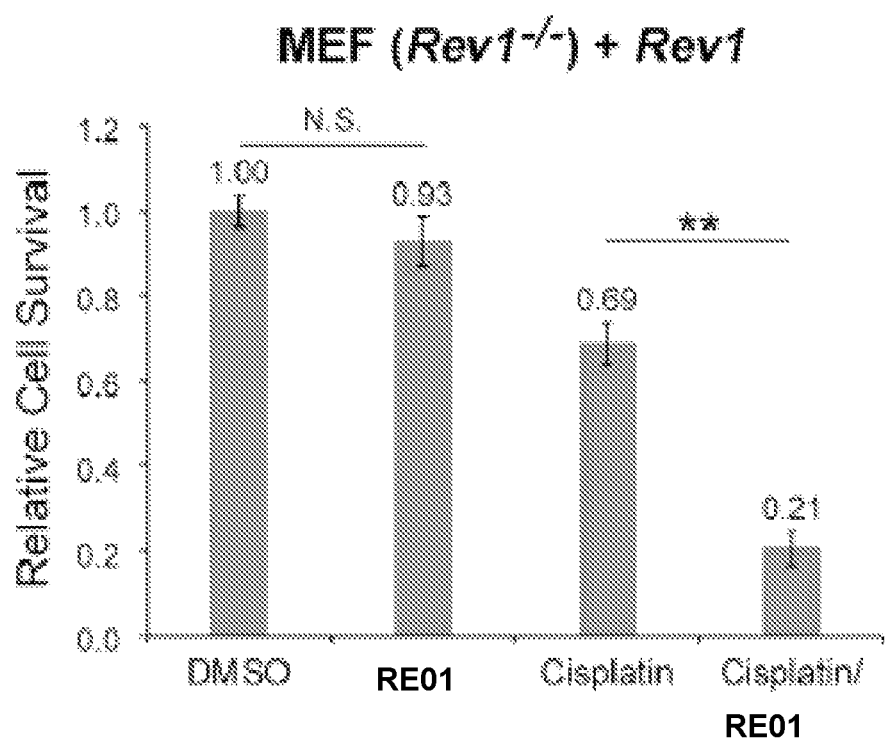
FIG. 4C is a graph showing complementation of Rev1$^{-/-}$ MEF cells with a plasmid encoding REV1 by nucleofection fully restored the RE01 (1.5 μM) mediated sensitization to cisplatin (1 μM).
Figure 4D:
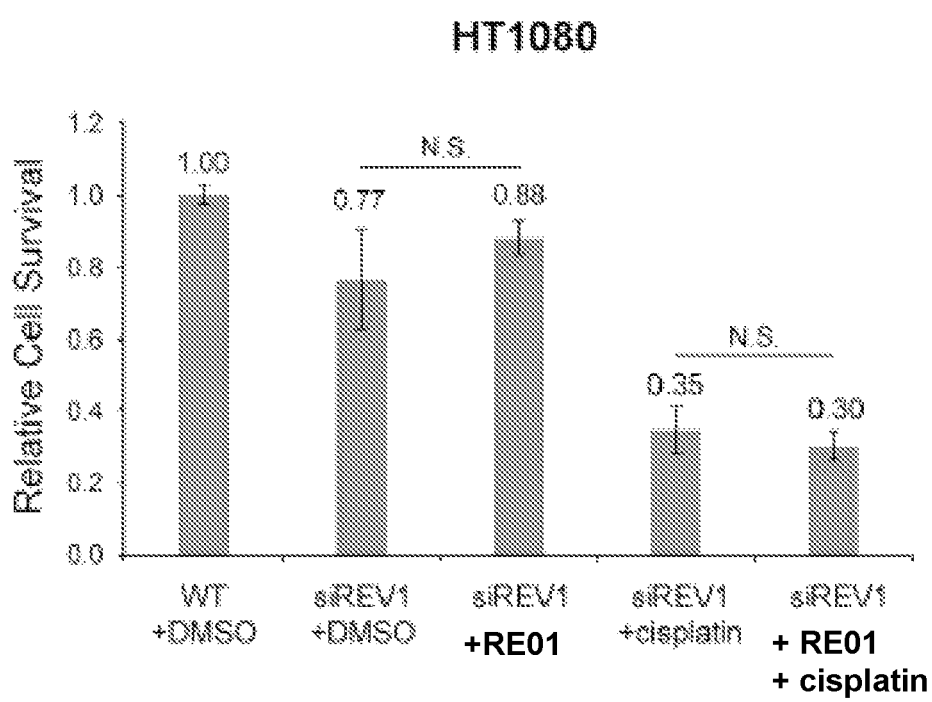
FIG. 4D is a graph showing siRNA knock-down of REV1 abolished RE01 (1.5 μM) mediated sensitization to cisplatin treatment (1 μM) in HT1080 cells.
Figure 4E:
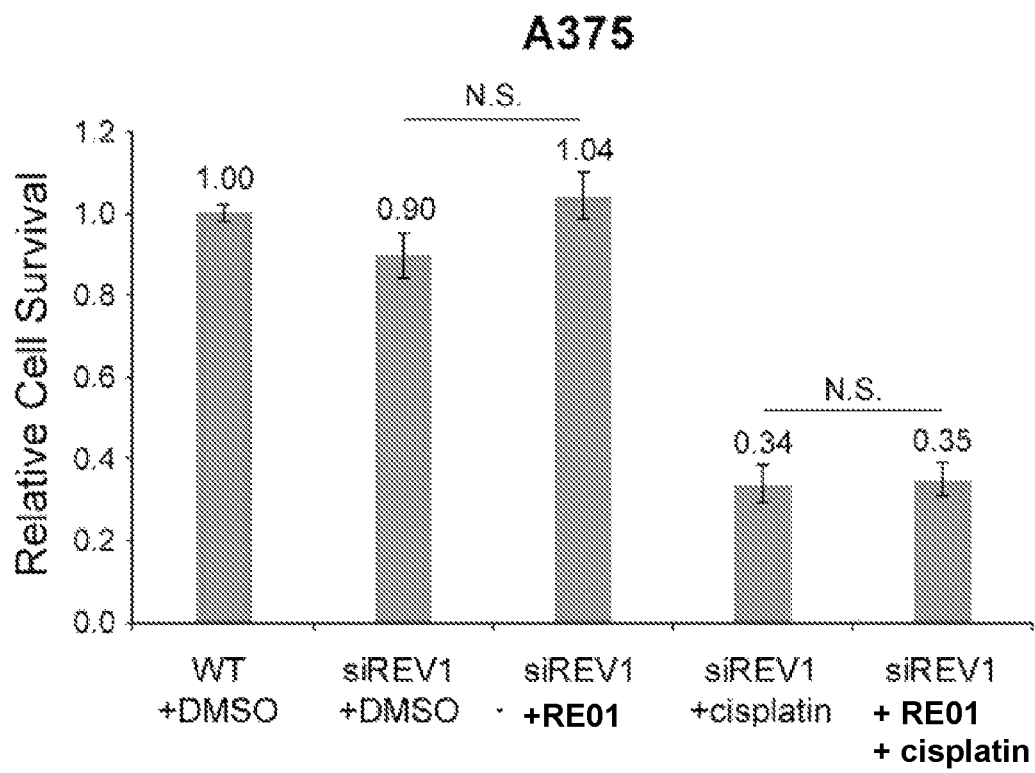
FIG. 4E is a graph showing siRNA knock-down of REV1 abolished RE01 (1.5 μM) mediated sensitization to cisplatin treatment (1 μM) in A375 cells.
Figure 4F:
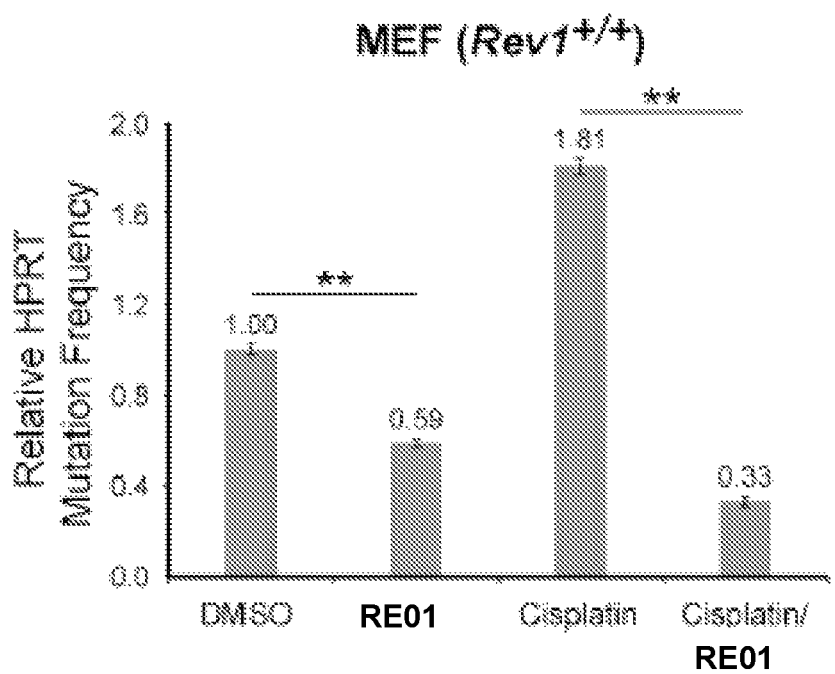
FIG. 4F is a graph showing the results of treatment of Rev1$^{+/+}$ MEF cells with RE01 (1.5 μM) compared to DMSO controls.
Figure 4G:
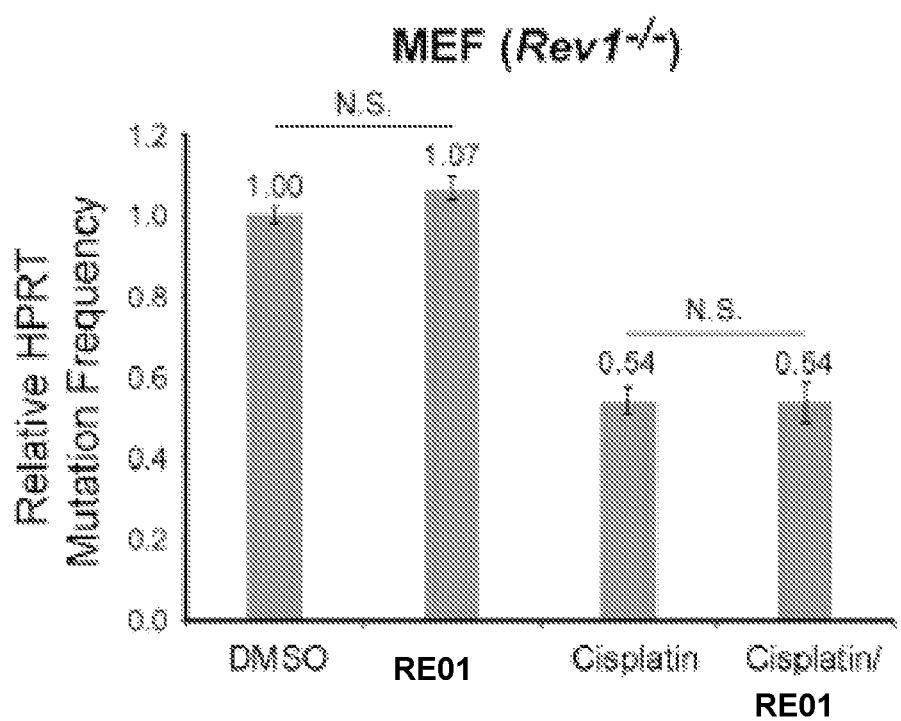
FIG. 4G is a graph showing the results of treatment of Rev1$^{-/-}$ MEF cells with RE01 (1.5 μM) compared to DMSO controls.

The combination treatment of RE01 (1.5 µM) and cisplatin (0.5 µM) significantly reduced the colony forming ability in Rev1$^{+/+}$ MEF cells (Figure A), but not in Rev1$^{-/-}$ MEF cells (FIG. 4B), in comparison with cisplatin treatment alone. FIG. 4C shows that complementation of Rev1$^{-/-}$ MEF cells with a plasmid encoding REV1 by nucleofection fully restored the RE01 (1.5 µM) mediated sensitization to cisplatin (1 µM). FIG. 4D and FIG. 4E respectively show that siRNA knock-down of REV1 abolished RE01 (1.5 µM) mediated sensitization to cisplatin treatment (1 µM) in HT1080 cells and in A375 cells. As shown in FIG. 4F treatment with RE01 (1.5 µM) significantly reduced spontaneous or cisplatin-induced (0.5 µM) HPRT mutation rates in Rev1$^{+/+}$ MEF cells, but not, as shown in FIG. 4G, in Rev1-/- MEF cells. Relative cell survival reflects the normalized colony forming ability of treated cells to DMSO controls. Error bars represent standard error of the mean (n=12 for panels FIGS. 4A-4C and FIGS. 4F-4G; n=6 for FIGS. 4D-4E). Statistical analysis: one-way ANOVA with Tukey HSD post-hoc test. **P<0.01; N.S., not significant.

Example 23: Nucleofection

REV1 was knocked down by transiently transfecting SMARTpool: ON-TARGETplus REV1 siRNA by nucleofection. The siRNA was mixed with the nucleofection buffer Mouse/Rat Hepatocyte Nucleofector™ Kit (Lonza) and electroporated using the Nucleofector™ 2b device. Full-length mouse Rev1 on the pC3 plasmid (Clontech) was nucleofected using the same buffers and device into Rev1$^{-/-}$ cells to complement the REV1 function.

Example 24: Synthesis of the 16Mer Oligonucleotide Containing a Cisplatin 1,2-GG Lesion and Construction of the Gapped Plasmid The 16mer oligonucleotide containing a cisplatin 1,2-GG lesion was synthesized as described below. The platination reaction was carried out with aquated derivatives of the platinum complexes to facilitate their reaction with a 16mer oligonucleotide containing a 1,2-GG sequence (5'-CTCTCTCGGCCTTCTA-3' (SEQ ID NO: 1)). The aquated complexes were obtained by overnight stirring in the dark at room temperature of a solution containing cisplatin and 1.98 equivalent of silver nitrate. The precipitated silver chloride was removed by a 0.2 µm syringe filter. DNA was mixed with aquated platinum complex in a 1:2 ratio at 37° C. for 2 hours. The target 16mer oligonucleotide containing the cisplatin 1,2-GG lesion was purified by reverse-phase HPLC with a C18 column (5 um, 100 Å, 150×4.6 mm, Phenomenex). The molecular weight and lesion location were characterized by LC-MS (AB Sciex).

The double stranded plasmid pUC19 with ampicillin resistance was modified to include the oligonucleotide containing cisplatin 1,2-GG lesion on one strand and a gapped region across it. Briefly, the 16mer cisplatin-containing oligonucleotide was flanked by two 21mer regular DNA strands (5'-GCCCGTCGTAGCGCGCATGCA-3' (SEQ ID NO: 2) on the 5' end and 5'-TCTCGAGTG TTCCGTCAGCAC-3' (SEQ ID NO: 3) on the 3' end) and elongated to a 58mer lesion-containing single strand DNA. After linearizing the plasmid by restriction endonucleases BstAPI and BspQI (New England Biolabs), the 58mer oligonucleotide was mixed with two scaffolds (5'-TG-CATGCGCGCTACGACG-3' (SEQ ID NO: 4) and 5'-AGCGTGCTGACGGAACACTCGAGA-3' (SEQ ID NO: 5)) and ligated with the linear pUC19 plasmid to build up a circular plasmid containing a site-specific cisplatin 1,2-GG lesion and a 16-nucleotide gap on the opposite strand.

Example 25: The Quantitative Assay of the Gapped Plasmid Containing a Cisplatin 1,2-GG Lesion A competitor gapped plasmid that was three bases longer (started from a 19mer oligonucleotide 5'-CTCTCTAGGCT-CACTTCTA-3' (SEQ ID NO: 6)) than the lesion-containing plasmid was used as the internal control. The cells were pre-treated with either DMSO or RE01 (1.5, 3.0 and 15.0 µM) for 24 hours. Gapped-lesion plasmid (200 ng) and competitor plasmid (50 ng) were transfected in a 4:1 ratio into 300,000 HT1080 cells using Lipofectamine 3000 (ThermoFisher). Transfected cells were incubated at 37° C. for 4 hours. Next, the cells were trypsinized (0.25% trypsin-EDTA), and DNA was extracted using the Qiagen DNA isolation kit. The isolated DNA was then transformed into the recA-$E.$ $coli$ strain, JM109, to propagate fully closed plasmids obtained from the mammalian cells. After 16 hours, total plasmid DNA was isolated from the $E.$ $coli$ cells and the region encompassing the cisplatin lesion from both the cisplatin and competitor plasmids was amplified by PCR (forward primer: 5'-TTGTACTGAGAGTGCAC-CATGCCCGT-3' (SEQ ID NO: 7), reverse primer: 5'-GAGTCAGTGAGCGAGGAAGCGTGCTG-3' (SEQ ID NO: 8)). Two restriction endonucleases Xhol and Sphl (New England Biolabs, Ipswich, Mass.) were used to digest the PCR products into short DNA pieces, 20mer for the cisplatin plasmid and 23mer for the competitor plasmid. The digestion products were chromatographed on a PolarAdvantage C18 column (250×2.1 mm, 3 µm, 120 Å, ThermoFisher) eluted at 0.1 mL/min with a methanol gradient (15%-50%, 400 mM hexafluoro-2-propanol), followed by the ESI triple quadrupole time-of-flight mass spectrometry (AB Sciex 4600) to detect the final nucleoside signal in the negative ion mode. The input ratio is the initial 4:1 ratio of the cisplatin 1,2-GG lesion and the competitor plasmid that were used to transfect mammalian cells. The gap-filling efficiency by TLS was calculated by dividing the output ratio obtained from HPLC-MS with the input ratio (4:1) and the results were normalized to 100%.

Example 26: Murine Xenograft Tumor Model

Prior to in vivo experiments, we verified that the DNA damage response pathways were intact in A375 cells by detecting elevated levels of the p21 biomarker via qRT-PCR in response to cisplatin or cisplatin/RE01 treatment (FIG. S4D). Total RNA was isolated by using the RNeasy Mini kit (Qiagen) from cells treated with RE01 (1.5 µM), cisplatin (1 µM) and a combination of both RE01 (1.5 µM) and cisplatin (1 µM). 5 ng of RNA from each sample was mixed with 10 µl of Applied Biosystems™ PowerUp™ SYBR™ Green Master Mix (ThermoFisher), 1 µl of MultiScribe™ Reverse Transcriptase (ThermoFisher), 0.1 µl of RNaseOUT™ Recombinant Ribonuclease Inhibitor and 5.9 µl of RNase-free water, and run in a one-step qRT-PCR reaction. Each reaction was run in triplicate. Primers used were: p21 F 5'-GTCACTGTCTTGTACCCTTGTG-3' (SEQ ID NO: 9), p21 R 5-CGGCGTTTGGAGTGG TAGAAA-3' (SEQ ID NO: 10); GAPDH F 5'-GGAGCGAGATCCCTCCAAAAT-3' (SEQ ID NO: 11), GAPDH R 5'-GGCTGTTGTCAT-ACTTCTCATGG-3' (SEQ ID NO: 12).

NCRNU-F (nude) female, 6-8-week-old mice were divided into 4 groups (with 6 animals per group) for saline, cisplatin alone, RE01 alone, and cisplatin and RE01 combination treatments. Three million A375 cells mixed in matrigel (Corning) were injected into each flank of the 6 mice to generate 10-12 xenograft tumors per treatment group. After the tumors grew to a total tumor volume of at least 100 mm$^3$, the drugs (saline, cisplatin alone, RE01 alone, and cisplatin and RE01 combination) with a total volume of 100 µL per injection were injected directly into the tumor. Treatments were carried out twice per week for 5 weeks. On the dosing day, tumors were first measured with calipers, weights were recorded, and then the drugs would be injected directly into the tumors. The mice were sedated with isofluorane prior to measurements and treatments.

The drugs were formulated in 10% EtOH, 40% PEG400, and 50% saline for all the four types of treatments. Cisplatin was injected at a dose of 1 mg/kg per animal and RE01 was administered at a 1.6 mg/kg per animal. In the combination treatment of cisplatin and RE01, the same doses of 1 mg/kg and 1.6 mg/kg respectively per animal were administered. Tumor volumes were calculated by the formula (W$^2$×L)/2 as described previously.

Figure 5A:
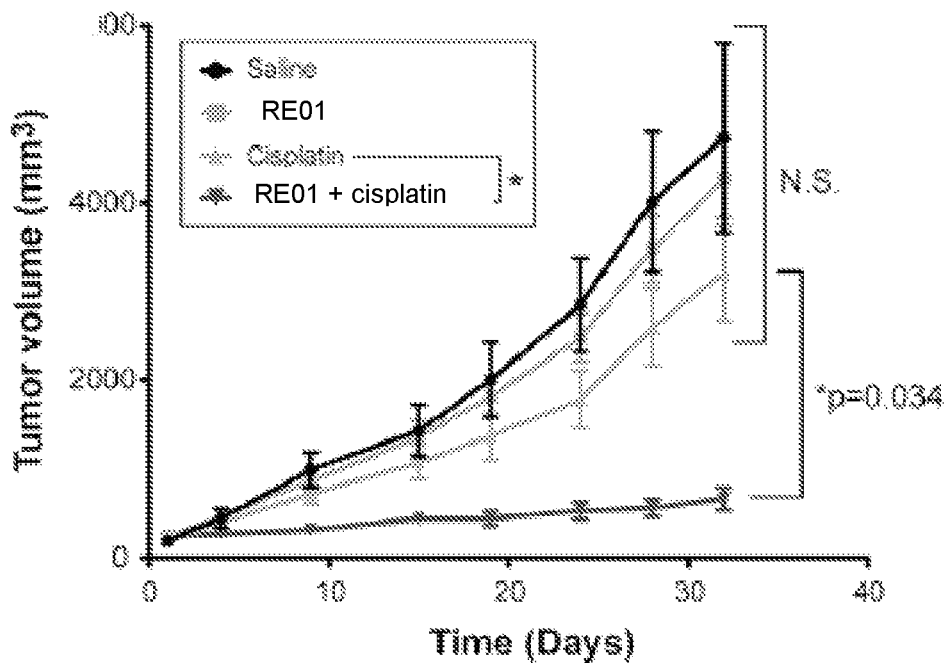
FIG. 5A is a graph showing the effect of RE01 on tumor cell response to cisplatin in a A375 xenograft mouse model (Example 26).

Results are shown in FIG. 5A which shows inhibition of A375 xenograft tumor growth with (i) saline, (ii) RE01, (iii) cisplatin, and (iv) cisplatin and RE01. Error bars represent standard error of the mean (n=10–12 xenograft tumors from 6 mice per treatment group). p-values for tumor volumes between each treatment group were calculated by the Welch's t-test (Graphpad Prism). *p<0.05, N.S., not significant.

Figure 5B:
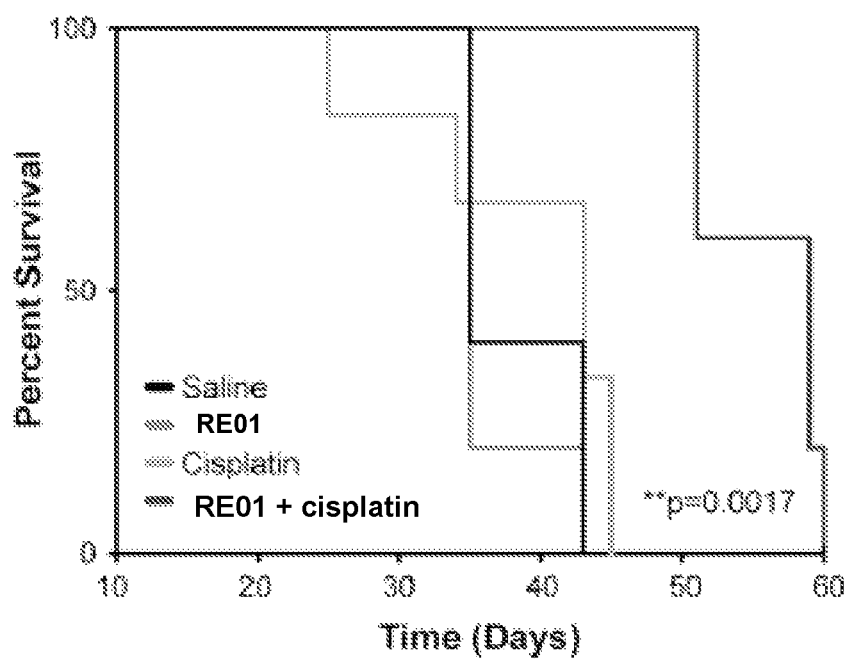
FIG. 5B shows survival curves of tumor-bearing mice treated with the four formulations described in Example 26.

In the survival curve shown in FIG. 5B, Day 10 represents the first day of the specified drug administration (n=6 mice per treatment group in one representative experiment shown in FIG. 5, from a total of three independent experiments). A p-value of 0.0017 for the RE01 and cisplatin combination treatment vs. cisplatin treatment for survival studies was determined by using the Mantel-Cox log-rank test.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A method of treating cancer, comprising administering to a subject in need thereof (i) one or more secondary therapeutic agents and (ii) one or more compounds of formula (I),

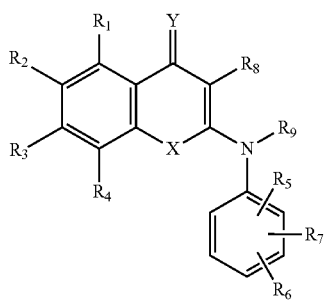

or a pharmaceutically acceptable salt thereof, wherein
X and Y are independently selected from NR, O, or S, where R is hydrogen or $C_1$-$C_4$ alkyl;
$R_1$, $R_2$, $R_3$, and $R_4$ are independently selected from the group consisting of hydrogen, halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl)$_2$, —$CO_2$H, —$CO_2$($C_1$-$C_6$ alkyl), —CHO, —CO($C_1$-$C_6$ alkyl), and —S(O)$_{0-2}$($C_1$-$C_6$ alkyl);
$R_5$, $R_6$, and $R_7$ are independently selected from the group consisting of hydrogen, halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —$CONH_2$, —CONH($C_1$-$C_6$ alkyl), —CON($C_1$-$C_6$ alkyl)$_2$, —$CO_2$H, —$CO_2$($C_1$-$C_6$ alkyl), —CHO, —CO($C_1$-$C_6$ alkyl), and —S(O)$_{0-2}$($C_1$-$C_6$ alkyl),
or $R_5$ and $R_6$, together with the atoms to which they are attached, form a 5 or 6 membered aryl, heteroaryl, or heterocyclyl;
$R^8$ is $C_1$-$C_8$ alkyl optionally substituted with one or more $R_{10}$, $C_2$-$C_8$ alkenyl optionally substituted with one or more $R_{10}$, or $C_2$-$C_8$ alkynyl optionally substituted with one or more $R_{10}$,
wherein each $R_{10}$ is independently selected from the group consisting of halogen, —$NO_2$, —CN, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CONH($C_1$-$C_6$ alkyl), —CON($C_1$-$C_6$ alkyl)$_2$, —$CO_2$H, —$CO_2$($C_1$-$C_6$ alkyl), —CHO, —CO($C_1$-$C_6$ alkyl), and —S(O)$_{0-2}$($C_1$-$C_6$ alkyl), or two $R_{10}$ groups when attached to the same carbon atom form =O, =NR, or =N—OH; and
$R^9$ is hydrogen or $C_1$-$C_4$ alkyl.

2. The method of claim 1, wherein the cancer is selected from the group consisting of breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma, fibrosarcoma, and peripheral neuroepithelioma.

3. The method of claim 1, wherein the secondary therapeutic agent is a chemotherapeutic reagent.

4. The method of claim 3, wherein the chemotherapeutic reagent is an alkylating antineoplastic agent.

5. The method of claim 3, wherein the chemotherapeutic reagent is a platinum-based antineoplastic agent.

6. The method of claim 1, wherein the one or more secondary therapeutic agents is cisplatin.

7. The method of claim 1, wherein the one or more secondary therapeutic agents is administered prior to the one or more compounds of formula (I).

8. The method of claim 1, wherein the one or more secondary therapeutic agents is administered concurrently with the one or more compounds of formula (I).

9. The method of claim 1, wherein the one or more secondary therapeutic agents is administered after the one or more compounds of formula (I).

10. The method of claim 1, wherein X is NR or O.

11. The method of claim 1, wherein Y is NR or O.

12. The method of claim 1, wherein the compound of formula (I) is:

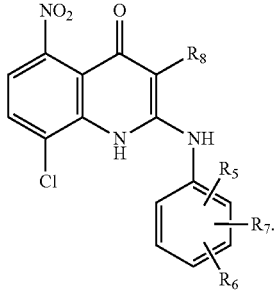

13. The method of claim 1, wherein the compound of formula (I) is:

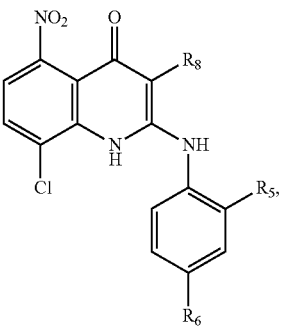

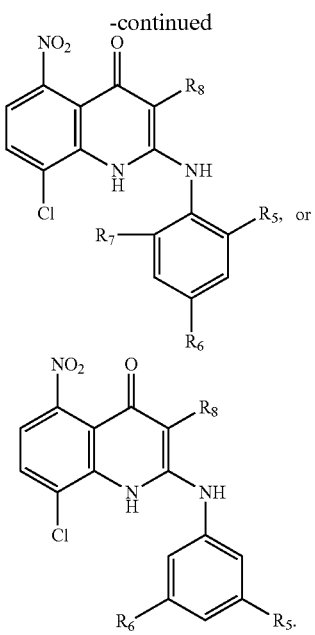

14. The method of claim 13, wherein $R_5$ and $R_6$ are independently hydrogen, halogen, —$NO_2$, —CN, $C_1$-$C_6$ alkyl, $C_1$-$C_6$ haloalkyl, —OH, $C_1$-$C_6$ alkoxy, $C_1$-$C_6$ haloalkoxy, —$CO_2H$, or —$CO_2(C_1$-$C_6$ alkyl).

15. The method of claim 13, wherein $R_5$ and $R_6$ are independently —F, —Cl, —Br, —$NO_2$, —$CH_3$, —$CF_3$, —OH, —$OCH_3$, —$OCF_3$, —$CO_2H$, or —$CO_2CH_3$.

16. The method of claim 13, wherein $R_7$ is —F, —Cl, —Br, —$NO_2$, —$CH_3$, —$CF_3$, —OH, —$OCH_3$, —$OCF_3$, —$CO_2H$, or —$CO_2CH_3$.

17. The method of claim 1, wherein the compound of formula (I) is:

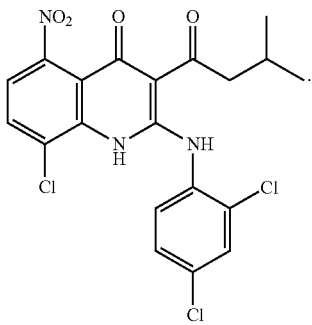 [SMILES: CC(C)CC(=O)c1c(Nc2ccc(Cl)cc2Cl)[nH]c2c(Cl)ccc([N+](=O)[O-])c2c1=O]

18. The method of claim 1, wherein the compound of formula (I) is selected from Table 1.

19. The method of claim 1, wherein the one or more compounds of formula (I) is provided as a pharmaceutical composition comprising the one or more compounds and a pharmaceutically acceptable carrier, an excipient, a diluent, or a combination thereof.

20. The method of claim 1, wherein the compound of formula (I) is selected from Table 2.

* * * * *